United States Patent
Mann et al.

(10) Patent No.: US 9,063,149 B2
(45) Date of Patent: Jun. 23, 2015

(54) QUANTITATIVE STANDARD FOR MASS SPECTROMETRY OF PROTEINS

(75) Inventors: Matthias Mann, Stockdorf (DE); Marlis Zeiler, Weißkirchen/Troun (AT); Mathias Uhlen, Stocksund (SE); Emma Lundberg, Stockholm (SE); Werner Lothar Straube, Vienna (AT)

(73) Assignees: Max-Planck-Gesellschaft zur Förderung der Wissenschaften e.V., München (DE); ATLAS ANTIBODIES AB, Stockholm (SE)

( * ) Notice: Subject to any disclaimer, the term of this patent is extended or adjusted under 35 U.S.C. 154(b) by 0 days.

(21) Appl. No.: 14/009,801

(22) PCT Filed: Apr. 4, 2012

(86) PCT No.: PCT/EP2012/056234
§ 371 (c)(1),
(2), (4) Date: Nov. 18, 2013

(87) PCT Pub. No.: WO2012/136737
PCT Pub. Date: Oct. 11, 2012

(65) Prior Publication Data
US 2014/0072991 A1 Mar. 13, 2014

Related U.S. Application Data

(60) Provisional application No. 61/471,528, filed on Apr. 4, 2011, provisional application No. 61/471,534, filed on Apr. 4, 2011.

(30) Foreign Application Priority Data

Apr. 4, 2011 (EP) .................................... 11002794

(51) Int. Cl.
| | |
|---|---|
| *C12Q 1/37* | (2006.01) |
| *A61K 38/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *G01N 33/68* | (2006.01) |
| *C07K 19/00* | (2006.01) |

(52) U.S. Cl.
CPC ........ *G01N 33/6848* (2013.01); *C07B 2200/05* (2013.01); *C07K 19/00* (2013.01); *C07K 2319/00* (2013.01); *C07K 2319/23* (2013.01); *C07K 2319/24* (2013.01); *C07K 2319/50* (2013.01); *C07K 2319/705* (2013.01)

(58) Field of Classification Search
CPC ............... C07B 2200/05; C07K 19/00; C07K 2319/00; C07K 2319/23; C07K 2319/24; C07K 2319/50; C07K 2319/705; G01N 33/6848

See application file for complete search history.

(56) References Cited

U.S. PATENT DOCUMENTS

2004/0214272 A1* 10/2004 La Rosa et al. .............. 435/69.1
2008/0081343 A1    4/2008 Haynes et al.

FOREIGN PATENT DOCUMENTS

| WO | 9614416 | 5/1996 |
|---|---|---|
| WO | 03016861 | 2/2003 |
| WO | 03102220 | 12/2003 |
| WO | 2006128492 | 12/2006 |
| WO | 2008154619 | 12/2008 |

OTHER PUBLICATIONS

Nanavati Dhaval et al. "Stoichiometry and absolute quantification of proteins with mass spectrometry using fluorescent and isotope-labeled concatenated peptide standards," Molecular & Cellular Proteomics, American Society for Biochemistry and Molecular Biology, Inc., US, vol. 7, No. 2, Feb. 1, 2008. pp. 442-447.

Bigler Wang, et al. Binding of [beta] 4 [ gamma] 5 by Adenosine A 1 and A 2A Receptors Determined by Stable Isotope Labeling with Amino Acids in Cell Culture and Mass Spectrometry, Biochemistry, vol. 50, No. 2, Jan. 18, 2011, pp. 207-220.

Farmen SL et al. "Quantitative Proteomic Analysis of AP12-MALT1 Expression Signature by Isobaric Tags and High-Energy C-TRAP Dissociation Tandem Mass Spectrometry." Laboratory Investigation, vol. 89, No. Suppl. 1, Jan. 2001, pp. 370A-371A.

Moon JY et al., "Expression and purification of a recombinant LL-37 from *Escherichia coli*", Biochimica et Biophysica Acta, vol. 1758, 2006, pp. 1351-1358.

Gudmundsson G H et al., "The Human Gene Fall39 and Processing of the Catherin Precursor to the antibacterial peptide LL-37 in granulocytes", European Journal of Biochemistry, Blackwell Publishing, Berlin, DE. vol. 238, No. 2, Jan. 1, 1996, pp. 325-332.

Database UniProt, "GST26_SCHJA", http://www.uniprot.org/uniprot/P08515, Database accession No. P08515.

Halbhuber et al. "Overexpression and purification of recombinant membrane PsbH protein in *Escherichia coli*", Protein Expression and Purification, Academic Press, San Diego, CA, vol. 32, No. 1. pp. 18-27.

Li-Hsueh Chang et al. "The single cysteine residue on an alpha family chick liver glutathione S-transferase CL 3-3 is not functionally important", Biochemical and Biophysical Research Communications, vol. 180, No. 1, Oct. 1, 1991, pp. 323-328.

(Continued)

*Primary Examiner* — Marcela M Cordero Garcia
(74) *Attorney, Agent, or Firm* — DT Ward, PC; Donna T. Ward; Lingyun Jia

(57) ABSTRACT

This invention relates to a method of determining the absolute amount of a target polypeptide in a sample using mass spectrometry.

36 Claims, 14 Drawing Sheets

(56) References Cited

OTHER PUBLICATIONS

J. Rivers et al. "Absolute Multiplexed Quantitative Analysis of Protein Expression during Muscle Development Using QconCAT", Molecular & Cellular Proteomics, vol. 6, No. 8, Jan. 1, 2007, pp. 1416-9476.

International Search Report for International Application No. PCT/EP2012/056234, dated Aug. 8, 2012.

Stys, et al. "Secondary structure estimation of recombinant psbH, encoding a photosynthetic membrane protein of *Cyanobacterium synechocystis* sp. PCC 6803", Photosynthetica; International Journal of Photosynthesis Research, Kluwer Academic Publishes, DO, vol. 43, No. 3, Sep. 1, 2005, pp. 421-424.

Zeiler, Marlis, et al. "A Protein Epitope Signature Tag (PrEST) Library Allows SILAC-based Absolute Quantification and Multiplexed Determination of Protein Copy Numbers in Cell Lines." The American Society for Biochemistry and Molecular Biology, Inc., 2012.

* cited by examiner

SEQUENCE LISTING

```
<160> NUMBER OF SEQ ID NOS: 258

<210> SEQ ID NO 1
<211> LENGTH: 181
<212> TYPE: PRT
<213> ORGANISM: Streptococcus

<400> SEQUENCE: 1

Met Gly Ser Ser His His His His His His Ser Ser Gly Leu Val Pro
1               5                   10                  15

Arg Gly Ser His Met Ala Ser Leu Ala Glu Ala Lys Val Leu Ala Asn
            20                  25                  30

Arg Glu Leu Asp Lys Tyr Gly Val Ser Asp Tyr His Lys Asn Leu Ile
        35                  40                  45

Asn Asn Ala Lys Thr Val Glu Gly Val Lys Asp Leu Gln Ala Gln Val
    50                  55                  60

Val Glu Ser Ala Lys Lys Ala Arg Ile Ser Glu Ala Thr Asp Gly Leu
65                  70                  75                  80

Ser Asp Phe Leu Lys Ser Gln Thr Pro Ala Glu Asp Thr Val Lys Ser
                85                  90                  95

Ile Glu Leu Ala Glu Ala Lys Val Leu Ala Asn Arg Glu Leu Asp Lys
                100                 105                 110

Tyr Gly Val Ser Asp Tyr Tyr Lys Asn Leu Ile Asn Asn Ala Lys Thr
            115                 120                 125

Val Glu Gly Val Lys Ala Leu Ile Asp Glu Ile Leu Ala Ala Leu Pro
        130                 135                 140

Gly Thr Phe Ala His Tyr Gly Ser Ala Trp Ser His Pro Gln Phe Glu
145                 150                 155                 160

Lys Gly Gly Gly Ser Gly Gly Gly Ser Gly Gly Ser Ala Trp Ser His
                165                 170                 175
```

```
Pro Gln Phe Glu Lys
         180

<210> SEQ ID NO 2
<211> LENGTH: 6
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 2

Thr Val Glu Gly Val Lys
1               5

<210> SEQ ID NO 3
<211> LENGTH: 7
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 3

Asn Leu Ile Asn Asn Ala Lys
1               5

<210> SEQ ID NO 4
<211> LENGTH: 8
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 4

Ser Ile Glu Leu Ala Glu Ala Lys
1               5

<210> SEQ ID NO 5
<211> LENGTH: 8
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 5

Tyr Gly Val Ser Asp Tyr His Lys
1               5

<210> SEQ ID NO 6
<211> LENGTH: 8
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 6

Tyr Gly Val Ser Asp Tyr Tyr Lys
1               5

<210> SEQ ID NO 7
<211> LENGTH: 9
<212> TYPE: PRT
<213> ORGANISM: Artificial Sequence
```

```
<220> FEATURE:
<223> OTHER INFORMATION: fragment derived from the serum albumin binding
      region of streptococcal protein G

<400> SEQUENCE: 7

Val Leu Ala Asn Arg Glu Leu Asp Lys
1               5

<210> SEQ ID NO 8
<211> LENGTH: 10
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 8

Ser Gln Thr Pro Ala Glu Asp Thr Val Lys
1               5                   10

<210> SEQ ID NO 9
<211> LENGTH: 11
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 9

Asp Leu Gln Ala Gln Val Val Glu Ser Ala Lys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 10

Gly Ser His Met Ala Ser Leu Ala Glu Ala Lys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 11

Asp Leu Gln Ala Gln Val Val Glu Ser Ala Lys Lys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 12

Glu Leu Asp Lys Tyr Gly Val Ser Asp Tyr His Lys
1               5                   10
```

<210> SEQ ID NO 13
<211> LENGTH: 12
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 13

Glu Leu Asp Lys Tyr Gly Val Ser Asp Tyr Tyr Lys
1               5                   10

<210> SEQ ID NO 14
<211> LENGTH: 13
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 14

Ile Ser Glu Ala Thr Asp Gly Leu Ser Asp Phe Leu Lys
1               5                   10

<210> SEQ ID NO 15
<211> LENGTH: 13
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 15

Asn Leu Ile Asn Asn Ala Lys Thr Val Glu Gly Val Lys
1               5                   10

<210> SEQ ID NO 16
<211> LENGTH: 13
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 16

Ser Ile Glu Leu Ala Glu Ala Lys Val Leu Ala Asn Arg
1               5                   10

<210> SEQ ID NO 17
<211> LENGTH: 14
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 17

Asp Leu Gln Ala Gln Val Val Glu Ser Ala Lys Lys Ala Arg
1               5                   10

<210> SEQ ID NO 18
<211> LENGTH: 15
<212> TYPE: PRT
<213> ORGANISM: Artificial Sequence
<220> FEATURE:
<223> OTHER INFORMATION: fragment derived from the serum albumin binding
      region of streptococcal protein G -continued

```
<400> SEQUENCE: 18

Ala Arg Ile Ser Glu Ala Thr Asp Gly Leu Ser Asp Phe Leu Lys
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 19

Tyr Gly Val Ser Asp Tyr His Lys Asn Leu Ile Asn Asn Ala Lys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 20

Tyr Gly Val Ser Asp Tyr Tyr Lys Asn Leu Ile Asn Asn Ala Lys
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 21

Gly Ser His Met Ala Ser Leu Ala Glu Ala Lys Val Leu Ala Asn Arg
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 22

Lys Ala Arg Ile Ser Glu Ala Thr Asp Gly Leu Ser Asp Phe Leu Lys
1               5                   10                  15

<210> SEQ ID NO 23
<211> LENGTH: 17
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 23

Met Gly Ser Ser His His His His His His Ser Ser Gly Leu Val Pro
1               5                   10                  15

Arg

<210> SEQ ID NO 24
```

```
<211> LENGTH: 17
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 24

Ser Ile Glu Leu Ala Glu Ala Lys Val Leu Ala Asn Arg Glu Leu Asp
1               5                   10                  15

Lys

<210> SEQ ID NO 25
<211> LENGTH: 17
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 25

Thr Val Glu Gly Val Lys Asp Leu Gln Ala Gln Val Val Glu Ser Ala
1               5                   10                  15

Lys

<210> SEQ ID NO 26
<211> LENGTH: 17
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 26

Val Leu Ala Asn Arg Glu Leu Asp Lys Tyr Gly Val Ser Asp Tyr His
1               5                   10                  15

Lys

<210> SEQ ID NO 27
<211> LENGTH: 17
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 27

Val Leu Ala Asn Arg Glu Leu Asp Lys Tyr Gly Val Ser Asp Tyr Tyr
1               5                   10                  15

Lys

<210> SEQ ID NO 28
<211> LENGTH: 18
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 28

Ser Gln Thr Pro Ala Glu Asp Thr Val Lys Ser Ile Glu Leu Ala Glu
1               5                   10                  15

Ala Lys
```

```
<210> SEQ ID NO 29
<211> LENGTH: 18
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 29

Thr Val Glu Gly Val Lys Asp Leu Gln Ala Gln Val Val Glu Ser Ala
1               5                   10                  15

Lys Lys

<210> SEQ ID NO 30
<211> LENGTH: 19
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 30

Glu Leu Asp Lys Tyr Gly Val Ser Asp Tyr His Lys Asn Leu Ile Asn
1               5                   10                  15

Asn Ala Lys

<210> SEQ ID NO 31
<211> LENGTH: 19
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 31

Glu Leu Asp Lys Tyr Gly Val Ser Asp Tyr Tyr Lys Asn Leu Ile Asn
1               5                   10                  15

Asn Ala Lys

<210> SEQ ID NO 32
<211> LENGTH: 20
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 32

Gly Gly Gly Ser Gly Gly Gly Ser Gly Gly Ser Ala Trp Ser His Pro
1               5                   10                  15

Gln Phe Glu Lys
            20

<210> SEQ ID NO 33
<211> LENGTH: 20
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 33

Gly Ser His Met Ala Ser Leu Ala Glu Ala Lys Val Leu Ala Asn Arg
1               5                   10                  15

Glu Leu Asp Lys
```

```
<210> SEQ ID NO 34
<211> LENGTH: 21
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 34

Tyr Gly Val Ser Asp Tyr His Lys Asn Leu Ile Asn Asn Ala Lys Thr
1               5                   10                  15

Val Glu Gly Val Lys
            20

<210> SEQ ID NO 35
<211> LENGTH: 21
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 35

Tyr Gly Val Ser Asp Tyr Tyr Lys Asn Leu Ile Asn Asn Ala Lys Thr
1               5                   10                  15

Val Glu Gly Val Lys
            20

<210> SEQ ID NO 36
<211> LENGTH: 23
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 36

Ile Ser Glu Ala Thr Asp Gly Leu Ser Asp Phe Leu Lys Ser Gln Thr
1               5                   10                  15

Pro Ala Glu Asp Thr Val Lys
            20

<210> SEQ ID NO 37
<211> LENGTH: 23
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 37

Ser Gln Thr Pro Ala Glu Asp Thr Val Lys Ser Ile Glu Leu Ala Glu
1               5                   10                  15

Ala Lys Val Leu Ala Asn Arg
            20

<210> SEQ ID NO 38
<211> LENGTH: 24
<212> TYPE: PRT
<213> ORGANISM: Artificial Sequence
<220> FEATURE:
<223> OTHER INFORMATION: fragment derived from the serum albumin binding
      region of streptococcal protein G
```

-continued

<400> SEQUENCE: 38

Asn Leu Ile Asn Asn Ala Lys Thr Val Glu Gly Val Lys Asp Leu Gln
1               5                   10                  15

Ala Gln Val Val Glu Ser Ala Lys
            20

<210> SEQ ID NO 39
<211> LENGTH: 25
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 39

Ala Arg Ile Ser Glu Ala Thr Asp Gly Leu Ser Asp Phe Leu Lys Ser
1               5                   10                  15

Gln Thr Pro Ala Glu Asp Thr Val Lys
            20                  25

<210> SEQ ID NO 40
<211> LENGTH: 28
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 40

Ala Leu Ile Asp Glu Ile Leu Ala Ala Leu Pro Gly Thr Phe Ala His
1               5                   10                  15

Tyr Gly Ser Ala Trp Ser His Pro Gln Phe Glu Lys
            20                  25

<210> SEQ ID NO 41
<211> LENGTH: 28
<212> TYPE: PRT
<213> ORGANISM: Artificial Sequence
<220> FEATURE:
<223> OTHER INFORMATION: fragment derived from the serum albumin binding
      region of streptococcal protein G

<400> SEQUENCE: 41

Met Gly Ser Ser His His His His His His Ser Ser Gly Leu Val Pro
1               5                   10                  15

Arg Gly Ser His Met Ala Ser Leu Ala Glu Ala Lys
            20                  25

<210> SEQ ID NO 42
<211> LENGTH: 13
<212> TYPE: PRT
<213> ORGANISM: Homo sapiens

<400> SEQUENCE: 42

Ala Asp Leu Pro Pro Cys Gly Ala Cys Ile Thr Gly Arg
1               5                   10

<210> SEQ ID NO 43
<211> LENGTH: 12
<212> TYPE: PRT
<213> ORGANISM: Homo sapiens

<400> SEQUENCE: 43

Gly Cys Cys Ala Pro Val Gln Val Val Gly Pro Arg

```
<210> SEQ ID NO 44
<211> LENGTH: 20
<212> TYPE: PRT
<213> ORGANISM: Homo sapiens

<400> SEQUENCE: 44

Ile Met Arg Pro Asp Asp Ala Asn Val Ala Gly Asn Val His Gly Gly
1               5                   10                  15

Thr Ile Leu Lys
            20

<210> SEQ ID NO 45
<211> LENGTH: 11
<212> TYPE: PRT
<213> ORGANISM: Homo sapiens

<400> SEQUENCE: 45

Leu Val Ala Gly Gln Gly Cys Val Gly Pro Arg
1               5                   10

<210> SEQ ID NO 46
<211> LENGTH: 12
<212> TYPE: PRT
<213> ORGANISM: Homo sapiens

<400> SEQUENCE: 46

Met Ile Glu Glu Ala Gly Ala Ile Ile Ser Thr Arg
1               5                   10

<210> SEQ ID NO 47
<211> LENGTH: 7
<212> TYPE: PRT
<213> ORGANISM: Homo sapiens

<400> SEQUENCE: 47

Glu Gln Tyr Leu Tyr Thr Lys
1               5

<210> SEQ ID NO 48
<211> LENGTH: 9
<212> TYPE: PRT
<213> ORGANISM: Homo sapiens

<400> SEQUENCE: 48

His Leu Ser Asp Ser Ile Asn Gln Lys
1               5

<210> SEQ ID NO 49
<211> LENGTH: 8
<212> TYPE: PRT
<213> ORGANISM: Homo sapiens

<400> SEQUENCE: 49

Met Cys Met Thr Leu Gly Gly Arg
1               5

<210> SEQ ID NO 50
<211> LENGTH: 9
<212> TYPE: PRT
<213> ORGANISM: Homo sapiens

<400> SEQUENCE: 50
```

```
Val Ser Glu Glu Ile Phe Phe Gly Arg
1               5
```

<210> SEQ ID NO 51
<211> LENGTH: 10
<212> TYPE: PRT
<213> ORGANISM: Homo sapiens

<400> SEQUENCE: 51

```
Asp Asn Phe Asn Phe Leu His Leu Asn Arg
1               5                   10
```

<210> SEQ ID NO 52
<211> LENGTH: 12
<212> TYPE: PRT
<213> ORGANISM: Homo sapiens

<400> SEQUENCE: 52

```
Ile Met Asn Val Ile Gly Glu Pro Ile Asp Glu Arg
1               5                   10
```

<210> SEQ ID NO 53
<211> LENGTH: 10
<212> TYPE: PRT
<213> ORGANISM: Homo sapiens

<400> SEQUENCE: 53

```
Ile Pro Val Gly Pro Glu Thr Leu Gly Arg
1               5                   10
```

<210> SEQ ID NO 54
<211> LENGTH: 15
<212> TYPE: PRT
<213> ORGANISM: Homo sapiens

<400> SEQUENCE: 54

```
Leu Val Leu Glu Val Ala Gln His Leu Gly Glu Ser Thr Val Arg
1               5                   10                  15
```

<210> SEQ ID NO 55
<211> LENGTH: 12
<212> TYPE: PRT
<213> ORGANISM: Homo sapiens

<400> SEQUENCE: 55

```
Thr Ile Ala Met Asp Gly Thr Glu Gly Leu Val Arg
1               5                   10
```

<210> SEQ ID NO 56
<211> LENGTH: 9
<212> TYPE: PRT
<213> ORGANISM: Homo sapiens

<400> SEQUENCE: 56

```
Val Leu Asp Ser Gly Ala Pro Ile Lys
1               5
```

<210> SEQ ID NO 57
<211> LENGTH: 19
<212> TYPE: PRT
<213> ORGANISM: Homo sapiens

<400> SEQUENCE: 57

```
Val Leu Asp Ser Gly Ala Pro Ile Lys Ile Pro Val Gly Pro Glu Thr
1               5                   10                  15
```

Leu Gly Arg

<210> SEQ ID NO 58
<211> LENGTH: 7
<212> TYPE: PRT
<213> ORGANISM: Homo sapiens

<400> SEQUENCE: 58

Ala Leu Phe Pro Glu Pro Arg
1               5

<210> SEQ ID NO 59
<211> LENGTH: 17
<212> TYPE: PRT
<213> ORGANISM: Homo sapiens

<400> SEQUENCE: 59

Ala Val Glu Leu Gly Asp Glu Leu Gln Ile Asp Ala Ile Asp Asp Gln
1               5                   10                  15

Lys

<210> SEQ ID NO 60
<211> LENGTH: 14
<212> TYPE: PRT
<213> ORGANISM: Homo sapiens

<400> SEQUENCE: 60

Cys Asp Ile Leu Val Gln Glu Glu Leu Leu Ala Ser Pro Lys
1               5                   10

<210> SEQ ID NO 61
<211> LENGTH: 17
<212> TYPE: PRT
<213> ORGANISM: Homo sapiens

<400> SEQUENCE: 61

Asp Asn Gln Glu Ser Ser Asp Ala Glu Leu Ser Ser Ser Glu Tyr Ile
1               5                   10                  15

Lys

<210> SEQ ID NO 62
<211> LENGTH: 9
<212> TYPE: PRT
<213> ORGANISM: Homo sapiens

<400> SEQUENCE: 62

His Ala Leu Phe Pro Glu Leu Pro Lys
1               5

<210> SEQ ID NO 63
<211> LENGTH: 18
<212> TYPE: PRT
<213> ORGANISM: Homo sapiens

<400> SEQUENCE: 63

Lys Asp Asn Gln Glu Ser Ser Asp Ala Glu Leu Ser Ser Ser Glu Tyr
1               5                   10                  15

Ile Lys

<210> SEQ ID NO 64
<211> LENGTH: 11
<212> TYPE: PRT

<213> ORGANISM: Homo sapiens

<400> SEQUENCE: 64

Leu Leu Glu Asp Thr Leu Phe Pro Ser Ser Lys
1               5                   10

<210> SEQ ID NO 65
<211> LENGTH: 7
<212> TYPE: PRT
<213> ORGANISM: Homo sapiens

<400> SEQUENCE: 65

Cys Ile Leu Pro Phe Asp Lys
1               5

<210> SEQ ID NO 66
<211> LENGTH: 10
<212> TYPE: PRT
<213> ORGANISM: Homo sapiens

<400> SEQUENCE: 66

Glu His Phe Ala Gln Phe Gly His Val Arg
1               5                   10

<210> SEQ ID NO 67
<211> LENGTH: 14
<212> TYPE: PRT
<213> ORGANISM: Homo sapiens

<400> SEQUENCE: 67

Gly Leu Gly Trp Val Gln Phe Ser Ser Glu Glu Gly Leu Arg
1               5                   10

<210> SEQ ID NO 68
<211> LENGTH: 11
<212> TYPE: PRT
<213> ORGANISM: Homo sapiens

<400> SEQUENCE: 68

Ile Pro Trp Thr Ala Ala Ser Ser Gln Leu Lys
1               5                   10

<210> SEQ ID NO 69
<211> LENGTH: 14
<212> TYPE: PRT
<213> ORGANISM: Homo sapiens

<400> SEQUENCE: 69

Asn Ala Leu Gln Gln Glu Asn His Ile Ile Asp Gly Val Lys
1               5                   10

<210> SEQ ID NO 70
<211> LENGTH: 10
<212> TYPE: PRT
<213> ORGANISM: Homo sapiens

<400> SEQUENCE: 70

Ser Ile Asn Gln Pro Val Ala Phe Val Arg
1               5                   10

<210> SEQ ID NO 71
<211> LENGTH: 9
<212> TYPE: PRT
<213> ORGANISM: Homo sapiens

```
<400> SEQUENCE: 71

Ile Leu Val Glu Leu Ala Asp Glu Lys
1               5

<210> SEQ ID NO 72
<211> LENGTH: 16
<212> TYPE: PRT
<213> ORGANISM: Homo sapiens

<400> SEQUENCE: 72

Gly Asp Ser Glu Ser Glu Glu Asp Glu Gln Asp Ser Glu Glu Val Arg
1               5                   10                  15

<210> SEQ ID NO 73
<211> LENGTH: 17
<212> TYPE: PRT
<213> ORGANISM: Homo sapiens

<400> SEQUENCE: 73

Arg Gly Asp Ser Glu Ser Glu Glu Asp Glu Gln Asp Ser Glu Glu Val
1               5                   10                  15

Arg

<210> SEQ ID NO 74
<211> LENGTH: 15
<212> TYPE: PRT
<213> ORGANISM: Homo sapiens

<400> SEQUENCE: 74

Val Gln Glu Glu Thr Thr Leu Val Asp Asp Pro Phe Gln Met Lys
1               5                   10                  15

<210> SEQ ID NO 75
<211> LENGTH: 12
<212> TYPE: PRT
<213> ORGANISM: Homo sapiens

<400> SEQUENCE: 75

Ala Phe Glu Asn Cys Ser Glu Asp Leu Gln Glu Arg
1               5                   10

<210> SEQ ID NO 76
<211> LENGTH: 16
<212> TYPE: PRT
<213> ORGANISM: Homo sapiens

<400> SEQUENCE: 76

Phe His Ser Glu Thr Leu Thr Glu Gly Asp Leu Val Asp Leu Met Lys
1               5                   10                  15

<210> SEQ ID NO 77
<211> LENGTH: 7
<212> TYPE: PRT
<213> ORGANISM: Homo sapiens

<400> SEQUENCE: 77

Thr Asn Phe Phe Ala Thr Arg
1               5

<210> SEQ ID NO 78
<211> LENGTH: 11
<212> TYPE: PRT
<213> ORGANISM: Homo sapiens
```

```
<400> SEQUENCE: 78

Val Val Asn Ile Ser Ser Leu Gln Cys Leu Arg
1               5                   10

<210> SEQ ID NO 79
<211> LENGTH: 15
<212> TYPE: PRT
<213> ORGANISM: Homo sapiens

<400> SEQUENCE: 79

Asn Gln Glu Lys Pro Ser Asn Ser Glu Ser Ser Leu Gly Ala Lys
1               5                   10                  15

<210> SEQ ID NO 80
<211> LENGTH: 9
<212> TYPE: PRT
<213> ORGANISM: Homo sapiens

<400> SEQUENCE: 80

His Gly Ile Asn Cys Phe Ile Asn Arg
1               5

<210> SEQ ID NO 81
<211> LENGTH: 12
<212> TYPE: PRT
<213> ORGANISM: Homo sapiens

<400> SEQUENCE: 81

Ile Leu Ile Ala Asn Thr Gly Met Asp Thr Asp Lys
1               5                   10

<210> SEQ ID NO 82
<211> LENGTH: 14
<212> TYPE: PRT
<213> ORGANISM: Homo sapiens

<400> SEQUENCE: 82

Ile Leu Ile Ala Asn Thr Gly Met Asp Thr Asp Lys Ile Lys
1               5                   10

<210> SEQ ID NO 83
<211> LENGTH: 20
<212> TYPE: PRT
<213> ORGANISM: Homo sapiens

<400> SEQUENCE: 83

Leu Ala Leu Val Thr Gly Gly Glu Ile Ala Ser Thr Phe Asp His Pro
1               5                   10                  15

Glu Leu Val Lys
            20

<210> SEQ ID NO 84
<211> LENGTH: 11
<212> TYPE: PRT
<213> ORGANISM: Homo sapiens

<400> SEQUENCE: 84

Leu Ile Glu Glu Val Met Ile Gly Glu Asp Lys
1               5                   10

<210> SEQ ID NO 85
<211> LENGTH: 9
<212> TYPE: PRT
<213> ORGANISM: Homo sapiens
```

<400> SEQUENCE: 85

Val Ala Glu Ile Glu His Ala Glu Lys
1               5

<210> SEQ ID NO 86
<211> LENGTH: 11
<212> TYPE: PRT
<213> ORGANISM: Homo sapiens

<400> SEQUENCE: 86

Val Ala Glu Ile Glu His Ala Glu Lys Glu Lys
1               5                   10

<210> SEQ ID NO 87
<211> LENGTH: 7
<212> TYPE: PRT
<213> ORGANISM: Homo sapiens

<400> SEQUENCE: 87

Ile Ala Gln Gln Leu Glu Arg
1               5

<210> SEQ ID NO 88
<211> LENGTH: 8
<212> TYPE: PRT
<213> ORGANISM: Homo sapiens

<400> SEQUENCE: 88

Tyr Gln Glu Gln Leu Leu Asp Arg
1               5

<210> SEQ ID NO 89
<211> LENGTH: 6
<212> TYPE: PRT
<213> ORGANISM: Homo sapiens

<400> SEQUENCE: 89

Asp His His Tyr Phe Lys
1               5

<210> SEQ ID NO 90
<211> LENGTH: 8
<212> TYPE: PRT
<213> ORGANISM: Homo sapiens

<400> SEQUENCE: 90

Ile Ser Ala Leu Ala Leu Leu Lys
1               5

<210> SEQ ID NO 91
<211> LENGTH: 14
<212> TYPE: PRT
<213> ORGANISM: Homo sapiens

<400> SEQUENCE: 91

Ser Gly Gly Asn Leu Glu Val Met Gly Leu Met Leu Gly Lys
1               5                   10

<210> SEQ ID NO 92
<211> LENGTH: 22
<212> TYPE: PRT
<213> ORGANISM: Homo sapiens

<400> SEQUENCE: 92

```
Val Asp Gly Glu Thr Met Ile Ile Met Asp Ser Phe Ala Leu Pro Val
1               5                   10                  15

Glu Gly Thr Glu Thr Arg
            20
```

<210> SEQ ID NO 93
<211> LENGTH: 9
<212> TYPE: PRT
<213> ORGANISM: Homo sapiens

<400> SEQUENCE: 93

```
Leu Leu His Asp Leu Asn Phe Ser Lys
1               5
```

<210> SEQ ID NO 94
<211> LENGTH: 14
<212> TYPE: PRT
<213> ORGANISM: Homo sapiens

<400> SEQUENCE: 94

```
Gln Gly His Ile Ser Pro Ala Leu Leu Ser Glu Phe Leu Lys
1               5                   10
```

<210> SEQ ID NO 95
<211> LENGTH: 8
<212> TYPE: PRT
<213> ORGANISM: Homo sapiens

<400> SEQUENCE: 95

```
Thr Glu Asp Asp Ile Ile Trp Arg
1               5
```

<210> SEQ ID NO 96
<211> LENGTH: 9
<212> TYPE: PRT
<213> ORGANISM: Homo sapiens

<400> SEQUENCE: 96

```
Gly Glu Glu Glu Asn Met Met Met Arg
1               5
```

<210> SEQ ID NO 97
<211> LENGTH: 10
<212> TYPE: PRT
<213> ORGANISM: Homo sapiens

<400> SEQUENCE: 97

```
Val Leu Ile Ser Thr Asp Leu Thr Ser Arg
1               5                   10
```

<210> SEQ ID NO 98
<211> LENGTH: 9
<212> TYPE: PRT
<213> ORGANISM: Homo sapiens

<400> SEQUENCE: 98

```
Glu Gly Met Thr Ala Phe Val Glu Lys
1               5
```

<210> SEQ ID NO 99
<211> LENGTH: 16
<212> TYPE: PRT
<213> ORGANISM: Homo sapiens

<400> SEQUENCE: 99

Glu Ser Val Asn Ala Ala Phe Glu Met Thr Leu Thr Glu Gly Ser Lys
1               5                   10                  15

<210> SEQ ID NO 100
<211> LENGTH: 17
<212> TYPE: PRT
<213> ORGANISM: Homo sapiens

<400> SEQUENCE: 100

Ile Cys Pro Val Glu Thr Leu Val Glu Glu Ala Ile Gln Cys Ala Glu
1               5                   10                  15

Lys

<210> SEQ ID NO 101
<211> LENGTH: 7
<212> TYPE: PRT
<213> ORGANISM: Homo sapiens

<400> SEQUENCE: 101

Ile Ser Ala Gln Asp Ala Lys
1               5

<210> SEQ ID NO 102
<211> LENGTH: 7
<212> TYPE: PRT
<213> ORGANISM: Homo sapiens

<400> SEQUENCE: 102

Ile Val Val Ala Met Ala Lys
1               5

<210> SEQ ID NO 103
<211> LENGTH: 10
<212> TYPE: PRT
<213> ORGANISM: Homo sapiens

<400> SEQUENCE: 103

Lys Glu Gly Met Thr Ala Phe Val Glu Lys
1               5                   10

<210> SEQ ID NO 104
<211> LENGTH: 12
<212> TYPE: PRT
<213> ORGANISM: Homo sapiens

<400> SEQUENCE: 104

Lys Leu Phe Tyr Ser Thr Phe Ala Thr Asp Asp Arg
1               5                   10

<210> SEQ ID NO 105
<211> LENGTH: 12
<212> TYPE: PRT
<213> ORGANISM: Homo sapiens

<400> SEQUENCE: 105

Leu Phe Tyr Ser Thr Phe Ala Thr Asp Asp Arg Lys
1               5                   10

<210> SEQ ID NO 106
<211> LENGTH: 7
<212> TYPE: PRT
<213> ORGANISM: Homo sapiens

```
<400> SEQUENCE: 106

Gln Ala Gly Leu Val Ser Lys
1               5

<210> SEQ ID NO 107
<211> LENGTH: 12
<212> TYPE: PRT
<213> ORGANISM: Homo sapiens

<400> SEQUENCE: 107

Ser Leu Ala Met Glu Met Val Leu Thr Gly Asp Arg
1               5                   10

<210> SEQ ID NO 108
<211> LENGTH: 20
<212> TYPE: PRT
<213> ORGANISM: Homo sapiens

<400> SEQUENCE: 108

Leu Gly His Val Val Met Gly Asn Asn Ala Val Ser Pro Tyr Gln Gln
1               5                   10                  15

Val Ile Glu Lys
            20

<210> SEQ ID NO 109
<211> LENGTH: 10
<212> TYPE: PRT
<213> ORGANISM: Homo sapiens

<400> SEQUENCE: 109

Leu Asn Met Thr Pro Glu Glu Ala Glu Arg
1               5                   10

<210> SEQ ID NO 110
<211> LENGTH: 10
<212> TYPE: PRT
<213> ORGANISM: Homo sapiens

<400> SEQUENCE: 110

Ser Gln Met Leu Ala Met Asn Ile Glu Lys
1               5                   10

<210> SEQ ID NO 111
<211> LENGTH: 7
<212> TYPE: PRT
<213> ORGANISM: Homo sapiens

<400> SEQUENCE: 111

Trp Ile Val Asn Leu Ile Arg
1               5

<210> SEQ ID NO 112
<211> LENGTH: 10
<212> TYPE: PRT
<213> ORGANISM: Homo sapiens

<400> SEQUENCE: 112

Ala Asp Ala Glu Cys Tyr Thr Ala Met Lys
1               5                   10

<210> SEQ ID NO 113
<211> LENGTH: 15
<212> TYPE: PRT
<213> ORGANISM: Homo sapiens
```

<400> SEQUENCE: 113

Asp Ile Pro Asn Met Phe Met Asp Ser Ala Gly Ser Val Ser Lys
1               5                   10                  15

<210> SEQ ID NO 114
<211> LENGTH: 15
<212> TYPE: PRT
<213> ORGANISM: Homo sapiens

<400> SEQUENCE: 114

Leu Ser Phe Gly Leu Glu Asp Glu Pro Leu Glu Thr Ala Thr Lys
1               5                   10                  15

<210> SEQ ID NO 115
<211> LENGTH: 10
<212> TYPE: PRT
<213> ORGANISM: Homo sapiens

<400> SEQUENCE: 115

Leu Thr Pro Glu Tyr Leu Gln Leu Met Lys
1               5                   10

<210> SEQ ID NO 116
<211> LENGTH: 8
<212> TYPE: PRT
<213> ORGANISM: Homo sapiens

<400> SEQUENCE: 116

Gln Phe Glu Gly Leu Ala Asp Lys
1               5

<210> SEQ ID NO 117
<211> LENGTH: 12
<212> TYPE: PRT
<213> ORGANISM: Homo sapiens

<400> SEQUENCE: 117

Val Ala Gln Val Ala Glu Ile Thr Tyr Gly Gln Lys
1               5                   10

<210> SEQ ID NO 118
<211> LENGTH: 11
<212> TYPE: PRT
<213> ORGANISM: Homo sapiens

<400> SEQUENCE: 118

Ala Ala Leu Gln Glu Glu Leu Gln Leu Cys Lys
1               5                   10

<210> SEQ ID NO 119
<211> LENGTH: 9
<212> TYPE: PRT
<213> ORGANISM: Homo sapiens

<400> SEQUENCE: 119

Asp Pro Ser Gln Gln Glu Leu Pro Arg
1               5

<210> SEQ ID NO 120
<211> LENGTH: 15
<212> TYPE: PRT
<213> ORGANISM: Homo sapiens

<400> SEQUENCE: 120

```
Phe Cys Phe Thr Pro His Thr Glu Glu Gly Cys Leu Ser Glu Arg
1               5                   10                  15
```

<210> SEQ ID NO 121
<211> LENGTH: 9
<212> TYPE: PRT
<213> ORGANISM: Homo sapiens

<400> SEQUENCE: 121

```
Gly Leu Val Gln Ala Leu Gln Thr Lys
1               5
```

<210> SEQ ID NO 122
<211> LENGTH: 7
<212> TYPE: PRT
<213> ORGANISM: Homo sapiens

<400> SEQUENCE: 122

```
Leu Leu Ser Ala Ala Cys Arg
1               5
```

<210> SEQ ID NO 123
<211> LENGTH: 13
<212> TYPE: PRT
<213> ORGANISM: Homo sapiens

<400> SEQUENCE: 123

```
Met Val Val Pro Gly Leu Asp Gly Ala Gln Ile Pro Arg
1               5                   10
```

<210> SEQ ID NO 124
<211> LENGTH: 11
<212> TYPE: PRT
<213> ORGANISM: Homo sapiens

<400> SEQUENCE: 124

```
Gln Gln Glu Gln Gln Val Pro Ile Leu Glu Lys
1               5                   10
```

<210> SEQ ID NO 125
<211> LENGTH: 12
<212> TYPE: PRT
<213> ORGANISM: Homo sapiens

<400> SEQUENCE: 125

```
Arg Gln Gln Glu Gln Gln Val Pro Ile Leu Glu Lys
1               5                   10
```

<210> SEQ ID NO 126
<211> LENGTH: 7
<212> TYPE: PRT
<213> ORGANISM: Homo sapiens

<400> SEQUENCE: 126

```
Val Thr Gln Gln Gly Leu Lys
1               5
```

<210> SEQ ID NO 127
<211> LENGTH: 19
<212> TYPE: PRT
<213> ORGANISM: Homo sapiens

<400> SEQUENCE: 127

```
Val Thr Val Ala Gly Gly Val His Ile Ser Gly Leu His Thr Glu Ser
```

-continued

```
                1               5                  10                  15

Ala Pro Arg

<210> SEQ ID NO 128
<211> LENGTH: 7
<212> TYPE: PRT
<213> ORGANISM: Homo sapiens

<400> SEQUENCE: 128

Ala Val Asp Leu Ile Gln Lys
1               5

<210> SEQ ID NO 129
<211> LENGTH: 20
<212> TYPE: PRT
<213> ORGANISM: Homo sapiens

<400> SEQUENCE: 129

Glu Ala His Gln Leu Phe Leu Glu Pro Glu Val Leu Asp Pro Glu Ser
1               5                  10                  15

Val Glu Leu Lys
            20

<210> SEQ ID NO 130
<211> LENGTH: 8
<212> TYPE: PRT
<213> ORGANISM: Homo sapiens

<400> SEQUENCE: 130

His Leu Thr Ala Ser Glu Ala Lys
1               5

<210> SEQ ID NO 131
<211> LENGTH: 15
<212> TYPE: PRT
<213> ORGANISM: Homo sapiens

<400> SEQUENCE: 131

Leu Asp Pro Asn Lys Tyr Pro Val Pro Glu Asn Trp Leu His Lys
1               5                  10                  15

<210> SEQ ID NO 132
<211> LENGTH: 10
<212> TYPE: PRT
<213> ORGANISM: Homo sapiens

<400> SEQUENCE: 132

Leu Pro Ile Gln Glu Phe His Leu Ser Arg
1               5                  10

<210> SEQ ID NO 133
<211> LENGTH: 7
<212> TYPE: PRT
<213> ORGANISM: Homo sapiens

<400> SEQUENCE: 133

Ser Ile Glu Glu Ile Val Arg
1               5

<210> SEQ ID NO 134
<211> LENGTH: 21
<212> TYPE: PRT
<213> ORGANISM: Homo sapiens
```

-continued

<400> SEQUENCE: 134

Val Tyr Ala Ala Ala Thr Glu Asp Met Asp Cys Leu Thr Phe Gly Ser
1               5                   10                  15

Pro Val Leu Met Arg
            20

<210> SEQ ID NO 135
<211> LENGTH: 10
<212> TYPE: PRT
<213> ORGANISM: Homo sapiens

<400> SEQUENCE: 135

Tyr Pro Val Pro Glu Asn Trp Leu His Lys
1               5                   10

<210> SEQ ID NO 136
<211> LENGTH: 17
<212> TYPE: PRT
<213> ORGANISM: Homo sapiens

<400> SEQUENCE: 136

Glu Leu Thr Asp Thr Leu Gln Ala Glu Thr Asp Gln Leu Glu Asp Glu
1               5                   10                  15

Lys

<210> SEQ ID NO 137
<211> LENGTH: 13
<212> TYPE: PRT
<213> ORGANISM: Homo sapiens

<400> SEQUENCE: 137

Gly Lys Val Glu Gln Leu Ser Pro Glu Glu Glu Glu Lys
1               5                   10

<210> SEQ ID NO 138
<211> LENGTH: 12
<212> TYPE: PRT
<213> ORGANISM: Homo sapiens

<400> SEQUENCE: 138

Ser Ala Leu Gln Thr Glu Ile Ala Asn Leu Leu Lys
1               5                   10

<210> SEQ ID NO 139
<211> LENGTH: 11
<212> TYPE: PRT
<213> ORGANISM: Homo sapiens

<400> SEQUENCE: 139

Val Glu Gln Leu Ser Pro Glu Glu Glu Glu Lys
1               5                   10

<210> SEQ ID NO 140
<211> LENGTH: 14
<212> TYPE: PRT
<213> ORGANISM: Homo sapiens

<400> SEQUENCE: 140

Glu Asp Gln Tyr Asp His Leu Asp Ala Ala Asp Met Thr Lys
1               5                   10

<210> SEQ ID NO 141
<211> LENGTH: 6

```
<212> TYPE: PRT
<213> ORGANISM: Homo sapiens

<400> SEQUENCE: 141

Leu Asn Leu Gln Asn Lys
1               5

<210> SEQ ID NO 142
<211> LENGTH: 16
<212> TYPE: PRT
<213> ORGANISM: Homo sapiens

<400> SEQUENCE: 142

Asn Lys Glu Asp Gln Tyr Asp His Leu Asp Ala Ala Asp Met Thr Lys
1               5                   10                  15

<210> SEQ ID NO 143
<211> LENGTH: 7
<212> TYPE: PRT
<213> ORGANISM: Homo sapiens

<400> SEQUENCE: 143

Gln Ile Gln Gln Tyr Met Lys
1               5

<210> SEQ ID NO 144
<211> LENGTH: 10
<212> TYPE: PRT
<213> ORGANISM: Homo sapiens

<400> SEQUENCE: 144

Gln Ser Leu Thr Met Asp Pro Val Val Lys
1               5                   10

<210> SEQ ID NO 145
<211> LENGTH: 12
<212> TYPE: PRT
<213> ORGANISM: Homo sapiens

<400> SEQUENCE: 145

Ser Thr Asn Glu Ala Met Glu Trp Met Asn Asn Lys
1               5                   10

<210> SEQ ID NO 146
<211> LENGTH: 18
<212> TYPE: PRT
<213> ORGANISM: Homo sapiens

<400> SEQUENCE: 146

Ile Leu Ala Ile Gly Leu Ile Asn Glu Ala Leu Asp Glu Gly Asp Ala
1               5                   10                  15

Gln Lys

<210> SEQ ID NO 147
<211> LENGTH: 18
<212> TYPE: PRT
<213> ORGANISM: Homo sapiens

<400> SEQUENCE: 147

Leu Glu Gly Val Leu Ala Glu Val Ala Gln His Tyr Gln Asp Thr Leu
1               5                   10                  15

Ile Arg
```

<210> SEQ ID NO 148
<211> LENGTH: 19
<212> TYPE: PRT
<213> ORGANISM: Homo sapiens

<400> SEQUENCE: 148

Gln Leu Ser Ser Ser Val Thr Gly Leu Thr Asn Ile Glu Glu Glu Asn
1               5                   10                  15

Cys Gln Arg

<210> SEQ ID NO 149
<211> LENGTH: 11
<212> TYPE: PRT
<213> ORGANISM: Homo sapiens

<400> SEQUENCE: 149

Thr Leu Gln Ala Leu Gln Ile Pro Ala Ala Lys
1               5                   10

<210> SEQ ID NO 150
<211> LENGTH: 7
<212> TYPE: PRT
<213> ORGANISM: Homo sapiens

<400> SEQUENCE: 150

Tyr Leu Asp Glu Leu Met Lys
1               5

<210> SEQ ID NO 151
<211> LENGTH: 10
<212> TYPE: PRT
<213> ORGANISM: Homo sapiens

<400> SEQUENCE: 151

Glu Leu Ala Pro Leu Phe Glu Glu Leu Arg
1               5                   10

<210> SEQ ID NO 152
<211> LENGTH: 16
<212> TYPE: PRT
<213> ORGANISM: Homo sapiens

<400> SEQUENCE: 152

Lys Leu Pro Ser Val Glu Gly Leu His Ala Ile Val Val Ser Asp Arg
1               5                   10                  15

<210> SEQ ID NO 153
<211> LENGTH: 24
<212> TYPE: PRT
<213> ORGANISM: Homo sapiens

<400> SEQUENCE: 153

Val Ala Asn Asp Asn Ala Pro Glu His Ala Leu Arg Pro Gly Phe Leu
1               5                   10                  15

Ser Thr Phe Ala Leu Ala Thr Ile
            20

<210> SEQ ID NO 154
<211> LENGTH: 6
<212> TYPE: PRT
<213> ORGANISM: Homo sapiens

<400> SEQUENCE: 154

Ala Pro Val Ala Ile Lys

```
1               5

<210> SEQ ID NO 155
<211> LENGTH: 11
<212> TYPE: PRT
<213> ORGANISM: Homo sapiens

<400> SEQUENCE: 155

Ala Tyr Thr Pro Pro Glu Asp Leu Gln Ser Arg
1               5                   10

<210> SEQ ID NO 156
<211> LENGTH: 13
<212> TYPE: PRT
<213> ORGANISM: Homo sapiens

<400> SEQUENCE: 156

Glu Lys Glu Pro Val Val Val Glu Thr Val Glu Glu Lys
1               5                   10

<210> SEQ ID NO 157
<211> LENGTH: 6
<212> TYPE: PRT
<213> ORGANISM: Homo sapiens

<400> SEQUENCE: 157

Leu Glu Ser Tyr Val Lys
1               5

<210> SEQ ID NO 158
<211> LENGTH: 10
<212> TYPE: PRT
<213> ORGANISM: Homo sapiens

<400> SEQUENCE: 158

Ala Leu Leu Ala Glu Gly Val Ile Leu Arg
1               5                   10

<210> SEQ ID NO 159
<211> LENGTH: 8
<212> TYPE: PRT
<213> ORGANISM: Homo sapiens

<400> SEQUENCE: 159

Leu Gly Glu Thr Asp Glu Glu Lys
1               5

<210> SEQ ID NO 160
<211> LENGTH: 10
<212> TYPE: PRT
<213> ORGANISM: Homo sapiens

<400> SEQUENCE: 160

Thr Gln His Gly Gly Ser His Val Ser Arg
1               5                   10

<210> SEQ ID NO 161
<211> LENGTH: 6
<212> TYPE: PRT
<213> ORGANISM: Homo sapiens

<400> SEQUENCE: 161

Tyr Thr Glu Leu Gln Lys
1               5
```

<210> SEQ ID NO 162
<211> LENGTH: 10
<212> TYPE: PRT
<213> ORGANISM: Homo sapiens

<400> SEQUENCE: 162

Ala Gly Gly Phe Ala Ser Ala Leu Glu Arg
1               5                   10

<210> SEQ ID NO 163
<211> LENGTH: 7
<212> TYPE: PRT
<213> ORGANISM: Homo sapiens

<400> SEQUENCE: 163

His Ser Glu Leu Leu Gln Lys
1               5

<210> SEQ ID NO 164
<211> LENGTH: 10
<212> TYPE: PRT
<213> ORGANISM: Homo sapiens

<400> SEQUENCE: 164

Asn Val Glu Ser Phe Ala Ser Met Leu Arg
1               5                   10

<210> SEQ ID NO 165
<211> LENGTH: 8
<212> TYPE: PRT
<213> ORGANISM: Homo sapiens

<400> SEQUENCE: 165

Ala Cys Val Met Met Gln Gly Arg
1               5

<210> SEQ ID NO 166
<211> LENGTH: 15
<212> TYPE: PRT
<213> ORGANISM: Homo sapiens

<400> SEQUENCE: 166

Asp His Ile Asn Leu Pro Gly Phe Ser Gly Gln Asn Pro Leu Arg
1               5                   10                  15

<210> SEQ ID NO 167
<211> LENGTH: 10
<212> TYPE: PRT
<213> ORGANISM: Homo sapiens

<400> SEQUENCE: 167

Phe Glu Val Gly Asp Ile Met Leu Ile Arg
1               5                   10

<210> SEQ ID NO 168
<211> LENGTH: 11
<212> TYPE: PRT
<213> ORGANISM: Homo sapiens

<400> SEQUENCE: 168

Phe His Met Tyr Glu Gly Tyr Pro Leu Trp Lys
1               5                   10

<210> SEQ ID NO 169

```
<211> LENGTH: 19
<212> TYPE: PRT
<213> ORGANISM: Homo sapiens

<400> SEQUENCE: 169

His Arg Pro Gln Val Ala Ile Ile Cys Gly Ser Gly Leu Gly Leu
1               5                   10                  15

Thr Asp Lys

<210> SEQ ID NO 170
<211> LENGTH: 17
<212> TYPE: PRT
<213> ORGANISM: Homo sapiens

<400> SEQUENCE: 170

Leu Thr Gln Ala Gln Ile Phe Asp Tyr Gly Glu Ile Pro Asn Phe Pro
1               5                   10                  15

Arg

<210> SEQ ID NO 171
<211> LENGTH: 9
<212> TYPE: PRT
<213> ORGANISM: Homo sapiens

<400> SEQUENCE: 171

Ser Thr Val Pro Gly His Ala Gly Arg
1               5

<210> SEQ ID NO 172
<211> LENGTH: 22
<212> TYPE: PRT
<213> ORGANISM: Homo sapiens

<400> SEQUENCE: 172

Val Phe His Leu Leu Gly Val Asp Thr Leu Val Val Thr Asn Ala Ala
1               5                   10                  15

Gly Gly Leu Asn Pro Lys
            20

<210> SEQ ID NO 173
<211> LENGTH: 8
<212> TYPE: PRT
<213> ORGANISM: Homo sapiens

<400> SEQUENCE: 173

Ala Asp Leu Cys Gln Leu Ile Arg
1               5

<210> SEQ ID NO 174
<211> LENGTH: 9
<212> TYPE: PRT
<213> ORGANISM: Homo sapiens

<400> SEQUENCE: 174

Ala Glu Gly Ile Leu Leu Leu Val Lys
1               5

<210> SEQ ID NO 175
<211> LENGTH: 9
<212> TYPE: PRT
<213> ORGANISM: Homo sapiens

<400> SEQUENCE: 175
```

Glu Val Asn Leu Gly Leu Leu Ala Lys
1               5

<210> SEQ ID NO 176
<211> LENGTH: 7
<212> TYPE: PRT
<213> ORGANISM: Homo sapiens

<400> SEQUENCE: 176

Glu Ala Glu Asp Asn Ile Arg
1               5

<210> SEQ ID NO 177
<211> LENGTH: 10
<212> TYPE: PRT
<213> ORGANISM: Homo sapiens

<400> SEQUENCE: 177

Glu Ala Ile His Ser Gln Leu Leu Glu Lys
1               5                   10

<210> SEQ ID NO 178
<211> LENGTH: 7
<212> TYPE: PRT
<213> ORGANISM: Homo sapiens

<400> SEQUENCE: 178

Ile Lys Glu Leu Glu Gln Lys
1               5

<210> SEQ ID NO 179
<211> LENGTH: 11
<212> TYPE: PRT
<213> ORGANISM: Homo sapiens

<400> SEQUENCE: 179

Leu Ala Asp Ile Gln Ile Glu Gln Leu Asn Arg
1               5                   10

<210> SEQ ID NO 180
<211> LENGTH: 7
<212> TYPE: PRT
<213> ORGANISM: Homo sapiens

<400> SEQUENCE: 180

Met Phe Ile Leu Gln Ser Lys
1               5

<210> SEQ ID NO 181
<211> LENGTH: 14
<212> TYPE: PRT
<213> ORGANISM: Homo sapiens

<400> SEQUENCE: 181

Asp Lys Pro Leu Lys Asp Val Ile Ala Asp Cys Gly Lys
1               5                   10

<210> SEQ ID NO 182
<211> LENGTH: 13
<212> TYPE: PRT
<213> ORGANISM: Homo sapiens

<400> SEQUENCE: 182

Asp Thr Asn Gly Ser Gln Phe Phe Ile Thr Thr Val Lys
1               5                   10

<210> SEQ ID NO 183
<211> LENGTH: 9
<212> TYPE: PRT
<213> ORGANISM: Homo sapiens

<400> SEQUENCE: 183

Asp Val Ile Ile Ala Asp Cys Gly Lys
1               5

<210> SEQ ID NO 184
<211> LENGTH: 11
<212> TYPE: PRT
<213> ORGANISM: Homo sapiens

<400> SEQUENCE: 184

Ile Glu Val Glu Lys Pro Phe Ala Ile Ala Lys
1               5                   10

<210> SEQ ID NO 185
<211> LENGTH: 7
<212> TYPE: PRT
<213> ORGANISM: Homo sapiens

<400> SEQUENCE: 185

Thr Ala Trp Leu Asp Gly Lys
1               5

<210> SEQ ID NO 186
<211> LENGTH: 9
<212> TYPE: PRT
<213> ORGANISM: Homo sapiens

<400> SEQUENCE: 186

Val Leu Glu Gly Met Glu Val Val Arg
1               5

<210> SEQ ID NO 187
<211> LENGTH: 12
<212> TYPE: PRT
<213> ORGANISM: Homo sapiens

<400> SEQUENCE: 187

Asp Phe Thr Pro Val Cys Thr Thr Glu Leu Gly Arg
1               5                   10

<210> SEQ ID NO 188
<211> LENGTH: 13
<212> TYPE: PRT
<213> ORGANISM: Homo sapiens

<400> SEQUENCE: 188

Asp Ile Asn Ala Tyr Asn Cys Glu Glu Pro Thr Glu Lys
1               5                   10

<210> SEQ ID NO 189
<211> LENGTH: 14
<212> TYPE: PRT
<213> ORGANISM: Homo sapiens

<400> SEQUENCE: 189

Glu Leu Ala Ile Leu Leu Gly Met Leu Asp Pro Ala Glu Lys
1               5                   10

<210> SEQ ID NO 190
<211> LENGTH: 17
<212> TYPE: PRT
<213> ORGANISM: Homo sapiens

<400> SEQUENCE: 190

Glu Leu Ala Ile Leu Leu Gly Met Leu Asp Pro Ala Glu Lys Asp Glu
1               5                   10                  15
Lys

<210> SEQ ID NO 191
<211> LENGTH: 17
<212> TYPE: PRT
<213> ORGANISM: Homo sapiens

<400> SEQUENCE: 191

Phe His Asp Phe Leu Gly Asp Ser Trp Gly Ile Leu Phe Ser His Pro
1               5                   10                  15
Arg

<210> SEQ ID NO 192
<211> LENGTH: 7
<212> TYPE: PRT
<213> ORGANISM: Homo sapiens

<400> SEQUENCE: 192

Gly Met Pro Val Thr Ala Arg
1               5

<210> SEQ ID NO 193
<211> LENGTH: 7
<212> TYPE: PRT
<213> ORGANISM: Homo sapiens

<400> SEQUENCE: 193

Leu Ala Pro Glu Phe Ala Lys
1               5

<210> SEQ ID NO 194
<211> LENGTH: 17
<212> TYPE: PRT
<213> ORGANISM: Homo sapiens

<400> SEQUENCE: 194

Leu Ile Ala Leu Ser Ile Asp Ser Val Glu Asp His Leu Ala Trp Ser
1               5                   10                  15
Lys

<210> SEQ ID NO 195
<211> LENGTH: 9
<212> TYPE: PRT
<213> ORGANISM: Homo sapiens

<400> SEQUENCE: 195

Leu Pro Phe Pro Ile Ile Asp Asp Arg
1               5

<210> SEQ ID NO 196
<211> LENGTH: 9
<212> TYPE: PRT
<213> ORGANISM: Homo sapiens

<400> SEQUENCE: 196

```
Val Val Phe Val Phe Gly Pro Asp Lys
1               5

<210> SEQ ID NO 197
<211> LENGTH: 10
<212> TYPE: PRT
<213> ORGANISM: Homo sapiens

<400> SEQUENCE: 197

Val Val Phe Val Phe Gly Pro Asp Lys Lys
1               5                   10

<210> SEQ ID NO 198
<211> LENGTH: 12
<212> TYPE: PRT
<213> ORGANISM: Homo sapiens

<400> SEQUENCE: 198

Ala Val Cys Val Glu Ala Gly Met Ile Ala Leu Arg
1               5                   10

<210> SEQ ID NO 199
<211> LENGTH: 20
<212> TYPE: PRT
<213> ORGANISM: Homo sapiens

<400> SEQUENCE: 199

Gly Ala Thr Glu Leu Thr His Glu Asp Tyr Met Glu Gly Ile Leu Glu
1               5                   10                  15

Val Gln Ala Lys
            20

<210> SEQ ID NO 200
<211> LENGTH: 7
<212> TYPE: PRT
<213> ORGANISM: Homo sapiens

<400> SEQUENCE: 200

Ile Met Gln Ile His Ser Arg
1               5

<210> SEQ ID NO 201
<211> LENGTH: 14
<212> TYPE: PRT
<213> ORGANISM: Homo sapiens

<400> SEQUENCE: 201

Met Asn Val Ser Pro Asp Val Asn Tyr Glu Glu Leu Ala Arg
1               5                   10

<210> SEQ ID NO 202
<211> LENGTH: 6
<212> TYPE: PRT
<213> ORGANISM: Homo sapiens

<400> SEQUENCE: 202

Ile Ile Asp Ser Ala Arg
1               5

<210> SEQ ID NO 203
<211> LENGTH: 11
<212> TYPE: PRT
<213> ORGANISM: Homo sapiens

<400> SEQUENCE: 203
```

Ser Ala Tyr Gln Glu Ala Met Asp Ile Ser Lys
1               5                   10

<210> SEQ ID NO 204
<211> LENGTH: 14
<212> TYPE: PRT
<213> ORGANISM: Homo sapiens

<400> SEQUENCE: 204

Ser Asn Glu Glu Gly Ser Glu Glu Lys Gly Pro Glu Val Arg
1               5                   10

<210> SEQ ID NO 205
<211> LENGTH: 22
<212> TYPE: PRT
<213> ORGANISM: Homo sapiens

<400> SEQUENCE: 205

Val Glu Thr Glu Leu Gln Gly Val Cys Asp Thr Val Leu Gly Leu Leu
1               5                   10                  15

Asp Ser His Leu Ile Lys
            20

<210> SEQ ID NO 206
<211> LENGTH: 8
<212> TYPE: PRT
<213> ORGANISM: Homo sapiens

<400> SEQUENCE: 206

Val Leu Ser Ser Ile Glu Gln Lys
1               5

<210> SEQ ID NO 207
<211> LENGTH: 11
<212> TYPE: PRT
<213> ORGANISM: Homo sapiens

<400> SEQUENCE: 207

Tyr Leu Ala Glu Val Ala Thr Gly Asp Asp Lys
1               5                   10

<210> SEQ ID NO 208
<211> LENGTH: 12
<212> TYPE: PRT
<213> ORGANISM: Homo sapiens

<400> SEQUENCE: 208

Tyr Leu Ala Glu Val Ala Thr Gly Asp Asp Lys Lys
1               5                   10

<210> SEQ ID NO 209
<211> LENGTH: 15
<212> TYPE: PRT
<213> ORGANISM: Homo sapiens

<400> SEQUENCE: 209

Ala Asp Val Ile Gln Ala Thr Gly Asp Ala Ile Cys Ile Phe Arg
1               5                   10                  15

<210> SEQ ID NO 210
<211> LENGTH: 8
<212> TYPE: PRT
<213> ORGANISM: Homo sapiens -continued

```
<400> SEQUENCE: 210

Glu Leu Gln Cys Leu Thr Pro Arg
1               5

<210> SEQ ID NO 211
<211> LENGTH: 8
<212> TYPE: PRT
<213> ORGANISM: Homo sapiens

<400> SEQUENCE: 211

Ile Pro Tyr Thr Thr Val Leu Arg
1               5

<210> SEQ ID NO 212
<211> LENGTH: 7
<212> TYPE: PRT
<213> ORGANISM: Homo sapiens

<400> SEQUENCE: 212

Leu Phe Leu Leu Pro His Lys
1               5

<210> SEQ ID NO 213
<211> LENGTH: 10
<212> TYPE: PRT
<213> ORGANISM: Homo sapiens

<400> SEQUENCE: 213

Ala Val Asn Asn Ser Asn Tyr Gly Trp Arg
1               5                   10

<210> SEQ ID NO 214
<211> LENGTH: 13
<212> TYPE: PRT
<213> ORGANISM: Homo sapiens

<400> SEQUENCE: 214

Leu Trp Asn Leu Cys Pro Asp Asn Met Glu Ala Cys Lys
1               5                   10

<210> SEQ ID NO 215
<211> LENGTH: 12
<212> TYPE: PRT
<213> ORGANISM: Homo sapiens

<400> SEQUENCE: 215

Ser Leu Pro Glu Tyr Leu Glu Asn Met Val Ile Lys
1               5                   10

<210> SEQ ID NO 216
<211> LENGTH: 15
<212> TYPE: PRT
<213> ORGANISM: Homo sapiens

<400> SEQUENCE: 216

Thr Gly Glu Asp Glu Asp Glu Asp Asn Asp Ala Leu Leu Lys
1               5                   10                  15

<210> SEQ ID NO 217
<211> LENGTH: 7
<212> TYPE: PRT
<213> ORGANISM: Homo sapiens

<400> SEQUENCE: 217
```

```
Ile Thr Glu Leu Gln Leu Lys
1               5
```

<210> SEQ ID NO 218
<211> LENGTH: 12
<212> TYPE: PRT
<213> ORGANISM: Homo sapiens

<400> SEQUENCE: 218

```
Leu Glu Ser Ala Leu Thr Glu Leu Glu Gln Leu Arg
1               5                   10
```

<210> SEQ ID NO 219
<211> LENGTH: 13
<212> TYPE: PRT
<213> ORGANISM: Homo sapiens

<400> SEQUENCE: 219

```
Leu Glu Ser Ala Leu Thr Glu Leu Glu Gln Leu Arg Lys
1               5                   10
```

<210> SEQ ID NO 220
<211> LENGTH: 11
<212> TYPE: PRT
<213> ORGANISM: Homo sapiens

<400> SEQUENCE: 220

```
Asn Ile Glu Glu Leu Gln Gln Gln Asn Gln Arg
1               5                   10
```

<210> SEQ ID NO 221
<211> LENGTH: 12
<212> TYPE: PRT
<213> ORGANISM: Homo sapiens

<400> SEQUENCE: 221

```
Gln His Gln Met Gln Leu Val Asp Ser Ile Val Arg
1               5                   10
```

<210> SEQ ID NO 222
<211> LENGTH: 12
<212> TYPE: PRT
<213> ORGANISM: Homo sapiens

<400> SEQUENCE: 222

```
Ala Asp Leu Thr Glu Tyr Leu Ser Thr His Tyr Lys
1               5                   10
```

<210> SEQ ID NO 223
<211> LENGTH: 20
<212> TYPE: PRT
<213> ORGANISM: Homo sapiens

<400> SEQUENCE: 223

```
Met Val Leu Ala Ala Ala Gly Gly Val Glu His Gln Gln Leu Leu Asp
1               5                   10                  15

Leu Ala Gln Lys
            20
```

<210> SEQ ID NO 224
<211> LENGTH: 8
<212> TYPE: PRT
<213> ORGANISM: Homo sapiens

<400> SEQUENCE: 224

Asp His Phe Glu Glu Ala Met Arg
1               5

<210> SEQ ID NO 225
<211> LENGTH: 8
<212> TYPE: PRT
<213> ORGANISM: Homo sapiens

<400> SEQUENCE: 225

Glu Ser Ile Glu Ser Glu Ile Arg
1               5

<210> SEQ ID NO 226
<211> LENGTH: 6
<212> TYPE: PRT
<213> ORGANISM: Homo sapiens

<400> SEQUENCE: 226

Gly Phe Gly Ser Phe Arg
1               5

<210> SEQ ID NO 227
<211> LENGTH: 13
<212> TYPE: PRT
<213> ORGANISM: Homo sapiens

<400> SEQUENCE: 227

Lys Tyr Glu Met Phe Ala Gln Thr Leu Gln Gln Ser Arg
1               5                   10

<210> SEQ ID NO 228
<211> LENGTH: 16
<212> TYPE: PRT
<213> ORGANISM: Homo sapiens

<400> SEQUENCE: 228

Met Thr Asn Gly Phe Ser Gly Ala Asp Leu Thr Glu Ile Cys Gln Arg
1               5                   10                  15

<210> SEQ ID NO 229
<211> LENGTH: 19
<212> TYPE: PRT
<213> ORGANISM: Homo sapiens

<400> SEQUENCE: 229

Gln Thr Asn Pro Ser Ala Met Glu Val Glu Glu Asp Asp Pro Val Pro
1               5                   10                  15

Glu Ile Arg

<210> SEQ ID NO 230
<211> LENGTH: 9
<212> TYPE: PRT
<213> ORGANISM: Homo sapiens

<400> SEQUENCE: 230

Arg Asp His Phe Glu Glu Ala Met Arg
1               5

<210> SEQ ID NO 231
<211> LENGTH: 8
<212> TYPE: PRT
<213> ORGANISM: Homo sapiens

<400> SEQUENCE: 231

```
Ser Val Ser Asp Asn Asp Ile Arg
1               5
```

<210> SEQ ID NO 232
<211> LENGTH: 12
<212> TYPE: PRT
<213> ORGANISM: Homo sapiens

<400> SEQUENCE: 232

```
Tyr Glu Met Phe Ala Gln Thr Leu Gln Gln Ser Arg
1               5                   10
```

<210> SEQ ID NO 233
<211> LENGTH: 9
<212> TYPE: PRT
<213> ORGANISM: Homo sapiens

<400> SEQUENCE: 233

```
Asp Asn Leu Ala Glu Asp Ile Met Arg
1               5
```

<210> SEQ ID NO 234
<211> LENGTH: 11
<212> TYPE: PRT
<213> ORGANISM: Homo sapiens

<400> SEQUENCE: 234

```
Glu Glu Ala Glu Asn Thr Leu Gln Ser Phe Arg
1               5                   10
```

<210> SEQ ID NO 235
<211> LENGTH: 10
<212> TYPE: PRT
<213> ORGANISM: Homo sapiens

<400> SEQUENCE: 235

```
Glu Lys Leu Gln Glu Glu Met Leu Gln Arg
1               5                   10
```

<210> SEQ ID NO 236
<211> LENGTH: 10
<212> TYPE: PRT
<213> ORGANISM: Homo sapiens

<400> SEQUENCE: 236

```
Ile Leu Leu Ala Glu Leu Glu Gln Leu Lys
1               5                   10
```

<210> SEQ ID NO 237
<211> LENGTH: 14
<212> TYPE: PRT
<213> ORGANISM: Homo sapiens

<400> SEQUENCE: 237

```
Ile Leu Leu Ala Glu Leu Glu Gln Leu Lys Gly Gln Gly Lys
1               5                   10
```

<210> SEQ ID NO 238
<211> LENGTH: 10
<212> TYPE: PRT
<213> ORGANISM: Homo sapiens

<400> SEQUENCE: 238

```
Leu Gly Asp Leu Tyr Glu Glu Glu Met Arg
```

-continued

```
1               5                   10

<210> SEQ ID NO 239
<211> LENGTH: 8
<212> TYPE: PRT
<213> ORGANISM: Homo sapiens

<400> SEQUENCE: 239

Leu Gln Glu Glu Met Leu Gln Arg
1               5

<210> SEQ ID NO 240
<211> LENGTH: 10
<212> TYPE: PRT
<213> ORGANISM: Homo sapiens

<400> SEQUENCE: 240

Gln Asp Val Asp Asn Ala Ser Leu Ala Arg
1               5                   10

<210> SEQ ID NO 241
<211> LENGTH: 9
<212> TYPE: PRT
<213> ORGANISM: Homo sapiens

<400> SEQUENCE: 241

Gln Val Asp Gln Leu Thr Asn Asp Lys
1               5

<210> SEQ ID NO 242
<211> LENGTH: 10
<212> TYPE: PRT
<213> ORGANISM: Homo sapiens

<400> SEQUENCE: 242

Arg Gln Val Asp Gln Leu Thr Asn Asp Lys
1               5                   10

<210> SEQ ID NO 243
<211> LENGTH: 14
<212> TYPE: PRT
<213> ORGANISM: Homo sapiens

<400> SEQUENCE: 243

Val Glu Val Glu Arg Asp Asn Leu Ala Glu Asp Ile Met Arg
1               5                   10

<210> SEQ ID NO 244
<211> LENGTH: 18
<212> TYPE: PRT
<213> ORGANISM: Homo sapiens

<400> SEQUENCE: 244

Glu Gly Asn Thr Thr Glu Asp Asp Phe Pro Ser Ser Pro Gly Asn Gly
1               5                   10                  15

Asn Lys

<210> SEQ ID NO 245
<211> LENGTH: 12
<212> TYPE: PRT
<213> ORGANISM: Homo sapiens

<400> SEQUENCE: 245

Leu Thr Asn Gly Pro Ser Asn Gly Ser Ser Ser Arg
```

```
1               5                   10
```

<210> SEQ ID NO 246
<211> LENGTH: 20
<212> TYPE: PRT
<213> ORGANISM: Homo sapiens

<400> SEQUENCE: 246

```
Gln Gln Leu Ala Gln Tyr Gln Gln Gln Ser Gln Ala Ser Ala Pro
1               5                   10                  15

Ser Thr Ser Arg
            20
```

<210> SEQ ID NO 247
<211> LENGTH: 8
<212> TYPE: PRT
<213> ORGANISM: Homo sapiens

<400> SEQUENCE: 247

```
Thr Ser Gly Ser Gly Phe His Arg
1               5
```

<210> SEQ ID NO 248
<211> LENGTH: 24
<212> TYPE: PRT
<213> ORGANISM: Homo sapiens

<400> SEQUENCE: 248

```
Glu Lys Val Glu Thr Glu Leu Gln Gly Val Cys Asp Thr Val Leu Gly
1               5                   10                  15

Leu Leu Asp Ser His Leu Ile Lys
            20
```

<210> SEQ ID NO 249
<211> LENGTH: 9
<212> TYPE: PRT
<213> ORGANISM: Homo sapiens

<400> SEQUENCE: 249

```
Ser Asn Glu Glu Gly Ser Glu Glu Lys
1               5
```

<210> SEQ ID NO 250
<211> LENGTH: 8
<212> TYPE: PRT
<213> ORGANISM: Homo sapiens

<400> SEQUENCE: 250

```
His Phe Glu Gln Ala Ile Glu Arg
1               5
```

<210> SEQ ID NO 251
<211> LENGTH: 26
<212> TYPE: PRT
<213> ORGANISM: Homo sapiens

<400> SEQUENCE: 251

```
Leu Ala Ser Leu Thr Pro Gly Phe Ser Gly Ala Asp Val Ala Asn Val
1               5                   10                  15

Cys Asn Glu Ala Ala Leu Ile Ala Ala Arg
            20                  25
```

<210> SEQ ID NO 252

```
<211> LENGTH: 24
<212> TYPE: PRT
<213> ORGANISM: Homo sapiens

<400> SEQUENCE: 252

Thr Val Ala Tyr His Glu Ala Gly His Ala Val Ala Gly Trp Tyr Leu
1               5                   10                  15

Glu His Ala Asp Pro Leu Leu Lys
            20

<210> SEQ ID NO 253
<211> LENGTH: 11
<212> TYPE: PRT
<213> ORGANISM: Homo sapiens

<400> SEQUENCE: 253

Leu Phe Tyr Ser Thr Phe Ala Thr Asp Asp Arg
1               5                   10

<210> SEQ ID NO 254
<211> LENGTH: 11
<212> TYPE: PRT
<213> ORGANISM: Homo sapiens

<400> SEQUENCE: 254

Lys Leu Pro Ile Gln Glu Phe His Leu Ser Arg
1               5                   10

<210> SEQ ID NO 255
<211> LENGTH: 7
<212> TYPE: PRT
<213> ORGANISM: Homo sapiens

<400> SEQUENCE: 255

Leu Phe Val Glu Thr Gly Lys
1               5

<210> SEQ ID NO 256
<211> LENGTH: 9
<212> TYPE: PRT
<213> ORGANISM: Homo sapiens

<400> SEQUENCE: 256

Leu Val Phe Gly Phe Leu Asn Gly Arg
1               5

<210> SEQ ID NO 257
<211> LENGTH: 28
<212> TYPE: PRT
<213> ORGANISM: Homo sapiens

<400> SEQUENCE: 257

Ile Leu Leu Ser Gln Thr Thr Gly Val Ala Ile Pro Leu His Ala Ser
1               5                   10                  15

Ser Leu Asp Asp Val Ser Leu Ala Ser Thr Pro Lys
            20                  25

<210> SEQ ID NO 258
<211> LENGTH: 29
<212> TYPE: PRT
<213> ORGANISM: Homo sapiens

<400> SEQUENCE: 258
```

```
Asp Val Val Phe Asn Tyr Leu His Ala Thr Ala Phe Gln Gly Thr Pro
1               5                   10                  15

Leu Ala Gln Ala Val Glu Gly Pro Ser Glu Asn Val Arg
            20              25
```

US 9,063,149 B2

QUANTITATIVE STANDARD FOR MASS SPECTROMETRY OF PROTEINS

CROSS REFERENCE TO RELATED APPLICATIONS

This application is a 35 U.S.C. §371 U.S. National Stage Entry of International Application No. PCT/EP2012/056234 filed Apr. 4, 2012, which claims the benefit of priority of European Application No.: 11002794.3 filed Apr. 4, 2011, U.S. Provisional Application No.: 61/471,528, filed Apr. 4, 2011 and U.S. Provisional Application No.: 61/471,534, filed Apr. 4, 2011, the contents of which are each incorporated herein by reference in its entirety.

REFERENCE TO SEQUENCE LISTING

The present application is being filed along with a Sequence Listing in electronic format. The sequence Listing filed, entitled 20071011SEQLSTREV, was created on Sep. 19, 2014 and is 53,202 bytes in size. The information in electronic format of the Sequence Listing is incorporated herein by reference in its entirety.

FIELD OF THE INVENTION

This invention relates to a method of determining the absolute amount of a target polypeptide in a sample, said method comprising the following steps: (a) adding (aa) a fusion polypeptide to said sample, said fusion polypeptide comprising (i) at least one tag sequence and (ii) a subsequence of the target polypeptide; and (ab) a known absolute amount of a tag polypeptide comprising or consisting of said tag sequence according to (aa) to said sample, wherein said fusion polypeptide on the one hand is mass-altered as compared to said target polypeptide and said tag polypeptide on the other hand, for example, said fusion polypeptide on the one hand and said target polypeptide and said tag polypeptide on the other hand are differently isotope labeled; (b) performing a proteolytic digestion of the mixture obtained in step (a); (c) subjecting the result of the proteolytic digestion of step (b), optionally after chromatography, to mass spectrometric analysis; and (d) determining the absolute amount of said target polypeptide from (i) the peak intensities in the mass spectrum acquired in step (c) of said fusion polypeptide, said tag polypeptide and said target polypeptide and (ii) said known absolute amount of said tag polypeptide.

BACKGROUND OF THE INVENTION

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Mass spectrometry (MS)-based proteomics has become a method of choice to study proteins in a global manner (1-3). Mass spectrometry is not inherently quantitative but methods have been developed to address this limitation to a certain extent. Most of them are based on stable isotopes and introduce a mass shifted version of the peptides of interest, which are then quantified by their 'heavy' to 'light' ratio. Stable isotope labeling is either accomplished by chemical addition of labeled reagents, enzymatic isotope labeling or metabolic labeling (4-6). Generally, these approaches are used to obtain relative quantitative information on proteome expression levels in a light and a heavy labeled sample. For example, stable isotope labeling by amino acids in cell culture SILAC (7, 8) is performed by metabolic incorporation of differently labeled, such as light or heavy labeled amino acids into the proteome. Labeled proteomes can also be used as internal standards for determining protein levels of a cell or tissue proteome of interest, such as in the spike-in SILAC approach (9).

Absolute quantification is technically more challenging than relative quantification and could so far only be performed accurately for a single or a small number of proteins at a time (10). Typical applications of absolute quantifications are the determination of cellular copy numbers of proteins (important for systems biology) or the concentration of biomarkers in body fluids (important for medical applications). Furthermore, any precise method of absolute quantification, when performed in more than one sample, also yields the relative amounts of the protein between these samples.

Several methods for absolute quantification have emerged over the last years including AQUA (11), QConCAT (12, 13), PSAQ (14), absolute SILAC (15) and FlexiQuant (16). They all quantify the endogenous protein of interest by the heavy to light ratios to a defined amount of the labeled counterpart spiked into the sample and are primarily distinguished from each other by either spiking in heavy labeled peptides or heavy labeled full length proteins. The AQUA strategy uses proteotypic peptides (17) which are chemically synthesized with heavy isotopes and spiked in after sample preparation. AQUA peptides are commercially available but expensive, especially when many peptides or proteins need to be quantified (see, for example, Kettenbach et al., Nat. Protoc. 2011, 6:175-86). Moreover, the AQUA strategy suffers from quantification uncertainties that are introduced due to spiking in of the peptide standard after sample preparation and enzymatic proteolysis, which is a late stage in the workflow. Furthermore, any losses of the peptides—for example during storage—would directly influence quantification results. The QconCAT approach is based on artificial proteins that are a concatamers of proteotypic peptides. This artificial protein is recombinantly expressed in *Escherichia coli* and spiked into the sample before proteolysis. QconCAT allows production of labeled peptides, but does not correct any bias arising from protein fractionation effects or digestion efficiency. The PSAQ, absolute SILAC and FlexiQuant approaches try to address these limitations by metabolically labeling full length proteins by heavy versions of the amino acids arginine and lysine. PSAQ and FlexiQuant synthesize full-length proteins in vitro in wheat germ extracts or in bacterial cell extract, respectively, whereas absolute SILAC was described with recombinant protein expression in *E. coli*. The protein standard is added at an early stage, such as directly to cell lysate. Consequently, sample fractionation can be performed in parallel and the SILAC protein is digested together with the proteome under investigation. However, these advantages come at the cost of having to produce full length proteins, which limits throughput and generally restricts these methods to soluble proteins.

Accordingly, there is an unmet need for improved or alternative means and methods of mass spectrometry-based absolute quantitation of peptides and polypeptides.

DETAILED DESCRIPTION

The present invention provides a method of determining the absolute amount of a target polypeptide in a sample, said method comprising the following steps: (a) adding (aa) a fusion polypeptide to said sample, said fusion polypeptide comprising (i) at least one tag sequence and (ii) a subsequence of the target polypeptide; and (ab) a known absolute amount of a tag polypeptide comprising or consisting of said tag sequence according to (aa) to said sample, wherein said fusion polypeptide on the one hand is mass-altered as compared to said target polypeptide and said tag polypeptide on the other hand, for example, said fusion polypeptide on the one hand and said target polypeptide and said tag polypeptide on the other hand are differently isotope labeled; (b) performing proteolytic digestion of the mixture obtained in step (a); (c) subjecting the result of proteolytic digestion of step (b), optionally after chromatography, to mass spectrometric analysis; and (d) determining the absolute amount of said target polypeptide from (i) the peak intensities in the mass spectrum acquired in step (c) of said fusion polypeptide, said tag polypeptide and said target polypeptide and (ii) said known absolute amount of said tag polypeptide.

The term "absolute amount" has its usual meaning and is to be held distinct from relative amounts, i.e. ratios, as they are commonly determined in expression analysis, be it by mRNA expression profiling or proteomics methods. In particular, it is understood that the term "absolute amount" refers to the copy number or the amount of substance of a given protein or polypeptide in, for example, a cell, or the amount in a defined volume, or in a sample such as ng/mL of a body fluid such as urine or plasma. In other words, said absolute amount may be expressed in terms of a concentration, a mass or amount of substance (in moles or number of molecules).

The term "polypeptide" is well established in the art and refers to a polycondensate of amino acids, preferably of the 20 standard amino acids. It is understood that the term "polypeptide" as used herein embraces also peptides, wherein peptides have a minimal length of two amino acids. On the other hand, the term "polypeptide" includes proteins, at least to the extent such proteins consist of a single chain. Proteins in turn may also comprise more than one polypeptide chain.

It is understood that the methods according to the invention are equally suitable to determine the absolute amounts of proteins, also to the extent proteins comprise more than one polypeptide chain. In such a case, and assuming the molar ratios of the polypeptide chains comprised in the protein are known, it may be sufficient to determine the absolute amount of one polypeptide comprised in the protein of interest. Alternatively, the absolute amount of more than one or all polypeptides comprised in the protein of interest may be determined by the methods according to the invention.

A "fusion polypeptide" according to the invention is a polypeptide which comprises at least two segments of different origin. More specifically, a fusion polypeptide according to the invention requires presence of a tag amino acid sequence and a subsequence of the target polypeptide comprised or suspected to be comprised in the recited sample. It is deliberately envisaged that more than one tag amino acid sequence is present. This is the subject of preferred embodiments discussed further below. Furthermore, this is exemplified in the enclosed examples and depicted in FIG. 1. Preferred embodiments of the fusion polypeptides are described further below and include protein epitope signature tags (PrESTs). It is preferred that said tag sequence is chosen such that proteolytic digestion of the target proteome on the one hand and of the tag sequence on the other hand yield two disjunct sets of peptides or at least two sets of peptides which overlap by less than 25%, less than 10%, less than 5%, less than 2% or less than 1%. A "target proteome" is typically a proteome originating from a single species. A target proteome comprises said target polypeptides. A preferred proteome is a human proteome. If more than one tag sequence is present, it is understood that the tag sequences are different from each other. In particular, the set of peptides obtained by proteolytic digestion of a first tag sequence present in said fusion polypeptide and the set of peptides obtained by proteolytic digestion of a second tag sequence (and also any further tag sequence) present in said fusion polypeptide are disjunct, i.e., they do not a share a peptide of same sequence. Whenever reference is herein made to disjunct sets of peptides obtained by proteolytic digestion, it is understood that the sets of peptides are in particular disjunct as regards peptides of or above a minimal length, said minimal length being at least 4, 5, 6, 7, 8 or 9 amino acids.

The term "subsequence" in its broadest form refers to any partial sequence of a target polypeptide to be detected and furthermore includes the entire sequence of said target polypeptide. In a preferred embodiment, said subsequence is a partial sequence of the target polypeptide, the entire sequence of said target polypeptide being excluded. Preferred length ranges of said subsequence are discussed further below.

The term "isotope" refers to two or more nuclides with the same number of protons (atomic number) but different numbers of neutrons. Such difference in mass number provides for different peak positions of an isotope labeled compound or fragment on the one hand and its unlabeled counterpart on the other hand in a mass spectrum. Preferred isotopes are deuterium, 13C and 15N.

The term "labeled" refers to a frequency of isotopes which deviates from the naturally occurring frequency. In preferred embodiments, the term "isotope labeled" refers to a compound, moiety, fragment or molecule which, to the extent atoms with the same atomic number are considered, exclusively contains a given isotope. For example, a preferred isotope labeled lysine has 13C nuclides at all carbon positions. In preferred embodiments, one or more specific amino acids, such as all lysines and/or all arginines, are isotope labeled. Suitable isotope labeled amino acid residues are listed further below.

The term "differently labeled" or "differently isotope labeled" as used herein refers to a plurality of labeling schemes. In particular, it is sufficient for two polypeptides to be differently labeled, if one of them is labeled and the other one is not. Equally envisaged is that one of the polypeptides is isotope labeled in one specific way, whereas the other polypeptide is isotope labeled as well, but in a different way, the consequence being that both polypeptides do not exhibit the naturally occurring frequency of isotopes and can be distinguished in the mass spectrum. It is understood that "differently isotope labeled" according to the invention is such that, upon proteolytic digestion, (i) at least a first peptide is formed from the target polypeptide and at least a second peptide is formed from the subsequence thereof as comprised in the fusion polypeptide such that the first and second peptide are identical in sequence but differ in their mass, and (ii) at least a third peptide is formed from the tag polypeptide and at least a fourth peptide is formed from the tag sequence as comprised in the fusion polypeptide such that the third and fourth peptide are identical in sequence but differ in their mass. This can be achieved, for example, by the labeled polypeptides comprising internal labels, preferably each occurrence of one or more given amino acids being labeled, said given amino acids being preferably those which are comprised in the cleavage site recognized by the enzyme used for proteolytic digestion. Such preferred amino acids are, as described elsewhere herein, lysine and/or arginine. Taken together, it is preferred that said fusion polypeptide on the one hand and said target polypeptide and said tag polypeptide on the other hand are differently internally isotope labeled. The term "internal" as used herein in relation to labels is understood to distinguish from terminal labels.

Generally speaking, whenever reference is made to "differently labeled" or "differently isotope labeled" in the present disclosure, it is understood that these terms relate to a preferred embodiment. More generally, any means of mass-alteration including, though not confined to isotope labeling is envisaged. The terms "mass-alteration" and "mass-altered" as used herein refer to all those means and methods which provide for peptides (or polypeptides) obtained from different sources and identical in sequence to differ with regard to their mass. Isotope labeling is one preferred means of achieving this goal. An alternative method known in the art is the use of isobaric tags for relative and absolute quantitation (iTRAQ). This method uses isotope-coded covalent tags; see, for example, Ross et al., Mol. Cell. Proteomics 3, 1154-69, 2004. Preferably, iTRAQ is based on a covalent labeling of the N-terminus and sidechain amines of peptides and polypeptides. Suitable agents are known in the art, examples of which include agents referred to as 4-plex and 8-plex. If it is stated herein that an entity A is mass-altered as compared to an entity B, it is understood that either entity A or entity B deviates from the naturally occurring form, for example by different isotope labeling or owing to the presence covalent tags in the sense of iTRAQ.

Turning to the requirement as recited in the main embodiment that "at least said fusion polypeptide on the one hand and said target polypeptide and said tag polypeptide on the other hand are differently isotope labeled", it is noted that said target polypeptide and said tag polypeptide may be isotope labeled in the same way or according to different labeling patterns, or, if said fusion polypeptide is isotope labeled, both may be unlabeled. More specifically, at least the following labeling schemes are embraced. (1) Said fusion polypeptide is isotope labeled, and both said target polypeptide and said tag polypeptide are not isotope labeled, (2) said target polypeptide and said tag polypeptide are isotope labeled, and said fusion polypeptide is not isotope labeled, wherein target polypeptide and tag polypeptide are isotope labeled in the same way or according to different labeling patterns, (3) a polypeptide selected from target polypeptide, fusion polypeptide and tag polypeptide is not isotope labeled or isotope labeled according to a first pattern, a second polypeptide chosen from the same group is isotope labeled according to a second pattern, and the remaining polypeptide from the group is isotope labeled according to a third pattern. The three patterns (or two patterns in case one of the polypeptides is not isotope labeled) according to labeling scheme (3) may be implemented, for example, by using two or three isotope labeled forms of one or more given amino acids, said two or three isotope labeled forms differing in the total mass. An exemplary labeling scheme according to (3) is as follows: the target polypeptide is not isotope labeled, the fusion polypeptide is isotope labeled ("heavy weight" form), and the tag polypeptide is isotope labeled according to a different pattern such that it is provided, for example, either in a "middle weight" or an "extra heavy weight" form. Such a labeling scheme may be particularly preferred if it is suspected that a proteolytic product of the tag polypeptide could also be derived from the digestion of the sample, e.g. if the sample is human and the tag is a human protein or a domain or segment thereof.

The term "labeling scheme" as used herein distinguishes between different polypeptides. For a given labeling scheme, a class of polypeptides (classes being target polypeptides, tag polypeptides, and fusion polypeptides) is labeled in the same way, for example by incorporation of a 13C labeled lysine at all positions where a lysine occurs. A labeling scheme provides for different classes being differently labeled. On the other hand, the term "labeling pattern" distinguishes between differently labeled forms of a given peptide. For example, a specific polypeptide may be labeled by replacing all occurrences of lysine with 13C labeled lysine or by replacing all positions of arginine with 13C 15N labeled arginine, thereby rendering the labeling patterns differently.

Various means for isotope labeling are at the skilled person's disposal and include chemical addition of labeled reagents, enzymatic isotope labeling or metabolic labeling (4-6).

According to the invention it is preferred that the isotope labeling is introduced by metabolic labeling. In other words, the polypeptides to be used in the methods according to the invention, to the extent they are required to be labeled, are preferably obtained by means of production in biological systems, such as cell-free as well as cellular systems. For example, a host cell may be used which is auxotrophic for lysine and/or arginine, wherein at the same time isotope labeled lysine and/or arginine is provided in the growth medium. A preferred means of metabolic isotope labeling is stable isotope labeling with amino acids in cell culture (SILAC). SILAC procedures are known in the art and described in the background section herein above as well as in the references cited in relation thereto which are herewith incorporated by reference. As mentioned above, to the extent isotope labeling makes use of isotopes with higher mass numbers, the labeled form is commonly referred to as "heavy" form, whereas the naturally occurring counterpart or the counterpart which is free or essentially free of the heavy isotope under consideration is commonly referred to as "light" form.

The recited "known absolute amount of a tag polypeptide" may be determined with methods established in the art. A preferred method is amino acid analysis. Amino acid analysis is typically provided as a service by a variety of companies. The method preferably includes the total hydrolysis of a given sample, the chemical derivatization of the obtained free amino acids, the separation of the derivatized amino acids, for example by reversed phase HPLC, and the subsequent interpretation of the result. The method is described in more detail in, for example, in Moore and Stein, J. Biol. Chem. 176, 367-388 (1948) as well as in Moore and Stein, J. Biol. Chem. 176, 337-365 (1948).

The methods according to the invention require, on the one hand, that a first subsequence of the fusion polypeptide is identical to a subsequence of the target protein, and on the other hand, that a second subsequence of the fusion polypeptide is identical to the tag polypeptide. Furthermore, even though the amino acid sequences are identical, the masses of the first subsequence of the fusion polypeptide and its counterpart in the target polypeptide need to be distinct. Likewise, the masses of the second sequence of the fusion polypeptide and the tag polypeptide also need to be distinct. This may be achieved by the labeling schemes described above. This allows for quantitative comparisons to be made between the tag sequence within the fusion polypeptide and the tag polypeptide as well as between said subsequence comprised in said fusion polypeptide and the target polypeptide polypeptide.

Step (b) provides for proteolytic digestion that, as is well established in the art, gives rise to fragments which can conveniently be handled in mass spectroscopy. Preferred enzymes to be used for proteolytic digestion are described further below. It is preferred that said proteolytic digestion is specific, i.e., that cleavage occurs at all cleavage sites of the enzyme used. On the other hand, and as described herein, the methods of the present invention provide for the avoidance of bias introduced by incomplete digestion.

Subsequent to proteolytic digestion, mass spectrometry analysis is performed. Ionized peptide molecules are transferred into the vacuum systems of the mass spectrometer. In a preferred mode of operation, widely known to the practitioners of the art, the mass spectrometer is operated so as to perform a mass spectrometric scan that records a mass spectrum of the peptides entering the instrument at that time. Quantification is based on the peaks present in this mass spectrometric (or MS) scan. The enclosed examples provide a more detailed account of suitable modes of operation of the mass spectrometer. Depending on the nature of the samples to be analyzed, the polypeptides suspected to be comprised in the sample and the available instrumentation, the skilled person can choose suitable modes of operation.

Given that proteolytic digestion is performed, the tag polypeptide comprising said tag sequence according to (aa) or a tag polypeptide consisting of said tag sequence according to (aa) may be used interchangeably. Preferably, in either case the same one or more tag fragments will be yielded during proteolytic digestion.

Prior to performing mass spectrometry analysis, the result of proteolytic digestion may be subjected to chromatography as is established in the art. Preferred means of chromatography are liquid chromatography (LC). In a preferred mode of operation, the peptide mixture is injected onto a liquid chromatographic column, separated by a gradient of organic solvent lasting several minutes or several hours and on-line electrosprayed.

Step (d) combines the information obtained in the mass spectrum (which can be viewed as relative intensities) with the known absolute amount of the tag polypeptide in order to determine absolute amounts, in particular the absolute amount of the target polypeptide comprised in the sample. To explain further, and using the terminology of first to fourth peptides introduced herein above, the absolute amount of a given target polypeptide may be determined, for example, as follows. Ratios of amounts of substance are identical to ratios of intensities in the MS spectrum of the corresponding peaks. Using the numbers from 1 to 4 as short hand designations of first to fourth peptide, the following applies. The amount of substance of the fourth peptide (proteolytic fragment derived from the tag sequence as comprised in the fusion polypeptide) $N(4)$ can be determined according to $N(4)=N(3)$ times $I(4)/I(3)$. $N(3)$ is the known absolute amount of the tag polypeptide. $I(3)$ and $I(4)$ are the corresponding peak intensities. Given the definition of the fusion polypeptide, $N(2)=N(4)$ applies, i.e. the amounts of substance of the peptides formed from either part of the fusion polypeptide are identical. The amount of substance of the target polypeptide $N(1)$ can then be determined as follows: $N(1)=N(2)$ times $I(1)/I(2)$. Making use of $N(2)=N(4)$ and $N(4)=N(3)$ times $I(4)/I(3)$, it follows that $N(1)=N(3) [I(1) I(4)/I(2) I(3)]$ which permits absolute quantitation of the target polypeptides based on peak intensities $I(1)$ to $I(4)$ and the known absolute amount of the tag polypeptide $N(3)$. Note that in practice the ratios are usually determined as the mean of the ratios of several peptide intensities; i.e. more than one peptide pair covering the tag sequence and the target polypeptide sequence.

The methods according to the invention make use of specific labeling schemes of three distinct species, the labeling schemes being described above. A key feature of the methods of the invention is the use of fusion polypeptides, said fusion polypeptides containing at least one generic sequence, also referred to as "tag sequence" herein. The concomitant provision of a tag polypeptide as defined above in a known absolute amount permits calibration in a manner which advantageously is independent of the actual polypeptide to be quantitatively determined.

Deviating from a variety of prior art methods as discussed above, the methods of the present invention provide for early adding of the standard (in case of the main embodiment said known absolute amount of a tag polypeptide) in the entire workflow. As a consequence, downstream steps including proteolytic digestion and optionally chromatography is equally applied to both the standard and the constituents of the sample to be analyzed. Any variation in efficiency or performance of, for example proteolytic digestion, will equally affect all constituents of the mixture obtained in step (a), thereby avoiding any bias that could arise therefrom. In a preferred embodiment, no protein size-based methods such as size exclusion chromatography is used after said adding.

It is well known to practitioners of proteomics that accurate quantification of proteins of very low abundance proteins is challenging. However, the accuracy of quantification of the fusion protein standard itself does not depend on the cellular abundance or other attributes of the polypeptide to be determined, noting that the same amount of fusion polypeptide is preferably used in each instance of the methods according to the invention. Also, the purity of a composition comprising said fusion polypeptide to be added has no impact because the methods specifically determine the amount of the fusion polypeptide and not of total protein.

As discussed in more detail in the examples enclosed herewith, the methods according to the present invention provide for significantly improved accuracy in quantitative determination of cellular protein expression levels. Further advantages of the method are that it typically results in several quantifiable peptides for each fusion polypeptide, both for the accurate quantification of the standard and for the target polypeptide to be absolutely quantified. Furthermore, production of the standard can be streamlined because protein expression can be performed in a standard system (such as *E. coli*) and because a large number of fusion polypeptides can be produced under similar conditions as they only differ by a relatively short unique sequence in the preferred embodiment.

In a second aspect, the present invention provides a method of creating a quantitative standard, said method comprising the following steps: (a) providing a plurality of fusion polypeptides, each of said fusion polypeptides comprising (i) at least one tag sequence and (ii) a subsequence of a target polypeptide to be quantitatively determined, wherein all fusion polypeptides share at least one tag sequence, thereby obtaining the standard; (b) determining the absolute amounts of said fusion polypeptides by (ba) adding to one of said fusion polypeptides at a time a known amount of a tag polypeptide comprising or consisting of the tag sequence shared among the fusion polypeptides according to (a), wherein said fusion polypeptide is mass-altered as compared to said tag polypeptide, for example, said fusion polypeptide and said tag polypeptide are differently isotope labeled, (bb) performing proteolytic digestion of the mixture of one fusion polypeptide and said tag polypeptide obtained in step (ba); (bc) subjecting the result of proteolytic digestion of step (bb), optionally after chromatography, to mass spectrometric analysis; and (bd) determining the absolute amount of said one fusion polypeptide from (i) the peak intensities in the mass spectrum of fusion polypeptide and tag polypeptide and (ii) said known amount of said tag polypeptide, thereby obtaining the absolute amount of one of said fusion polypeptides at a time.

While the second aspect provides for the option of multiplexing as discussed further below, it is of note that said second aspect is not confined to the use of a plurality of fusion polypeptides. Accordingly, the present invention also provides a method of creating a quantitative standard, said method comprising the following steps: (a) providing one fusion polypeptide, the one fusion polypeptide comprising (i) at least one tag sequence and (ii) a subsequence of a target polypeptide to be quantitatively determined, thereby obtaining the standard; (b) determining the absolute amount of said fusion polypeptide by (ba) adding to the one fusion polypeptide a known amount of a tag polypeptide comprising or consisting of the tag sequence comprised in the one fusion polypeptide according to (a) wherein said fusion polypeptide is mass-altered as compared to said tag polypeptide, for example, said fusion polypeptide and said tag polypeptide are differently isotope labeled, (bb) performing proteolytic digestion of the mixture of one fusion polypeptide and said tag polypeptide obtained in step (ba); (bc) subjecting of the result of proteolytic digestion of step (bb), optionally after chromatography, to mass spectrometric analysis; and (bd) determining the absolute amount of said one fusion polypeptide from (i) the peak intensities in the mass spectrum of fusion polypeptide and tag polypeptide and (ii) said known amount of said tag polypeptide, thereby obtaining the absolute amount of the one fusion polypeptide.

In other words, part of a fusion polypeptide preparation is combined with a known amount of a tag polypeptide, wherein the fusion polypeptide is mass-altered as compared to the tag polypeptide. This binary mixture is subjected to proteolytic digestion, mass spectrometric analysis and quantitation to provide the absolute amount of the fusion polypeptides part, from which amount the exact concentration of the fusion polypeptide in the preparation can be calculated. Thus, a quantitative standard of a single fusion polypeptide has been provided. Then, at least part of the quantitative standard is added to the sample to be analyzed, after which proteolytic digestion of the obtained mixture is performed. The result of proteolytic digestion is subjected to to mass spectrometric analysis, optionally after chromatography. The absolute amount of the target polypeptide is then determined from (i) the peak intensities in the mass spectrum of the fusion polypeptide and the target polypeptide and (ii) the known absolute amounts of the fusion polypeptide, wherein said fusion polypeptide is mass-altered as compared to said target polypeptide.

Therefore, it is understood that said second aspect, in a more concise form covering both the use of one fusion polypeptide and a plurality thereof, relates to a method of creating a quantitative standard, said method comprising the following steps: (a) providing one or a plurality of fusion polypeptides, the one fusion polypeptide or each of said fusion polypeptides, respectively, comprising (i) at least one tag sequence and (ii) a subsequence of a target polypeptide to be quantitatively determined, wherein, to the extent said plurality of fusion polypeptides is provided, all fusion polypeptides share at least one tag sequence, thereby obtaining the standard; (b) determining the absolute amounts of said fusion polypeptide(s) by (ba) adding to the one fusion polypeptide or to one of said fusion polypeptides at a time, respectively, a known amount of a tag polypeptide comprising or consisting of the tag sequence comprised in the one fusion polypeptide or shared among the fusion polypeptides, respectively, according to (a), wherein said fusion polypeptide is mass-altered as compared to said tag polypeptide, for example, said fusion polypeptide and said tag polypeptide are differently isotope labeled, (bb) performing proteolytic digestion of the mixture of one fusion polypeptide and said tag polypeptide obtained in step (ba); (bc) subjecting of the result of proteolytic digestion of step (bb), optionally after chromatography, to mass spectrometric analysis; and (bd) determining the absolute amount of said one fusion polypeptide from (i) the peak intensities in the mass spectrum of fusion polypeptide and tag polypeptide and (ii) said known amount of said tag polypeptide, thereby obtaining the absolute amount of the one fusion polypeptide or of one of said plurality of fusion polypeptides at a time, respectively.

Related thereto, the present invention in a third aspect provides a method of determining the absolute amount of one or more target polypeptides in a sample, said method comprising the following steps: (a) optionally performing the method according to the second aspect; (b) adding the quantitative standard as defined in the second aspect to said sample; (c) performing proteolytic digestion of the mixture obtained in step (b); (d) subjecting the result of proteolytic digestion of step (c), optionally after chromatography, to mass spectrometric analysis; and (e) determining the absolute amounts of the target polypeptide(s) from (i) the peak intensities in the mass spectrum acquired in step (d) of fusion polypeptide(s) and target polypeptides and (ii) the known absolute amount(s) of said fusion polypeptide(s), wherein said fusion polypeptide(s) is/are mass-altered as compared to said target polypeptide(s), for example, said one or more target polypeptide(s) is/are differently isotope labeled as compared to said fusion polypeptide(s).

While the main embodiment provides for absolute quantitation of one polypeptide from a single mass experiment, the second and third aspects of the present invention relate to (i) preparation and quantitation of a standard and (ii) use of this standard in the quantitation of one or more of a plurality of polypeptides comprised in a sample. Importantly, such an approach is amenable to multiplexing. In other words, not only one, but also a plurality of polypeptides comprised in a sample can be concomitantly determined in a quantitative manner.

According to the second aspect, one or a plurality of fusion polypeptides is provided. According to step (b) of the second aspect, one fusion polypeptide at the time is combined with a known amount of a tag polypeptide. This binary mixture is subjected to proteolytic digestion, mass spectrometric analysis and quantitation to provide the absolute amount of one of said fusion polypeptides at a time. By performing step (b) of the second aspect for the one, more or all of the fusion polypeptides comprised in the standard, the standard is quantitatively characterized and can be used in a method in accordance with the third aspect of the present invention. The method of the second aspect provides in step (a) for the physical manufacture of the quantitative standard, and in step (b) for its characterization in terms of absolute amounts of the constituent fusion polypeptide(s). Preferred quantitative standards are also referred to as "PrEST master mix" herein.

A method according to the third aspect may, according to step (a), incorporate the method of creating a quantitative standard according to the second aspect of the invention in its entirety. Alternatively, step (a) may be omitted. In that case, it is understood that the quantitative standard to be added according to step (b) is characterized in accordance with step (b) of the second aspect.

Accordingly, in one embodiment, the internal standard (i.e. the fusion polypeptide) is thus quantified in a first step using an internal standard of the internal standard (i.e. the tag polypeptide), and a target protein in a sample is quantified in a subsequent second step using the quantified internal standard (i.e. the fusion polypeptide quantified in the first step). In this embodiment, the first step may be carried out at one site, such as at the premises of the company providing quantified fusion polypeptides, while the second step is carried out at another site, such as in a lab where proteins in biological samples are quantified for diagnostic purposes.

As recited in the third aspect, said one or more target polypeptides are mass-altered, preferably differently isotope labeled as compared to said fusion polypeptides. In other words, and in those cases where said fusion polypeptides are not isotope labeled, it is necessary to prepare a sample wherein the one or more target polypeptides comprised in the sample are isotope labeled. On the other hand, a requirement to prepare an isotope labeled sample does not arise for those embodiments falling under the third aspect where said fusion polypeptides are isotope labeled.

In a preferred embodiment, more than one fusion polypeptide comprising different subsequences of a target polypeptide in said sample are used. According to this embodiment, more than one fusion polypeptide is used in the quantitation of one given target polypeptide. This aspect is further described in the examples enclosed herewith and provides for improved accuracy and statistical significance.

In a further preferred embodiment, one or two tags are present in said fusion polypeptides, said tag(s) being selected from a purification tag and a solubility tag. This embodiment embraces the concomitant presence of two different tags. Preferred embodiments of either tag are described further below. It is understood that the solubility tag is preferably used as a quantitation tag ("tag sequence") in accordance with the methods of the present invention.

In a further preferred embodiment of the methods of determining absolute amounts according to the invention, said sample comprises cells and/or body fluids. Said cells may be of various types or of a single type. Moreover, the cells may be embedded in one or more tissues. To the extent human cells are envisaged, it is preferred that such human cell is not obtained from a human embryo, in particular not via methods entailing destruction of a human embryo. On the other hand, human embryonic stem cells are at the skilled person's disposal. Accordingly, the present invention may be worked with human embryonic stem cells without any need to use or destroy a human embryo. The sample may comprise one or more body fluids, said body fluids preferably being selected from blood, blood serum, blood plasma, breast milk, cerebrospinal fluid, mucus, peritoneal fluid, pleural fluid, saliva, semen, sweat, tears, vaginal secretion and urine.

In a further preferred embodiment, said adding is effected prior to proteolytic digestion of the polypeptides. This embodiment relates to those cases where the sample to be analyzed comprises or consists of cells. Said adding refers to the addition of a fusion polypeptide and a tag polypeptide according to the main embodiment, or to adding the quantitative standard according to the third aspect of the invention. In either case, the early adding according to this embodiment provides for the methods to account for any bias possibly introduced by sample preparation and processing, in particular by the enzymatic digestion step. This is a further advantage as compared to those prior art methods which require a late spiking-in of the standard during the workflow.

In a further preferred embodiment, between two and 500 fusion polypeptides are used. As stated above, the second and third aspect of the invention provide for multiplexing. Preferred numbers of fusion polypeptides to be used in each instance of the method are between 2 and 200, such as between 2 and 100, including any integer value embraced by these lower and upper limits such as 50 fusion polypeptides. The examples enclosed herewith provide an account of excellent performance when using 43 fusion polypeptides.

In a further preferred embodiment, a solubility tag is present in each of said fusion polypeptides. A preferred solubility tag consists of the sequence of SEQ ID NO: 1. The sequence of SEQ ID NO: 1 is particularly advantageous in that the sequences obtained by tryptic digestion of the human proteome on the one hand and of the sequence of SEQ ID NO: 1 on the other hand are disjunct. In other words, a tryptic digestion of the sequence of SEQ ID NO: 1 yields peptides none of which is obtained from a tryptic digestion of the human proteome. The same applies at least for the majority of peptides obtained from the sequence of SEQ ID NO: 1 when the other preferred enzymes as disclosed herein are used for proteolytic digestion.

In a further preferred embodiment said subsequence of a polypeptide (a) consists of 15 to 205 amino acids; (b) comprises a proteotypic peptide; and/or (c) is selected to have minimal sequence identity to other proteins, excludes signal peptides and/or excludes sequences from transmembrane spanning regions. The subsequence recited in this embodiment is the subsequence of a target polypeptide as comprised in the fusion polypeptide according to the present invention. Feature (a) provides for a preferred length range of said subsequence. Further preferred lengths and length ranges are disclosed herein, in particular in the description of the fourth aspect of the invention. Such disclosure applies mutatis mutandis to the present preferred embodiment. It is noted that said length range is above the length range observed for tryptic peptides. As consequence, the present invention in this embodiment is distinguished from those prior art methods which make use of, for example, tryptic peptides or other peptides which are not amenable to cleavage by the proteolytic enzyme to be used for proteolytic digestion. Advantageously, and as stated above, subsequences in this length range give rise to a plurality of peptides upon proteolytic digestion, thereby enhancing accuracy of the quantitation.

The term "proteotypic" as used in this specific context refers to peptides which are frequently or always observed in the mass spectrum of a given polypeptide comprising said proteotypic peptide.

According to part (c) of this preferred embodiment, further features are provided which relate to the uniqueness of said subsequence (minimal sequence identity to other proteins, in particular to other proteins from the same proteome) or to easy handling and/or detection (exclusion of signal peptides and transmembrane segments).

In a further preferred embodiment, said known absolute amount of said tag polypeptide is determined by amino acid analysis. Preferred means and methods of amino acid analysis are described herein above.

In a fourth aspect, the present invention provides a fusion polypeptide for the quantification of a target polypeptide by mass spectroscopy, wherein: said fusion polypeptide consists of 35 to 455 amino acid residues and comprises (i) a target region, which is a fragment of the target polypeptide, and (ii) a tag region, which is not a fragment of the target polypeptide, said target region consists of 15 to 205 amino acid residues and comprises at least two signature regions; said tag region consists of 20 to 250 amino acid residues and comprises at least two signature regions; and each signature region has the structure Y-Z-X4-28-Y-Z, wherein all Y:s are selected from one of (i)-(iv), wherein (i) is R or K, (ii) is Y, F, W or L, (iii) is E and (iv) is D, and each X and each Z are independently any amino acid residue, provided that the Z:s are not P if the Y:s are selected from (i)-(iii); and each signature region comprises at least one amino acid residue comprising a heavy isotope.

This aspect relates to fusion polypeptides that may also be employed in the methods according to the invention. As throughout the specification, the target polypeptide may be any polypeptide, in particular a polypeptide naturally occurring in the proteome of any organism or cell in any state. The two regions comprised in the fusion polypeptide according to the fourth aspect of the invention are chosen such that each of them comprises at least two specific structural elements referred to as "signature regions". Importantly, the N- and C-terminal amino acids of each signature region are selected such that they are recognized by a protease suitable for the mass spectrometry protocol described herein. The amino acids of (i)-(iv) are thus based on the selectivity of the following proteases: trypsin, which cleaves on the carboxyl side of arginine (R) and lysine (K) residues unless followed by proline (P); chymotrypsin, which cleaves on the carboxyl side of tyrosine (Y), phenylalanine (F), tryptophan (W) and leucine (L) residues unless followed by proline (P); Lys-C, which cleaves on the carboxyl side of lysine (K) residues unless followed by proline (P); Glu-C, which cleaves on the carboxyl side of glutamate (E) residues unless followed by proline (P); Arg-C, which cleaves on the carboxyl side of arginine (R) residues unless followed by proline (P); and Asp-N, which cleaves on the amino side of aspartate (D) residues. This design principle of the fusion polypeptides ensures that, upon proteolytic digestion, at least two mass-altered proteolytic products are obtained from the target and tag region, respectively. It is to be understood that the same Y residue may constitute the carboxylic end of a first signature region and the amino end of a second signature region.

The general term "mass-altered" is used herein as defined above. Preferably, it refers to a frequency of at least one isotope which deviates from the naturally occurring frequency/ies thereof, preferably to the exclusive occurrence of at least one heavy isotope, heavy isotopes preferably being selected from D, 13C and 15N.

In a preferred embodiment of the fusion polypeptide of the invention, said tag region or said tag polypeptide, respectively, corresponds to, i.e. comprises or consists of a solubility tag or a fragment thereof, said solubility tag being selected from Maltose-binding protein (MBP), Glutathione-S-transferase (GST), Thioredoxin (Trx), N-Utilization substance (NusA), Small ubiquitin-modifier (SUMO), a Solubility-enhancing tag (SET), a Disulfide forming protein C (DsbC), Seventeen kilodalton protein (Skp), Phage T7 protein kinase (T7PK), Protein G B1 domain (GB1), Protein A IgG ZZ repeat domain (ZZ) and Albumin Binding Protein (ABP). The structures of these solubility tags are known in the art and readily available to the skilled person. It follows from the above definition that the solubility tag (or fragment thereof) is mass-altered when constituting the tag region of the fusion polypeptide of the fourth aspect.

Preferably, said fragment is chosen such that the solubility conferring properties are retained or not significantly compromised. Whether or not this is the case can be determined by the skilled person without further ado, for example, by performing solubility assays for fusion constructs comprising a test polypeptide on the one hand and the solubility tag at issue or a fragment thereof on the other hand. By comparing solubility of constructs comprising the entire solubility tag with constructs comprising a fragment thereof, it can be determined whether and to which extent the solubility conferring properties are retained by the fragment under consideration.

For reasons discussed above, the sequences of the at least two signature regions of the tag region are, according to one embodiment, distinct from any sequence derivable from the human proteome by means of proteolysis.

The fusion polypeptide of the fourth aspect may for example be used in a diagnosis of a medical condition in a subject comprising the ex vivo quantification of a target polypeptide in a sample from the subject. Whenever human samples are analyzed, it may be beneficial if the tag region is not a human polypeptide. Thus, in an embodiment of the fourth aspect, the amino acid sequence of the tag region is not an amino acid sequence of a human protein or a fragment thereof. As human proteins may have high homology to proteins of other eukaryotes, it may be particularly preferred if the tag region has the amino acid sequence of a prokaryotic (e.g. bacterial) protein or a fragment thereof.

As already noted above, a particularly preferred tag region or tag polypeptide has the sequence set forth in SEQ ID NO: 1.

According to further preferred embodiments, said tag region consists of 40 to 150 amino acids, and independently said target region consists of 20 to 150 amino acids, such as 25 to 100 amino acids. Moreover, it is preferred that the fusion polypeptide consists of 80 to 300, more preferably 100 to 200 amino acids.

According to further preferred embodiments, said target region, and independently said tag region, comprises at least 3 such as at least 4, 5, 6, 7 or 8 signature regions. These preferred embodiments provide for an increasing number of proteolytic products to be formed from each of said regions when said fusion polypeptide is brought into contact with a proteolytic enzyme, proteolytic enzymes being further detailed below.

According to a further preferred embodiment, each signature region independently comprises at least 2, such as at least 3 or 4 amino acid residues comprising a heavy isotope.

LysC and trypsin has been found to be particularly suitable proteolytic enzymes (see e.g. the examples below). According to a further preferred embodiment, said Y:s are thus selected from R and K.

As stated above, preferred heavy isotopes are to be selected from deuterium (D), 13C and 15N.

Normally, the amino acid residues comprising a heavy isotope of the fusion polypeptide comprises more than one heavy isotope. A higher number of incorporated heavy isotopes may be preferred as it provides a larger mass shift. In a further preferred embodiment, the at least one amino acid residue comprising a heavy isotope is selected from L-arginine-13C6, L-arginine-13C615N4, L-arginine-13C615N4D7, L-arginine-15N4D7, L-arginine-15N4, L-lysine-13C615N2, L-lysine-15N2, L-lysine-13C6, L-lysine-13C615N2D9, L-lysine-15N2D9, L-lysine-D4, L-methionine-13CD3, L-tyrosine-13C9, L-tyrosine-15N and L-tyrosine-13C915N. Such heavy isotope labeled amino acids are well known in the art and available from a variety of manufacturers. The use of one or more of these amino acids is preferred for any labeling schemes and patterns according to the present invention. In a preferred mode, all lysines and arginines are labeled so that tryptic peptides typically contain one labeled amino acid as trypsin specifically cleaves C-terminally to arginine and lysine.

According to a further preferred embodiment, the fusion polypeptide further comprises a purification tag.

Moreover, to allow for an efficient expression of the fusion polypeptide, it is preferred that the target region of the fusion polypeptide does not correspond to a transmembrane spanning region of the target polypeptide. Further, it is also preferred that the target region of the fusion polypeptide does not correspond to a signal peptide of the target polypeptide, since the signal peptides are often cleaved off in a mature version of the target polypeptide.

In a preferred embodiment of any of the methods according to the invention as described above, said fusion polypeptide(s) is/are as defined in accordance with the fourth aspect of the present invention as well as embodiments referring back thereto.

Preferred purification tags are to be selected from His tag, a FLAG tag, a SBP tag, a myc tag and a OneStrep tag.

For a user quantifying one or more target proteins or polypeptides in a sample according to the present disclosure, it may be convenient to obtain the fusion polypeptide(s) necessary for the quantification preloaded onto a solid phase suitable for the proteolytic digestion. Such solid phase may be a solid support, a column or a filter. Preferably, the amount of fusion polypeptides on said support in the column is predetermined. Thus, the step of spiking the sample with the fusion polypeptide(s) is not in the responsibility of the user, which also reduces the risk of human error in the procedure. In a fifth aspect, the present invention thus furthermore relates to a column in or onto which at least one fusion polypeptide according to the fourth aspect is arranged. Means of arranging are within the skills of the skilled person and include covalent attachment as well as non-covalent adsorption or absorption.

A proteolytic enzyme such as trypsin, chymotrypsin, Lys-C, Glu-C or Asp-N may also be arranged in or onto the column. When using such a column, the user does not have to add the proteolytic enzyme for the digestion, which may be convenient and further reduce the risk of human error. According to one embodiment, the fusion polypeptide(s) are separated from the proteolytic enzyme on the support/in the column so as to prevent any proteolytic digestion before the sample is added.

The present invention in a sixth aspect provides a kit comprising: (a) at least one fusion polypeptide according to the fourth aspect; and (b) (i) a second polypeptide comprising or consisting of the same amino acid sequence as the tag region as defined in accordance with the fourth aspect but being differently isotope labeled compared to said tag region and/or (ii) a proteolytic enzyme, such as trypsin, chymotrypsin, Lys-C, Glu-C or Asp-N. The combination of the products necessary for the quantification protocol described herein into a kit may provide for increased reproducibility and decreased risk of human error at the users side. The second polypeptide of the sixth aspect may for example be "unlabeled". It may also be "middle weight" or "extra heavy weight". Such embodiments are discussed above in connection with the method aspects.

In a preferred embodiment of the kit, the at least one fusion polypeptide is arranged in or onto a column according to the fifth aspect of the invention. In a further preferred embodiment of the kit, said second polypeptide is provided in a known absolute amount.

In a further aspect, the present invention relates to use of a quantitative standard as defined in the second aspect or of a fusion polypeptide according to the fourth aspect of the invention as a reference in a target polypeptide quantification. In a preferred embodiment of the use according to the invention, said quantification is effected by mass spectrometry.

Various further embodiments of the use aspect are described in connection with the other aspects above.

EXAMPLES

Figure 1:
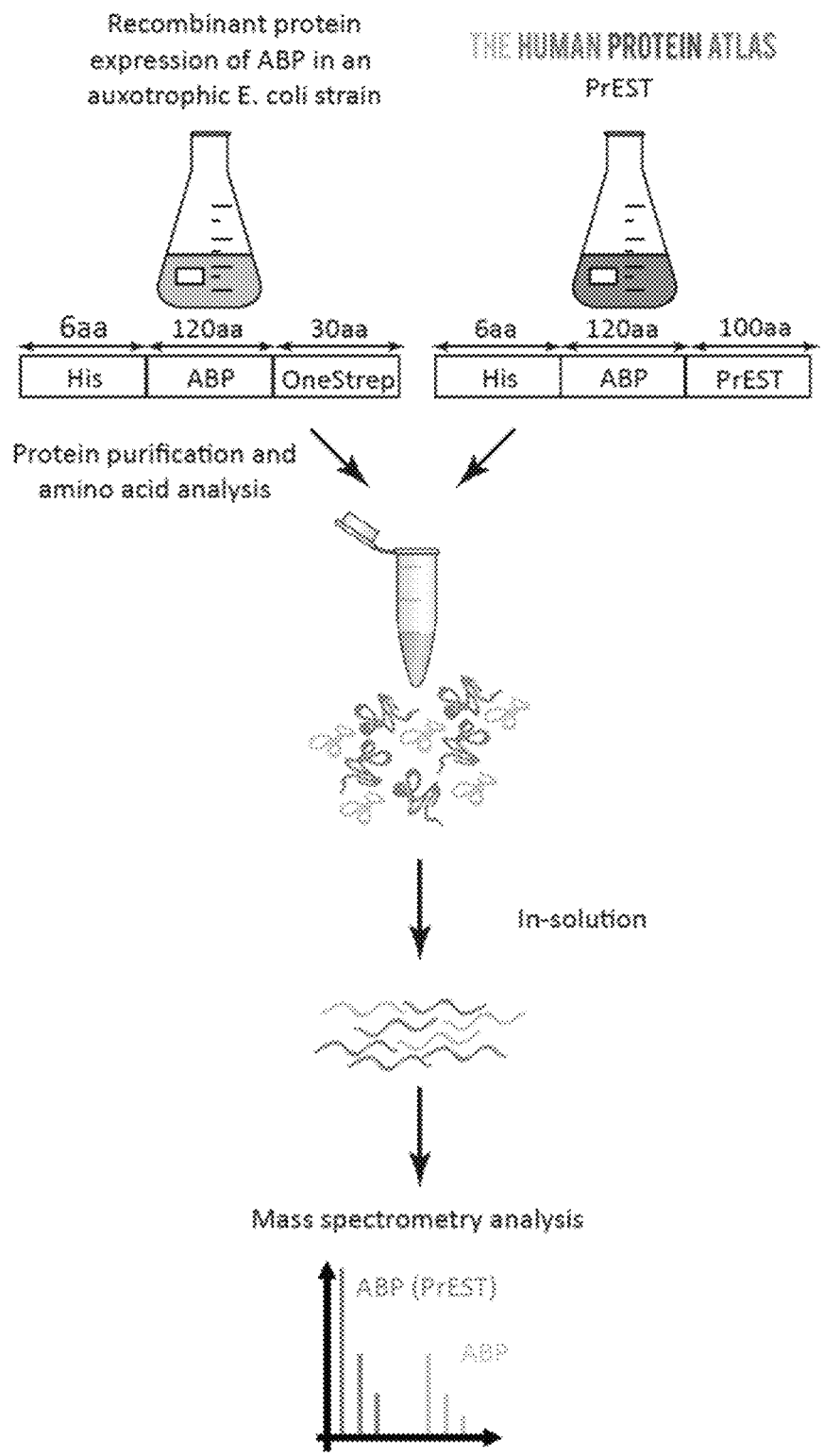
FIG. 1: Schematic workflow for accurate determination of PrEST concentrations. Heavy or light ABP is recombinantly expressed in an auxotrophic *E. coli* strain and purified using the C-terminal OneStrep tag. The heavy labeled ABP, whose concentration is measured separately by amino acid analysis, and the PrEST are mixed together and an in-solution digest is performed. Peptides are measured with a short LC MS/MS run on a benchtop mass spectrometer and the PrEST concentration is accurately determined by the SILAC ratio of the ABP peptides originating from the PrEST and the ABP.

The examples illustrate the invention:

Example 1

Materials and Methods

Protein Epitope Signature Tags—The short protein fragments, i.e. the subsequences of target polypeptides, were produced in high-throughput by the Human Protein Atlas where they are used as antigens for antibody production (18, 19). In brief, suitable Protein Epitope Signature Tags (PrESTs) representing unique regions of each target protein were designed using the human genome sequence as template (EnsEMBL). Unique PrESTs with a size between 50 to 150 amino acids and low homology to other human proteins were selected, including epitope- and domain-sized similarities to other proteins, signal peptides and transmembrane regions (18). The cloning, protein expression and purification were performed as previously described (19, 20). For optimal storage PrESTs were lyophilized and dissolved in 8M urea and stored at −20° C. until further use. To ascertain that the PrESTs had an endogenous counterpart in HeLa cells, we selected 50 proteins spread over the abundance range of a HeLa proteome that we had measured at a depth of about 4,000 proteins. Proteins were picked without regards to specific protein classes, cellular localizations or functions. Of these 50 proteins, 43 were readily available from the Protein Atlas pipeline in recombinantly expressed form. For multiplexing experiments these 43 PrESTs were mixed together—each at the appropriate concentration. This 'master mix' that was then spiked into cell lysates.

Cell culture—For SILAC labeling, HeLa cells were cultured in Dulbecco's modified Eagle's medium (Invitrogen) containing 10% dialyzed fetal bovine serum (Gibco) and penicillin/streptomycin (Gibco). Heavy arginine (high purity Arg10, Cambridge Isotope Laboratories) and heavy lysine (high purity Lys8, Cambridge Isotope Laboratory) were added to a final concentration of 33 µg/ml or 76 µg/ml, respectively. After six passages cells were fully labeled as assessed by mass spectrometry. Cells were counted using a Countess cell counter (Invitrogen) and aliquots of 106 cells were snap frozen and stored at −80° C.

Protein expression and purification of ABP (Albumin Binding Protein)—The expression vector pAff8c (Human Protein Atlas) was modified via SLIC cloning (21) inserting a OneStrep affinity tag to the C-terminus of the Albumin Binding Protein (ABP). To express heavy labeled ABP in *E. coli*, an expression strain auxotrophic for arginine and lysine was used (33). Cultures were grown in PA5052 minimal autoinduction media as previously described in (22) but with the addition of 18 normal ('light') amino acids and heavy arginine and lysine. Cultures were grown overnight and harvested at an OD600 of about 5.7. *E. coli* cells were lysed in 100 mM Tris, 150 mM NaCl and Protease Inhibitor (Roche) using a Bioruptor (Diagenode). Cell debris was removed by centrifugation and soluble ABP was purified using affinity chromatography on a StrepTap Hitrap column (GE Healthcare) coupled to an ÄKTA system. The purity of the protein was evaluated by mass spectrometry via an in solution digest followed by LC MS/MS. Abundances of ABP and contaminants were estimated by adding the signal for their most intense peptides. ABP was dialyzed in PBS, aliquoted, snap frozen and stored at −80° C. The concentration of purified ABP was measured by amino acid analysis (Genaxxon BioScience GmbH).

Sample preparation—HeLa cells were lysed in 100 mM Tris, 4% SDS, 100 mM DTT, incubated for 5 min at 95° C. and disrupted using a Bioruptor. The lysate was cleared by centrifugation through SpinX filters (22 µm, Corning). The PrESTs were added at appropriate concentrations (see main text) to labeled HeLa cells and the samples were further processed by the FASP method (23). In brief, proteins were captured on a 30 kDa filter and SDS was exchanged with a urea containing buffer. Proteins were alkylated with iodoacetamide and trypsinzed (Promega). Further peptide separation was performed using pipette-based six fraction SAX as described (24).

The PrESTs and ABP were mixed and solubilized in denaturation buffer (6 M urea, 2 M thiourea in 10 mM HEPES, pH 8), reduced with DTT and subsequently alkylated with iodoacetamide. The protein mixture was digested with LysC (Wako) for 3 h, diluted with ammonium bicarbonate and further digested with trypsin overnight. The digestion was stopped by acidifying with TFA and desalted on $C_{18}$-Empore disc StageTips (25).

Liquid chromatography and mass spectrometry—Analysis of the light PrESTs spiked into HeLa cells was performed on a LTQ-Orbitrap mass spectrometer (Thermo Fisher Scientific) coupled to an Easy nano-HPLC via a nanoelectrospray ion source (Proxeon Biosystems, now Thermo Fisher Scientific). The peptides were separated on a 15 cm fused silica emitter packed in-house with reversed phase material ReproSil-Pur 120 C18-AQ 3 µm resin (Dr. Maisch GmbH) and eluted with a 205 min gradient from 5-35% buffer B (80% acetonitrile, 0.5% acetic acid). The mass spectrometer was operated in a data dependent fashion to automatically measure MS and consecutive MS/MS. LTQ-Orbitrap full scan MS spectra (from 300 to 1650 m/z) were acquired with a resolution of 60,000 at m/z 400. The seven most abundant ions were sequentially isolated and fragmented in the linear ion trap using collision induced dissociation (CID) followed by analysis in the linear ion trap.

Analysis of the PrESTs spiked into HeLa cells was performed on an LTQ-Orbitrap Velos mass spectrometer (Thermo Fisher Scientific) coupled to an Easy nano-HPLC via a nanoelectrospray ion source (Thermo Fisher Scientific). The peptides were separated on a 20 cm column packed in-house using C18-AQ 1.8 µm resin (Dr. Maisch GmbH) and eluted with a 205-min gradient from 5-35% buffer B. The mass spectrometer was operated in a data dependent fashion to automatically measure MS and 10 consecutive MS/MS applying higher energy collision dissociation (HCD) (34). LTQ-Orbitrap full scan MS spectra (from 100 or 300 to 1650 m/z) were acquired with a resolution of 60,000 at m/z 400.

The PrEST-ABP peptides were analyzed online on the Exactive instrument with HCD option (Thermo Fisher Scientific) using the same nano-HPLC setup as described above. The peptides were eluted with a linear gradient with 5-30% buffer B over 40 min. The Exactive mass spectrometer identified peptides with All Ion Fragmentation (AIF) by performing alternating MS scans (300-1600 m/z) of the precursor ions and all ion fragmentation scans (100-1600 m/z) using stepped HCD fragmentation (26). Both scans were acquired at a resolution of 100 000 at m/z 200.

Data analysis—Acquired data were analyzed with MaxQuant (27) (version 1.1.1.36) using the human IPI database (v 3.68-87,083 entries). Common contaminants and the sequence of the ABP solubility tag were added to this database. For peptide identification we used Andromeda, a probabilistic search engine incorporated in to the MaxQuant framework (28). Carbamidomethylation of cysteine was included in the search as a fixed modification and methionine oxidation as well as N-terminal acetylation were included as variable modifications. We allowed two miscleavages and required a minimum of six amino acids per identified peptide. The initial mass tolerance for precursor ions or fragment ions was set to 6 ppm and fragment masses were allowed to deviate by up to 0.5 Th. For statistical evaluation of the data obtained, the posterior error probability and false discovery rate (FDR) were used. The FDR was determined by searching a reverse database and was set to 0.01 for peptide identification.

The AIF data was processed as described above except that up to 50 peaks were analyzed per 100 m/z with a tolerance of 15 ppm. The precursor ion mass was matched with the possible fragment ion candidates on the basis of the cosine correlation value of at least 0.6 (26).

Enzyme-linked Immunosorbent Assay—Absolute amounts measurements of proto-oncogene c-Fos and Stratifin (14-3-3σ) was carried out by ELISA. The kits were purchased from USCNK Life Science and performed according to the manufacturer's instructions. The HeLa cells were lysed in PBS, RIPA 1 (50 mM Tris pH 7.5, 150 mM NaCl, 1% NP-40) or RIPA2 (50 mM Tris pH 7.5, 150 mM NaCl, 1% NP-40; 0.1% SDS) with protease inhibitors. The cells were disrupted by 3 freeze-thaw cycles and sonication using the Biorupter. For the ELISA the samples were diluted 1:10. Fluorescence activity was measured by a microplate reader (Tecan) and converted to actual concentration by a standard curve.

Example 2

Absolute Quantification of Proteins in HeLa Cells

Unlike relative quantification, absolute quantification may be effected as a two step process that firstly requires measurement of the absolute amount of the standard and secondly the relative amount of the standard compared to the analyte of interest. Determination and subsequent control of the level of standard is by no means trivial and can easily be the step that limits the overall accuracy of the approach. Below, we first describe a generic method to determine the absolute amount of each PrEST with high accuracy.

Then we construct a 'master mix' of different PrESTs and evaluate the ability of the SILAC-PrEST method to accurately quantify cellular proteins. We then apply the master mix to determine the copy numbers of 37 proteins in a cancer cell line. Finally, we describe an alternative workflow for the quantification of single proteins of interest, in which the two steps are combined into one LC MS/MS analysis.

Accurate measurement of PrEST concentrations—Each PrEST is already fused to the Albumin Binding Domain (ABP), a solubilization tag of 120 amino acids. In silico digest of ABP results in 40 tryptic peptides with a length between 6 and 30 amino acids (Suppl. Table 1). We recombinantly expressed a heavy SILAC labeled version of the ABP protein tag. When necessary, we used a dual affinity approach based on an N-terminal His-tag and a C-terminal OneStrep tag to generate highly purified protein fragment and to ensure that only full length ABP was obtained. The absolute concentration of ABP protein fragment was determined by amino acid analysis, which is the most accurate method for protein quantification, but which is only applicable to highly purified proteins in relatively large amounts. Heavy SILAC incorporation into ABP was 99% and its purity was about 97% as judged by mass spectrometry (see Experimental Procedures). Because these two factors operate in a compensating direction and because of the small size of the effect, the measured concentration of ABP was not adjusted for them.

SUPPLEMENTARY TABLE 1 all ABP peptides detected in the AIF runs. All in silico peptides of the solubility tag ABP as well as the identified peptides when determining of the accurate concentration of the PrEST (see FIG. 1) for all three master mixes.

| Peptide sequence | SEQ ID NO. | Length | Mass | Missed cleavage | detected |
|---|---|---|---|---|---|
| TVEGVK | 2 | 6 | 631.354 | 0 | x |
| NLINNAK | 3 | 7 | 785.440 | 0 | x |
| SIELAEAK | 4 | 8 | 859.465 | 0 | x |
| YGVSDYHK | 5 | 8 | 967.440 | 0 | x |
| YGVSDYYK | 6 | 8 | 993.444 | 0 | x |
| VLANRELDK | 7 | 9 | 1056.593 | 1 | x |
| SQTPAEDTVK | 8 | 10 | 1074.519 | 0 | x |
| DLQAQVVESAK | 9 | 11 | 1186.619 | 0 | x |
| GSHMASLAEAK | 10 | 11 | 1100.528 | 0 | |
| DLQAQVVESAKK | 11 | 12 | 1314.714 | 1 | x |
| ELDKYGVSDYHK | 12 | 12 | 1452.689 | 1 | x |
| ELDKYGVSDYYK | 13 | 12 | 1478.693 | 1 | x |
| ISEATDGLSDFLK | 14 | 13 | 1394.693 | 0 | x |
| NLINNAKTVEGVK | 15 | 13 | 1398.783 | 1 | |
| SIELAEAKVLANR | 16 | 13 | 1412.799 | 1 | |

SUPPLEMENTARY TABLE 1-continued all ABP peptides detected in the AIF runs. All in silico peptides of the solubility tag ABP as well as the identified peptides when determining of the accurate concentration of the PrEST (see FIG. 1) for all three master mixes.

| Peptide sequence | SEQ ID NO. | Length | Mass | Missed cleavage | detected |
|---|---|---|---|---|---|
| DLQAQVVESAKKAR | 17 | 14 | 1541.853 | 2 | |
| ARISEATDGLSDFLK | 18 | 15 | 1621.831 | 1 | x |
| YGVSDYHKNLINNAK | 19 | 15 | 1734.869 | 1 | |
| YGVSDYYKNLINNAK | 20 | 15 | 1760.873 | 1 | |
| GSHMASLAEAKVLANR | 21 | 16 | 1653.862 | 1 | |
| KARISEATDGLSDFLK | 22 | 16 | 1749.926 | 2 | x |
| MGSSHHHHHHSSGLVPR | 23 | 17 | 1898.882 | 0 | |
| SIELAEAKVLANRELDK | 24 | 17 | 1898.047 | 2 | x |
| TVEGVKDLQAQVVESAK | 25 | 17 | 1799.963 | 1 | x |
| VLANRELDKYGVSDYHK | 26 | 17 | 2006.022 | 2 | x |
| VLANRELDKYGVSDYYK | 27 | 17 | 2032.027 | 2 | x |
| SQTPAEDTVKSIELAEAK | 28 | 18 | 1915.974 | 1 | x |
| TVEGVKDLQAQVVESAKK | 29 | 18 | 1928.058 | 2 | x |
| ELDKYGVSDYHKNLINNAK | 30 | 19 | 2220.118 | 2 | |
| ELDKYGVSDYYKNLINNAK | 31 | 19 | 2246.122 | 2 | |
| GGGSGGGSGGSAWSHPQFEK | 32 | 20 | 1845.803 | 0 | |
| GSHMASLAEAKVLANRELDK | 33 | 20 | 2139.111 | 2 | |
| YGVSDYHKNLINNAKTVEGVK | 34 | 21 | 2348.213 | 2 | |
| YGVSDYYKNLINNAKTVEGVK | 35 | 21 | 2374.217 | 2 | |
| ISEATDGLSDFLKSQTPAEDTVK | 36 | 23 | 2451.202 | 1 | x |
| SQTPAEDTVKSIELAEAKVLANR | 37 | 23 | 2469.308 | 2 | |
| NLINNAKTVEGVKDLQAQVVESAK | 38 | 24 | 2567.392 | 2 | |
| ARISEATDGLSDFLKSQTPAEDTVK | 39 | 25 | 2678.34 | 2 | x |
| ALIDEILAALPGTFAHYGSAWSHPQFEK | 40 | 28 | 3068.54 | 0 | |
| MGSSHHHHHHSSGLVPRGSHMASLAEAK | 41 | 28 | 2981.4 | 1 | |

LC MS/MS of ABP indeed revealed many readily detectable tryptic peptides (see below). Each of the 43 PrESTs from the Protein Atlas Project was separately mixed with a known amount of labeled ABP as schematically outlined in FIG. 1 to allow for a SILAC LC-MS/MS experiment. As this experiment requires a separate LC MS/MS run for each PrEST it was likely to be rate limiting for the overall project.

Figure 2A:
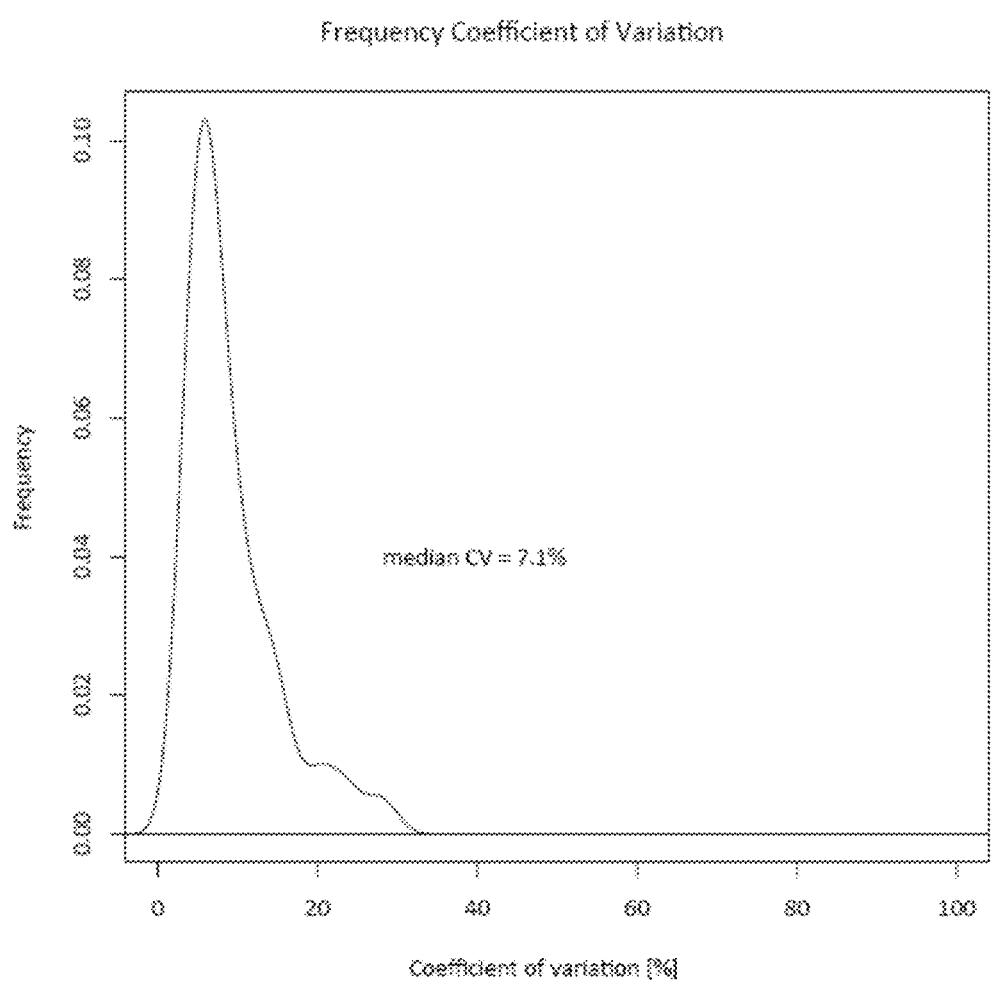
FIG. 2: Accuracy of ABP quantification. (A) Density plot of the overall distribution of the 43 coefficients of variation (CVs) of the ABP peptides measured on a benchtop Exactive mass spectrometer. (B) Representative example proteins showing the ratios of the ABP peptides and their coefficients of variation (CVs).

We therefore decided to perform this analysis on an economical and robust benchtop Orbitrap instrument rather than on a Velos instrument. The Exactive instrument cannot isolate peptide precursors, therefore we identified the peptides by All Ion Fragmentation (AIF) (26) in 1 h runs. Typically, at least eight labeled ABP peptides could be quantified against the corresponding ABP peptides from the PrESTs, leading to a median coefficient of variation (CV) of 7% for PrEST quantification (FIG. 2A).

To overcome the step of measuring the PrESTs concentration, which limits overall throughput, the heavy PrESTs were measured by static nanoelectrospray on an automated chip-based system (TriVersa Nanomate). This enabled higher throughput measurements of these simple mixtures of ABP peptides using low sample consumption. The peptide ratio showed a median coefficient of variation 5.5%, an improvement over the Exactive based measurement of 7%.

Figure 2B:
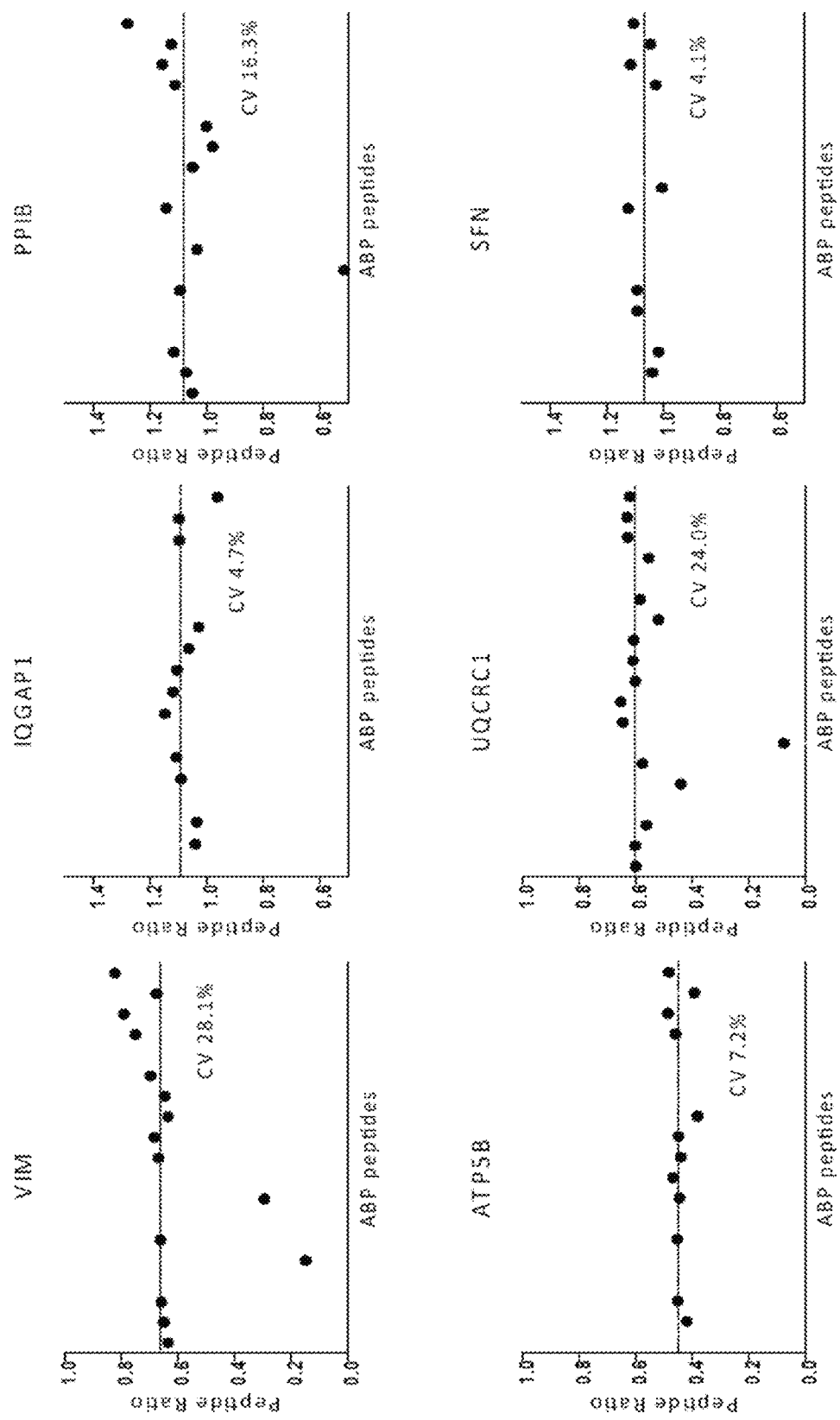

Importantly, a particular PrEST quantification can be repeated at this stage until a desired accuracy is achieved. Here, this was not done, since the accuracy of PrEST quantification was estimated to be higher than that of the other steps in the workflow. A few typical examples of results from the PrEST quantification are shown in FIG. 2B. Note that the quantification accuracy does not depend on the cellular abundance or any other attributes of the target protein, since the same amounts of PrESTs is used in each PrEST quantification experiment. Importantly, quantification accuracy in our workflow also does not depend on the purity of the PrEST because our method specifically measures the concentration of PrEST and not of total protein.

PrEST master mix and endogenous protein quantification—Having quantified the PrEST amounts we proceeded to measuring protein expression levels in a human cancer cell line. For convenience we used unlabeled PrESTs and quantified against heavy SILAC labeled HeLa cells. Since digested total cell lysates consist of hundreds of thousands of tryptic peptides, the addition of a single or even a large number of PrEST does not change the overall complexity of the mixture. On the basis of the quantitative amounts established above, we here mixed 43 PrESTs together. In initial experiments we used equimolar mixtures of PrESTs, which were spiked into HeLa lysate in different amounts. The measured SILAC ratios established appropriate levels of each PrEST in the master mix, such that the SILAC ratios were within the most accurately quantifiable range, i.e. relatively close to one to one.

The master mix with appropriate levels of all the 43 PrESTs was spiked into the lysate of SILAC labeled cells. The mixture was digested according to the FASP protocol followed by SAX fractionation and resulting in six fractions that were separately measured with 4 h gradients on an LTQ Orbitrap mass spectrometer. We were able to quantify 37 of the 43 proteins targeted by our PrEST master mix.

Figure 3:
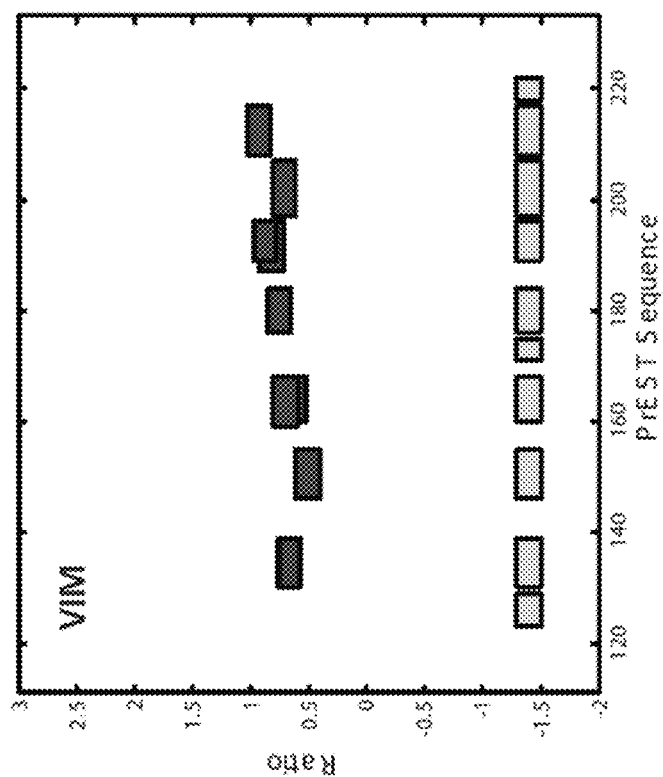
FIG. 3: Peptide ratio along the PrESTs sequences. The PrEST master mix was spiked into lysate of a cancer cell line and measured against the endogenous protein. The peptide ratios were extracted to quantify the proteins. The variation of the peptide ratios along the sequence is depicted. Overlapping peptides are due to missed cleavages.
Figure 3:
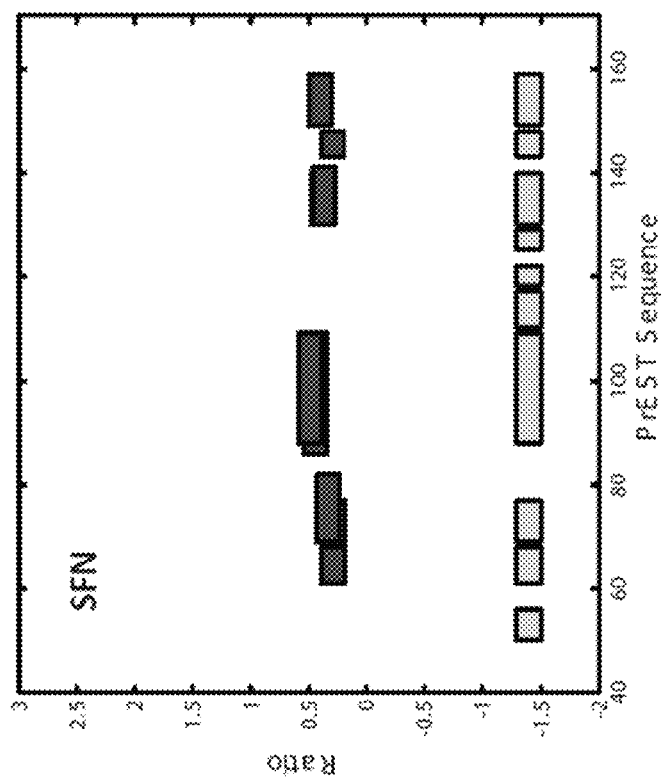
Figure 3:
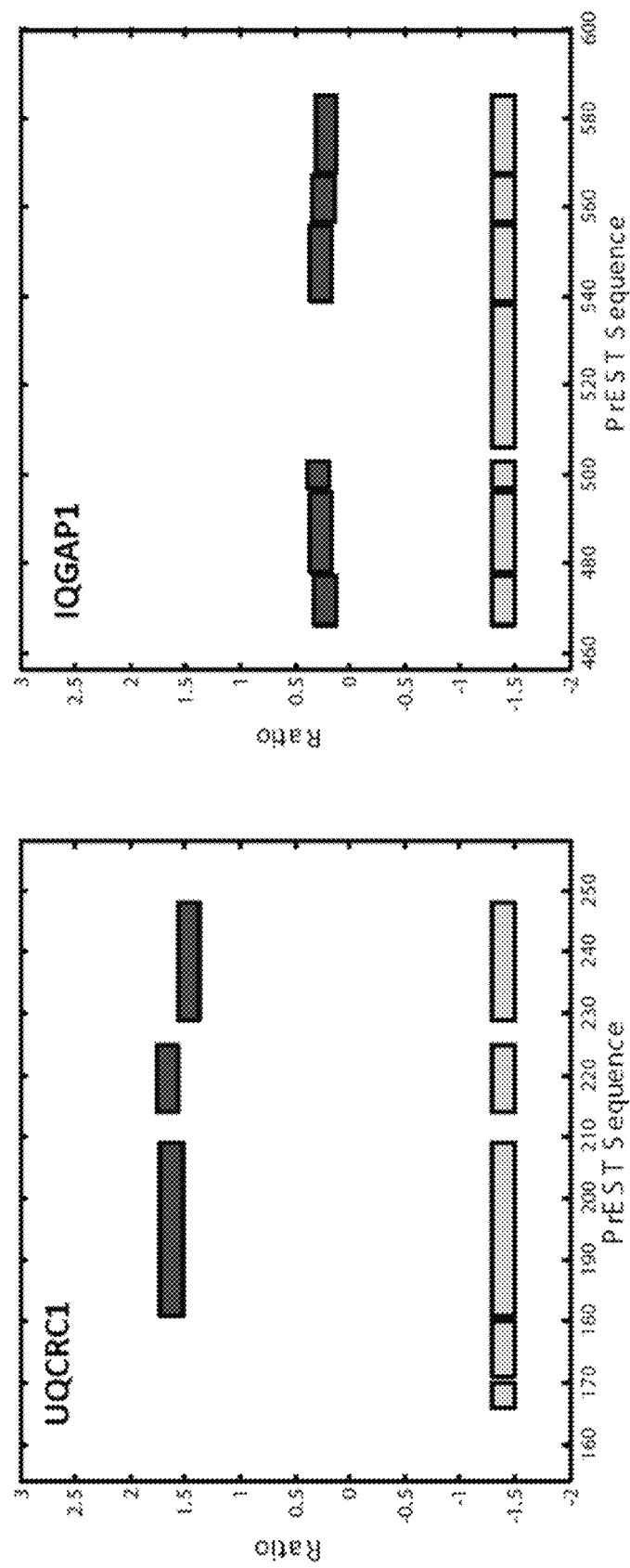
Figure 3:
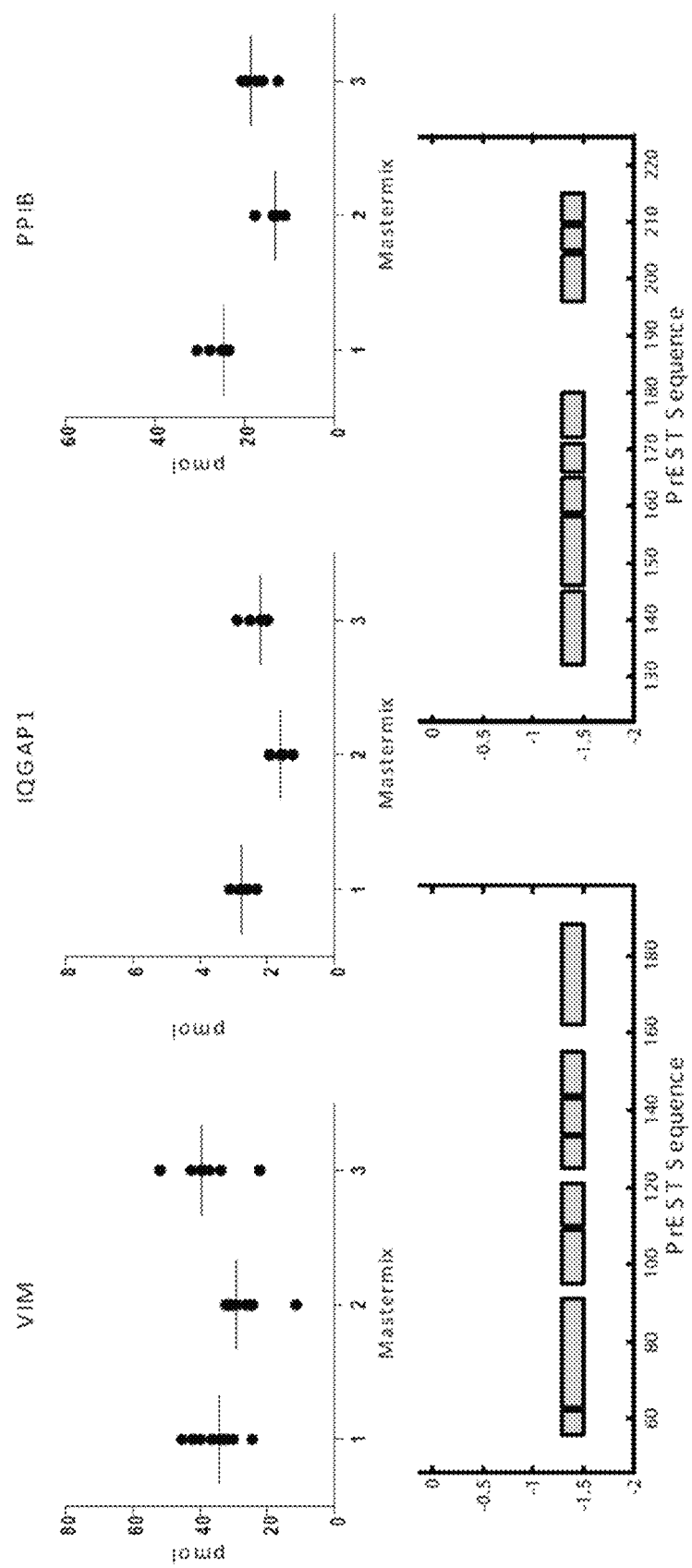

Proteins were generally quantified with several PrEST derived peptides (average 3.7 and median 3), leading to an overall median CV of 18% (Supplementary Table 2). The results for these 37 protein targets are shown in FIG. 3 and the complete identification and quantification information is described in Supplementary Table 2. As an example, the adhesion protein IQGAP1 was quantified with five peptides, which each gave nearly identical quantification results (CV 10.6%). Six of the seven quantified tryptic peptides of ATP5B (mitochondrial ATP synthase subunit beta), had very close SILAC ratios, however, one peptide had a ratio that differs by 38% from the median. This peptide is clearly an outlier and its deviating value contributes substantially to the CV value, raising it from 8.2% to 27.2%. Note however, that we base protein quantification on the median of the peptide values; therefore the outlier peptide hardly contributes to the measured protein expression value and the CV value therefore underestimates the accuracy actually obtained in this experiment. For the same reason modifications of the endogenous proteins in the region covered by the PrEST could cause outlier peptide ratios, which would contribute little to the measured protein ratio.

SUPPLEMENTARY TABLE 2

All identification and quantification information used to quantify proteins.

| Protein Names | Gene Name | Sequence | SEQ ID NO. | Ratio H/L Mastermix (1) | CV(%) |
|---|---|---|---|---|---|
| Cytosolic acyl coenzyme | ACOT7 | ADLPPCGACITGR | 42 | NaN | — |
| Cytosolic acyl coenzyme | ACOT7 | GCCAPVQVVGPR | 43 | NaN | |
| Cytosolic acyl coenzyme | ACOT7 | IMRPDDANVAGNVHGGTILK | 44 | 0.27622 | |
| Cytosolic acyl coenzyme | ACOT7 | LVAGQGCVGPR | 45 | NaN | |
| Cytosolic acyl coenzyme | ACOT7 | MIEEAGAIISTR | 46 | NaN | |
| AFG3-like protein 2 | AFG3L2 | EQYLYTK | 47 | 0.77684 | 6.27 |
| AFG3-like protein 2 | AFG3L2 | HLSDSINQK | 48 | 0.68028 | |
| AFG3-like protein 2 | AFG3L2 | LASLTPGFSGADVANVCNEAALIAAR | 251 | 0.80176 | |
| AFG3-like protein 2 | AFG3L2 | MCMTLGGR | 49 | 0.72983 | |
| AFG3-like protein 2 | AFG3L2 | VSEEIFFGR | 50 | 0.76345 | |
| ATPase family AAA dom | ATAD2 | DNFNFLHLNR | 51 | 0.12868 | — |
| ATP synthase subunit beta | ATP5B | IMNVIGEPIDER | 52 | 0.82979 | 23.09 |
| ATP synthase subunit beta | ATP5B | IPVGPETLGR | 53 | 0.85299 | |
| ATP synthase subunit beta | ATP5B | LVLEVAQHLGESTVR | 54 | 0.71767 | |
| ATP synthase subunit beta | ATP5B | TIAMDGTEGLVR | 55 | 0.4194 | |
| ATP synthase subunit beta | ATP5B | VLDSGAPIK | 56 | 0.76219 | |
| ATP synthase subunit beta | ATP5B | VLDSGAPIKIPVGPETLGR | 57 | 0.89528 | |
| Zinc finger protein 828 | C13orf8 | ALFPEPR | 58 | NaN | 65.67 |
| Zinc finger protein 828 | C13orf8 | AVELGDELQIDAIDDQK | 59 | NaN | |
| Zinc finger protein 828 | C13orf8 | CDILVQEELLASPK | 60 | NaN | |
| Zinc finger protein 828 | C13orf8 | DNQESSDAELSSSEYIK | 61 | 0.081796 | |
| Zinc finger protein 828 | C13orf8 | HALFPELPK | 62 | NaN | |

SUPPLEMENTARY TABLE 2-continued

All identification and quantification information used to quantify proteins.

| | | | | | |
|---|---|---|---|---|---|
| Zinc finger protein 828 | C13orf8 | KDNQESSDAELSSSEYIK | 63 | NaN | |
| Zinc finger protein 828 | C13orf8 | LLEDTLFPSSK | 64 | 0.22363 | |
| SRA stem-loop-interacti | C14orf156 | CILPFDK | 65 | 3.5457 | 74.19 |
| SRA stem-loop-interacti | C14orf156 | EHFAQFGHVR | 66 | NaN | |
| SRA stem-loop-interacti | C14orf156 | GLGWVQFSSEEGLR | 67 | 0.35422 | |
| SRA stem-loop-interacti | C14orf156 | IPWTAASSQLK | 68 | NaN | |
| SRA stem-loop-interacti | C14orf156 | NALQQENHIIDGVK | 69 | 3.5138 | |
| SRA stem-loop-interacti | C14orf156 | SINQPVAFVR | 70 | NaN | |

| Protein Names | Gene Name | Sequence | Ratio H/L Mastermix (2) | CV(%) | Ratio H/L Mastermix (3) | CV(%) |
|---|---|---|---|---|---|---|
| Cytosolic acyl coenzyme | ACOT7 | ADLPPCGACITGR | NaN | — | NaN | — |
| Cytosolic acyl coenzyme | ACOT7 | GCCAPVQVVGPR | NaN | | NaN | |
| Cytosolic acyl coenzyme | ACOT7 | IMRPDDANVAGNVHGGTILK | 0.25644 | | 5.2343 | |
| Cytosolic acyl coenzyme | ACOT7 | LVAGQGCVGPR | NaN | | NaN | |
| Cytosolic acyl coenzyme | ACOT7 | MIEEAGAIISTR | NaN | | NaN | |
| AFG3-like protein 2 | AFG3L2 | EQYLYTK | 0.82239 | 4.61 | 1.4433 | 5.83 |
| AFG3-like protein 2 | AFG3L2 | HLSDSINQK | 0.78043 | | 1.3793 | |
| AFG3-like protein 2 | AFG3L2 | LASLTPGFSGADVANVCNEAALIAAR | 0.82107 | | NaN | |
| AFG3-like protein 2 | AFG3L2 | MCMTLGGR | 0.87038 | | 1.5475 | |
| AFG3-like protein 2 | AFG3L2 | VSEEIFFGR | 0.87166 | | NaN | |
| ATPase family AAA dom | ATAD2 | DNFNFLHLNR | 0.12046 | — | 0.87365 | — |
| ATP synthase subunit beta | ATP5B | IMNVIGEPIDER | 0.64229 | 14.83 | 1.0596 | 9.57 |
| ATP synthase subunit beta | ATP5B | IPVGPETLGR | 0.84263 | | 1.1617 | |
| ATP synthase subunit beta | ATP5B | LVLEVAQHLGESTVR | 0.73297 | | 0.90287 | |
| ATP synthase subunit beta | ATP5B | TIAMDGTEGLVR | 0.76715 | | 1.1006 | |
| ATP synthase subunit beta | ATP5B | VLDSGAPIK | 0.67515 | | 0.99543 | |
| ATP synthase subunit beta | ATP5B | VLDSGAPIKIPVGPETLGR | 0.95159 | | 1.1652 | |
| Zinc finger protein 828 | C13orf8 | ALFPEPR | NaN | 43.02 | NaN | 65.84 |
| Zinc finger protein 828 | C13orf8 | AVELGDELQIDAIDDQK | NaN | | NaN | |
| Zinc finger protein 828 | C13orf8 | CDILVQEELLASPK | NaN | | NaN | |
| Zinc finger protein 828 | C13orf8 | DNQESSDAELSSSEYIK | 0.099583 | | 0.34653 | |
| Zinc finger protein 828 | C13orf8 | HALFPELPK | NaN | | NaN | |
| Zinc finger protein 828 | C13orf8 | KDNQESSDAELSSSEYIK | NaN | | NaN | |
| Zinc finger protein 828 | C13orf8 | LLEDTLFPSSK | 0.18665 | | 0.9503 | |
| SRA stem-loop-interacti | C14orf156 | CILPFDK | 2.9157 | 76.61 | 1.466 | 40.99 |
| SRA stem-loop-interacti | C14orf156 | EHFAQFGHVR | 2.9391 | | 1.5112 | |
| SRA stem-loop-interacti | C14orf156 | GLGWVQFSSEEGLR | 0.33818 | | 0.2253 | |

SUPPLEMENTARY TABLE 2-continued

All identification and quantification information used to quantify proteins.

| | | | | | |
|---|---|---|---|---|---|
| SRA stem-loop-interacti | C14orf156 | IPWTAASSQLK | NaN | | 1.6141 |
| SRA stem-loop-interacti | C14orf156 | NALQQENHIIDGVK | 3.226 | | 1.5357 |
| SRA stem-loop-interacti | C14orf156 | SINQPVAFVR | 0.29812 | | 1.6403 |

| μl PrESTs (1 + 2) | μl PrESTs (3) | Exactive pmol/μl 1 | Exactive pmol/μl 2 | Exactive pmol/μl 3 | pmol PrEST 1 |
|---|---|---|---|---|---|
| 0.011 | 0.0017 | 275.36565 | 273.155 | 94.187082 | 3.029022 |
| 0.011 | 0.0017 | 275.36565 | 273.155 | 94.187082 | 3.029022 |
| 0.011 | 0.0017 | 275.36565 | 273.155 | 94.187082 | 3.029022 |
| 0.011 | 0.0017 | 275.36565 | 273.155 | 94.187082 | 3.029022 |
| 0.011 | 0.0017 | 275.36565 | 273.155 | 94.187082 | 3.029022 |
| 0.006 | 0.0107 | 125.05216 | 129.519 | 17.806094 | 0.750313 |
| 0.006 | 0.0107 | 125.05216 | 129.519 | 17.806094 | 0.750313 |
| 0.006 | 0.0107 | 125.05216 | 129.519 | 17.806094 | 0.750313 |
| 0.006 | 0.0107 | 125.05216 | 129.519 | 17.806094 | 0.750313 |
| 0.005 | 0.0025 | 179.90794 | 184.773 | 70.124349 | 0.89954 |
| 0.049 | 0.0855 | 239.56298 | 196.145 | 81.16038 | 11.73859 |
| 0.049 | 0.0855 | 239.56298 | 196.145 | 81.16038 | 11.73859 |
| 0.049 | 0.0855 | 239.56298 | 196.145 | 81.16038 | 11.73859 |
| 0.049 | 0.0855 | 239.56298 | 196.145 | 81.16038 | 11.73859 |
| 0.049 | 0.0855 | 239.56298 | 196.145 | 81.16038 | 11.73859 |
| 0.007 | 0.0048 | 112.51212 | 82.565 | 38.582311 | 0.787585 |
| 0.007 | 0.0048 | 112.51212 | 82.565 | 38.582311 | 0.787585 |
| 0.007 | 0.0048 | 112.51212 | 82.565 | 38.582311 | 0.787585 |
| 0.007 | 0.0048 | 112.51212 | 82.565 | 38.582311 | 0.787585 |
| 0.007 | 0.0048 | 112.51212 | 82.565 | 38.582311 | 0.787585 |
| 0.007 | 0.0048 | 112.51212 | 82.565 | 38.582311 | 0.787585 |
| 0.005 | 0.0378 | 151.61694 | 90.9 | 40.283794 | 0.758085 |
| 0.005 | 0.0378 | 151.61694 | 90.9 | 40.283794 | 0.758085 |
| 0.005 | 0.0378 | 151.61694 | 90.9 | 40.283794 | 0.758085 |
| 0.005 | 0.0378 | 151.61694 | 90.9 | 40.283794 | 0.758085 |
| 0.005 | 0.0378 | 151.61694 | 90.9 | 40.283794 | 0.758085 |
| 0.005 | 0.0378 | 151.61694 | 90.9 | 40.283794 | 0.758085 |

| pmol PrEST 2 | pmol PrEST 3 | pmol Protein 1 | pmol Protein 2 | pmol Protein 3 |
|---|---|---|---|---|
| 3.004705 | 0.160118 | #VALUE! | #VALUE! | #VALUE! |
| 3.004705 | 0.160118 | #VALUE! | #VALUE! | #VALUE! |
| 3.004705 | 0.160118 | 0.836676 | 0.770527 | 0.838106 |
| 3.004705 | 0.160118 | #VALUE! | #VALUE! | #VALUE! |
| 3.004705 | 0.160118 | #VALUE! | #VALUE! | #VALUE! |
| 0.777114 | 0.190525 | 0.582873 | 0.639091 | 0.274985 |
| 0.777114 | 0.190525 | 0.510423 | 0.606483 | 0.262791 |
| 0.777114 | 0.190525 | 0.601571 | 0.638065 | #VALUE! |
| 0.777114 | 0.190525 | 0.547601 | 0.676384 | 0.294838 |
| 0.777114 | 0.190525 | 0.572826 | 0.677379 | #VALUE! |
| 0.923865 | 0.175311 | 0.115753 | 0.111289 | 0.15316 |
| 9.611105 | 6.939212 | 9.740561 | 6.173117 | 7.35279 |
| 9.611105 | 6.939212 | 10.0129 | 8.098605 | 8.061283 |
| 9.611105 | 6.939212 | 8.424431 | 7.044652 | 6.265207 |
| 9.611105 | 6.939212 | 4.923163 | 7.373159 | 7.637297 |
| 9.611105 | 6.939212 | 8.947033 | 6.488938 | 6.9075 |
| 9.611105 | 6.939212 | 10.50932 | 9.145831 | 8.08557 |
| 0.577955 | 0.185195 | #VALUE! | #VALUE! | #VALUE! |
| 0.577955 | 0.185195 | #VALUE! | #VALUE! | #VALUE! |
| 0.577955 | 0.185195 | #VALUE! | #VALUE! | #VALUE! |
| 0.577955 | 0.185195 | 0.064421 | 0.057554 | 0.064176 |
| 0.577955 | 0.185195 | #VALUE! | #VALUE! | #VALUE! |
| 0.577955 | 0.185195 | #VALUE! | #VALUE! | #VALUE! |
| 0.577955 | 0.185195 | 0.176128 | 0.107875 | 0.175991 |
| 0.4545 | 1.522727 | 2.687941 | 1.325186 | 2.232318 |
| 0.4545 | 1.522727 | #VALUE! | 1.335821 | 2.301146 |
| 0.4545 | 1.522727 | 0.268529 | 0.153703 | 0.34307 |
| 0.4545 | 1.522727 | #VALUE! | #VALUE! | 2.457834 |
| 0.4545 | 1.522727 | 2.663758 | 1.46649 | 2.338452 |
| 0.4545 | 1.522727 | #VALUE! | 0.135496 | 2.49773 |

SUPPLEMENTARY TABLE 2-continued

All identification and quantification information used to quantify proteins.

| Protein Names | Gene Name | Sequence | SEQ ID NO. | Ratio H/L Mastermix (1) | CV(%) |
|---|---|---|---|---|---|
| Uncharacterized protein | C1orf65 | ILVELADEK | 71 | NaN | — |
| Hepatocellular carcinom | C9orf78 | GDSESEEDEQDSEEVR | 72 | NaN | — |
| Hepatocellular carcinom | C9orf78 | RGDSESEDEQDSEEVR | 73 | NaN | |
| Hepatocellular carcinom | C9orf78 | VQEETTLVDDPFQMK | 74 | 0.34795 | |
| Carbonyl reductase [NA | CBR3 | AFENCSEDLQER | 75 | 0.12453 | 3.00 |
| Carbonyl reductase [NA | CBR3 | FHSETLTEGDLVDLMK | 76 | 0.12993 | |
| Carbonyl reductase [NA | CBR3 | TNFFATR | 77 | NaN | |
| Carbonyl reductase [NA | CBR3 | VVNISSLQCLR | 78 | NaN | |
| Coiled-coil domain-cont | CCDC55 | NQEKPSNSESSLGAK | 79 | NaN | — |
| T-complex protein 1 sub | CCT2 | HGINCFINR | 80 | 0.63785 | 26.43 |
| T-complex protein 1 sub | CCT2 | ILIANTGMDTDK | 81 | 0.47498 | |
| T-complex protein 1 sub | CCT2 | ILIANTGMDTDKIK | 82 | 0.26858 | |
| T-complex protein 1 sub | CCT2 | LALVTGGEIASTFDHPELVK | 83 | 0.5415 | |
| T-complex protein 1 sub | CCT2 | LIEEVMIGEDK | 84 | 0.34771 | |
| T-complex protein 1 sub | CCT2 | VAEIEHAEK | 85 | 0.4707 | |
| T-complex protein 1 sub | CCT2 | VAEIEHAEKEK | 86 | 0.51512 | |
| Charged multivesicular 1 | CHMP6 | IAQQLER | 87 | 0.12113 | — |
| Charged multivesicular 1 | CHMP6 | YQEQLLDR | 88 | NaN | |
| COP9 signalosome complex | COPS5 | DHHYFK | 89 | 0.9528 | 3.53 |
| COP9 signalosome complex | COPS5 | ISALALLK | 90 | 0.90507 | |
| COP9 signalosome complex | COPS5 | SGGNLEVMGLMLGK | 91 | 0.96904 | |
| COP9 signalosome complex | COPS5 | VDGETMIIMDSFALPVEGTETR | 92 | NaN | |
| Cytochrome b5 reductase 4 | CYB5R4 | LLHDLNFSK | 93 | NaN | |
| Cytochrome b5 reductase 4 | CYB5R4 | QGHISPALLSEFLK | 94 | NaN | |
| Cytochrome b5 reductase 4 | CYB5R4 | TEDDIIWR | 95 | 0.035422 | |
| Probable ATP-depender | DDX20 | GEEENMMMR | 96 | 0.60662 | — |
| Probable ATP-depender | DDX20 | VLISTDLTSR | 97 | NaN | |

| Protein Names | Gene Name | Sequence | Ratio H/L Mastermix (2) | CV(%) | Ratio H/L Mastermix (3) | CV(%) |
|---|---|---|---|---|---|---|
| Uncharacterized protein | C1orf65 | ILVELADEK | NaN | — | NaN | — |
| Hepatocellular carcinom | C9orf78 | GDSESEEDEQDSEEVR | NaN | — | NaN | |
| Hepatocellular carcinom | C9orf78 | RGDSESEDEQDSEEVR | NaN | | NaN | |
| Hepatocellular carcinom | C9orf78 | VQEETTLVDDPFQMK | 0.27853 | | 0.54925 | |
| Carbonyl reductase [NA | CBR3 | AFENCSEDLQER | 0.10329 | 9.75 | 2.5724 | — |
| Carbonyl reductase [NA | CBR3 | FHSETLTEGDLVDLMK | NaN | | NaN | |
| Carbonyl reductase [NA | CBR3 | TNFFATR | 0.091036 | | NaN | |
| Carbonyl reductase [NA | CBR3 | VVNISSLQCLR | 0.11067 | | NaN | |

SUPPLEMENTARY TABLE 2-continued

All identification and quantification information used to quantify proteins.

| | | | | | | |
|---|---|---|---|---|---|---|
| Coiled-coil domain-cont | CCDC55 | NQEKPSNSESSLGAK | NaN | — | NaN | — |
| T-complex protein 1 sub | CCT2 | HGINCFINR | 0.42168 | 30.21 | 1.3197 | 7.84 |
| T-complex protein 1 sub | CCT2 | ILIANTGMDTDK | 0.37474 | | 1.0965 | |
| T-complex protein 1 sub | CCT2 | ILIANTGMDTDKIK | 0.1831 | | NaN | |
| T-complex protein 1 sub | CCT2 | LALVTGGEIASTFDHPELVK | 0.51676 | | 1.2981 | |
| T-complex protein 1 sub | CCT2 | LIEEVMIGEDK | 0.30789 | | 1.2599 | |
| T-complex protein 1 sub | CCT2 | VAEIEHAEK | 0.45578 | | 1.1598 | |
| T-complex protein 1 sub | CCT2 | VAEIEHAEKEK | 0.51219 | | 1.3444 | |
| Charged multivesicular 1 | CHMP6 | IAQQLER | 0.07044 | 9.14 | NaN | — |
| Charged multivesicular 1 | CHMP6 | YQEQLLDR | 0.080177 | | NaN | |
| COP9 signalosome complex | COPS5 | DHHYFK | 1.1093 | 19.40 | 1.7291 | 11.08 |
| COP9 signalosome complex | COPS5 | ISALALLK | 0.82773 | | 1.9194 | |
| COP9 signalosome complex | COPS5 | SGGNLEVMGLMLGK | 1.2254 | | 2.157 | |
| COP9 signalosome complex | COPS5 | VDGETMIIMDSFALPVEGTETR | NaN | | NaN | |
| Cytochrome b5 reductase 4 | CYB5R4 | LLHDLNFSK | NaN | — | NaN | 34.50 |
| Cytochrome b5 reductase 4 | CYB5R4 | QGHISPALLSEFLK | NaN | | 0.077032 | |
| Cytochrome b5 reductase 4 | CYB5R4 | TEDDIIWR | 0.034486 | | 0.12675 | |
| Probable ATP-depender | DDX20 | GEEENMMMR | 0.59133 | 21.50 | NaN | — |
| Probable ATP-depender | DDX20 | VLISTDLTSR | 0.43526 | | NaN | |

| µl PrESTs (1 + 2) | µl PrESTs (3) | Exactive pmol/µl 1 | Exactive pmol/µl 2 | Exactive pmol/µl 3 | pmol PrEST 1 |
|---|---|---|---|---|---|
| 0.006 | 0.0026 | 221.44221 | 130.904 | 52.045542 | 1.328653 |
| 0.006 | 0.0103 | 242.34528 | 179.229 | 78.04384 | 1.454072 |
| 0.006 | 0.0103 | 242.34528 | 179.229 | 78.04384 | 1.454072 |
| 0.006 | 0.0103 | 242.34528 | 179.229 | 78.04384 | 1.454072 |
| 0.006 | 0.003 | 164.39734 | 155.761 | 70.484927 | 0.986384 |
| 0.006 | 0.003 | 164.39734 | 155.761 | 70.484927 | 0.986384 |
| 0.006 | 0.003 | 164.39734 | 155.761 | 70.484927 | 0.986384 |
| 0.006 | 0.003 | 164.39734 | 155.761 | 70.484927 | 0.986384 |
| 0.015 | 0.0107 | 86.173017 | 86.118 | 38.073055 | 1.292595 |
| 0.077 | 0.0951 | 337.27256 | 140.659 | 61.125623 | 25.96999 |
| 0.077 | 0.0951 | 337.27256 | 140.659 | 61.125623 | 25.96999 |
| 0.077 | 0.0951 | 337.27256 | 140.659 | 61.125623 | 25.96999 |
| 0.077 | 0.0951 | 337.27256 | 140.659 | 61.125623 | 25.96999 |
| 0.077 | 0.0951 | 337.27256 | 140.659 | 61.125623 | 25.96999 |
| 0.077 | 0.0951 | 337.27256 | 140.659 | 61.125623 | 25.96999 |
| 0.077 | 0.0951 | 337.27256 | 140.659 | 61.125623 | 25.96999 |
| 0.011 | 0.0053 | 151.27677 | 86.581 | 38.633434 | 1.664044 |
| 0.011 | 0.0053 | 151.27677 | 86.581 | 38.633434 | 1.664044 |
| 0.004 | 0.0119 | 129.90234 | 97.939 | 31.757433 | 0.519609 |
| 0.004 | 0.0119 | 129.90234 | 97.939 | 31.757433 | 0.519609 |
| 0.004 | 0.0119 | 129.90234 | 97.939 | 31.757433 | 0.519609 |
| 0.004 | 0.0119 | 129.90234 | 97.939 | 31.757433 | 0.519609 |
| 0.006 | 0.0044 | 133.16874 | 85.926 | 35.243385 | 0.799012 |
| 0.006 | 0.0044 | 133.16874 | 85.926 | 35.243385 | 0.799012 |
| 0.006 | 0.0044 | 133.16874 | 85.926 | 35.243385 | 0.799012 |
| 0.005 | 0.0039 | 126.07369 | 113.423 | 42.562929 | 0.630368 |
| 0.005 | 0.0039 | 126.07369 | 113.423 | 42.562929 | 0.630368 |

| pmol PrEST 2 | pmol PrEST 3 | pmol Protein 1 | pmol Protein 2 | pmol Protein 3 |
|---|---|---|---|---|
| 0.785424 | 0.135318 | #VALUE! | #VALUE! | #VALUE! |
| 1.075374 | 0.803852 | #VALUE! | #VALUE! | #VALUE! |
| 1.075374 | 0.803852 | #VALUE! | #VALUE! | #VALUE! |

SUPPLEMENTARY TABLE 2-continued

All identification and quantification information used to quantify proteins.

| | | | | |
|---|---|---|---|---|
| 1.075374 | 0.803852 | 0.505944 | 0.299524 | 0.441515 |
| 0.934566 | 0.211455 | 0.122834 | 0.096531 | 0.543946 |
| 0.934566 | 0.211455 | 0.128161 | #VALUE! | #VALUE! |
| 0.934566 | 0.211455 | #VALUE! | 0.085079 | #VALUE! |
| 0.934566 | 0.211455 | #VALUE! | 0.103428 | #VALUE! |
| 1.29177 | 0.407382 | #VALUE! | #VALUE! | #VALUE! |
| 10.83074 | 5.813047 | 16.56496 | 4.567108 | 7.671478 |
| 10.83074 | 5.813047 | 12.33522 | 4.058713 | 6.374006 |
| 10.83074 | 5.813047 | 6.975019 | 1.983109 | #VALUE! |
| 10.83074 | 5.813047 | 14.06275 | 5.596895 | 7.545916 |
| 10.83074 | 5.813047 | 9.030024 | 3.334677 | 7.323858 |
| 10.83074 | 5.813047 | 12.22407 | 4.936436 | 6.741972 |
| 10.83074 | 5.813047 | 13.37766 | 5.547398 | 7.81506 |
| 0.952391 | 0.204757 | 0.201566 | 0.067086 | #VALUE! |
| 0.952391 | 0.204757 | #VALUE! | 0.07636 | #VALUE! |
| 0.391756 | 0.377913 | 0.495084 | 0.434575 | 0.65345 |
| 0.391756 | 0.377913 | 0.470283 | 0.324268 | 0.725367 |
| 0.391756 | 0.377913 | 0.503522 | 0.480058 | 0.815159 |
| 0.391756 | 0.377913 | #VALUE! | #VALUE! | #VALUE! |
| 0.515556 | 0.155071 | #VALUE! | #VALUE! | #VALUE! |
| 0.515556 | 0.155071 | #VALUE! | #VALUE! | 0.011945 |
| 0.515556 | 0.155071 | 0.028303 | 0.017779 | 0.019655 |
| 0.567115 | 0.165995 | 0.382394 | 0.335352 | #VALUE! |
| 0.567115 | 0.165995 | #VALUE! | 0.246842 | #VALUE! |

| Protein Names | Gene Name | Sequence | SEQ ID NO. | Ratio H/L Mastermix (1) | CV(%) |
|---|---|---|---|---|---|
| Enoyl-CoA hydratase, m | ECHS1 | EGMTAFVEK | 98 | 0.19635 | 13.95 |
| Enoyl-CoA hydratase, m | ECHS1 | ESVNAAFEMTLTEGSK | 99 | 0.14056 | |
| Enoyl-CoA hydratase, m | ECHS1 | ICPVETLVEEAIQCAEK | 100 | 0.22122 | |
| Enoyl-CoA hydratase, m | ECHS1 | ISAQDAK | 101 | NaN | |
| Enoyl-CoA hydratase, m | ECHS1 | IVVAMAK | 102 | 0.15532 | |
| Enoyl-CoA hydratase, m | ECHS1 | KEGMTAFVEK | 103 | NaN | |
| Enoyl-CoA hydratase, m | ECHS1 | KLFYSTFATDDR | 104 | NaN | |
| Enoyl-CoA hydratase, m | ECHS1 | LFYSTFATDDR | 253 | 0.16792 | |
| Enoyl-CoA hydratase, m | ECHS1 | LFYSTFATDDRK | 105 | 0.18416 | |
| Enoyl-CoA hydratase, m | ECHS1 | QAGLVSK | 106 | 0.17537 | |
| Enoyl-CoA hydratase, m | ECHS1 | SLAMEMVLTGDR | 107 | 0.17505 | |
| Eukaryotic translation in | EIF3E | LGHVVMGNNAVSPYQQVIEK | 108 | 3.4941 | 5.39 |
| Eukaryotic translation in | EIF3E | LNMTPEEAER | 109 | NaN | |
| Eukaryotic translation in | EIF3E | SQMLAMNIEK | 110 | 3.2375 | |
| Eukaryotic translation in | EIF3E | WIVNLIR | 111 | NaN | |
| Endoplasmic reticulum l | ERLIN2 | ADAECYTAMK | 112 | 0.42437 | 8.66 |
| Endoplasmic reticulum l | ERLIN2 | DIPNMFMDSAGSVSK | 113 | 0.37141 | |
| Endoplasmic reticulum l | ERLIN2 | LSFGLEDEPLETATK | 114 | 0.34781 | |
| Endoplasmic reticulum l | ERLIN2 | LTPEYLQLMK | 115 | 0.43322 | |
| Endoplasmic reticulum l | ERLIN2 | QFEGLADK | 116 | 0.37105 | |
| Endoplasmic reticulum l | ERLIN2 | VAQVAEITYGQK | 117 | 0.40674 | |
| Fatty acid synthase | FASN | AALQEELQLCK | 118 | 0.87952 | 13.38 |
| Fatty acid synthase | FASN | DPSQQELPR | 119 | 0.80543 | |
| Fatty acid synthase | FASN | FCFTPHTEEGCLSER | 120 | 0.79217 | |
| Fatty acid synthase | FASN | GLVQALQTK | 121 | 0.91099 | |

SUPPLEMENTARY TABLE 2-continued

All identification and quantification information used to quantify proteins.

| Protein Names | Gene Name | Sequence | | | |
|---|---|---|---|---|---|
| Fatty acid synthase | FASN | LLSAACR | 122 | 1.0665 | |
| Fatty acid synthase | FASN | MVVPGLDGAQIPR | 123 | 0.77952 | |
| Fatty acid synthase | FASN | QQEQQVPILEK | 124 | 0.73946 | |
| Fatty acid synthase | FASN | RQQEQQVPILEK | 125 | 0.69837 | |
| Fatty acid synthase | FASN | VTQQGLK | 126 | 0.83488 | |
| Fatty acid synthase | FASN | VTVAGGVHISGLHTESAPR | 127 | 0.71007 | |

| Protein Names | Gene Name | Sequence | Ratio H/L Mastermix (2) | CV(%) | Ratio H/L Mastermix (3) | CV(%) |
|---|---|---|---|---|---|---|
| Enoyl-CoA hydratase, m | ECHS1 | EGMTAFVEK | 0.17962 | 14.70 | 1.3826 | 9.67 |
| Enoyl-CoA hydratase, m | ECHS1 | ESVNAAFEMTLTEGSK | 0.13711 | | 1.0823 | |
| Enoyl-CoA hydratase, m | ECHS1 | ICPVETLVEEAIQCAEK | 0.19149 | | 1.3474 | |
| Enoyl-CoA hydratase, m | ECHS1 | ISAQDAK | NaN | | NaN | |
| Enoyl-CoA hydratase, m | ECHS1 | IVVAMAK | 0.16412 | | NaN | |
| Enoyl-CoA hydratase, m | ECHS1 | KEGMTAFVEK | NaN | | NaN | |
| Enoyl-CoA hydratase, m | ECHS1 | KLFYSTFATDDR | 0.13372 | | NaN | |
| Enoyl-CoA hydratase, m | ECHS1 | LFYSTFATDDR | 0.15756 | | 1.1803 | |
| Enoyl-CoA hydratase, m | ECHS1 | LFYSTFATDDRK | 0.20966 | | 1.1801 | |
| Enoyl-CoA hydratase, m | ECHS1 | QAGLVSK | 0.16861 | | 1.2314 | |
| Enoyl-CoA hydratase, m | ECHS1 | SLAMEMVLTGDR | 0.18633 | | 1.0857 | |
| Eukaryotic translation in | EIF3E | LGHVVMGNNAVSPYQQVIEK | 1.4287 | 19.18 | 1.2643 | 7.57 |
| Eukaryotic translation in | EIF3E | LNMTPEEAER | 1.877 | | 1.431 | |
| Eukaryotic translation in | EIF3E | SQMLAMNIEK | NaN | | NaN | |
| Eukaryotic translation in | EIF3E | WIVNLIR | NaN | | 1.253 | |
| Endoplasmic reticulum 1 | ERLIN2 | ADAECYTAMK | 0.39751 | 10.66 | 1.6231 | 18.18 |
| Endoplasmic reticulum 1 | ERLIN2 | DIPNMFMDSAGSVSK | 0.35448 | | 1.474 | |
| Endoplasmic reticulum 1 | ERLIN2 | LSFGLEDEPLETATK | 0.35101 | | 0.99961 | |
| Endoplasmic reticulum 1 | ERLIN2 | LTPEYLQLMK | 0.44968 | | 1.6324 | |
| Endoplasmic reticulum 1 | ERLIN2 | QFEGLADK | 0.41697 | | 1.5783 | |
| Endoplasmic reticulum 1 | ERLIN2 | VAQVAEITYGQK | NaN | | NaN | |
| Fatty acid synthase | FASN | AALQEELQLCK | 0.79607 | 12.46 | 1.0964 | 15.17 |
| Fatty acid synthase | FASN | DPSQQELPR | NaN | | NaN | |
| Fatty acid synthase | FASN | FCFTPHTEEGCLSER | 0.74449 | | 1.0216 | |
| Fatty acid synthase | FASN | GLVQALQTK | 0.69768 | | 1.262 | |
| Fatty acid synthase | FASN | LLSAACR | NaN | | NaN | |
| Fatty acid synthase | FASN | MVVPGLDGAQIPR | 0.60727 | | 1.1329 | |
| Fatty acid synthase | FASN | QQEQQVPILEK | 0.69517 | | 0.8985 | |
| Fatty acid synthase | FASN | RQQEQQVPILEK | 0.67562 | | 0.87805 | |

SUPPLEMENTARY TABLE 2-continued

All identification and quantification information used to quantify proteins.

| | | | | | |
|---|---|---|---|---|---|
| Fatty acid synthase | FASN | VTQQGLK | | 0.88813 | 1.1698 |
| Fatty acid synthase | FASN | VTVAGGVHISGLHTESAPR | | 0.64471 | 0.82048 |

| µl PrESTs (1 + 2) | µl PrESTs (3) | Exactive pmol/µl 1 | Exactive pmol/µl 2 | Exactive pmol/µl 3 | pmol PrEST 1 |
|---|---|---|---|---|---|
| 0.121 | 0.0495 | 232.98455 | 140.682 | 59.879442 | 28.19113 |
| 0.121 | 0.0495 | 232.98455 | 140.682 | 59.879442 | 28.19113 |
| 0.121 | 0.0495 | 232.98455 | 140.682 | 59.879442 | 28.19113 |
| 0.121 | 0.0495 | 232.98455 | 140.682 | 59.879442 | 28.19113 |
| 0.121 | 0.0495 | 232.98455 | 140.682 | 59.879442 | 28.19113 |
| 0.121 | 0.0495 | 232.98455 | 140.682 | 59.879442 | 28.19113 |
| 0.121 | 0.0495 | 232.98455 | 140.682 | 59.879442 | 28.19113 |
| 0.121 | 0.0495 | 232.98455 | 140.682 | 59.879442 | 28.19113 |
| 0.121 | 0.0495 | 232.98455 | 140.682 | 59.879442 | 28.19113 |
| 0.121 | 0.0495 | 232.98455 | 140.682 | 59.879442 | 28.19113 |
| 0.004 | 0.0325 | 130.83738 | 149.56 | 50.714554 | 0.52335 |
| 0.004 | 0.0325 | 130.83738 | 149.56 | 50.714554 | 0.52335 |
| 0.004 | 0.0325 | 130.83738 | 149.56 | 50.714554 | 0.52335 |
| 0.004 | 0.0325 | 130.83738 | 149.56 | 50.714554 | 0.52335 |
| 0.005 | 0.0032 | 160.39251 | 113.243 | 49.792301 | 0.801963 |
| 0.005 | 0.0032 | 160.39251 | 113.243 | 49.792301 | 0.801963 |
| 0.005 | 0.0032 | 160.39251 | 113.243 | 49.792301 | 0.801963 |
| 0.005 | 0.0032 | 160.39251 | 113.243 | 49.792301 | 0.801963 |
| 0.005 | 0.0032 | 160.39251 | 113.243 | 49.792301 | 0.801963 |
| 0.066 | 0.1232 | 127.7533 | 101.472 | 43.487725 | 8.431718 |
| 0.066 | 0.1232 | 127.7533 | 101.472 | 43.487725 | 8.431718 |
| 0.066 | 0.1232 | 127.7533 | 101.472 | 43.487725 | 8.431718 |
| 0.066 | 0.1232 | 127.7533 | 101.472 | 43.487725 | 8.431718 |
| 0.066 | 0.1232 | 127.7533 | 101.472 | 43.487725 | 8.431718 |
| 0.066 | 0.1232 | 127.7533 | 101.472 | 43.487725 | 8.431718 |
| 0.066 | 0.1232 | 127.7533 | 101.472 | 43.487725 | 8.431718 |
| 0.066 | 0.1232 | 127.7533 | 101.472 | 43.487725 | 8.431718 |
| 0.066 | 0.1232 | 127.7533 | 101.472 | 43.487725 | 8.431718 |

| pmol PrEST 2 | pmol PrEST 3 | pmol Protein 1 | pmol Protein 2 | pmol Protein 3 |
|---|---|---|---|---|
| 17.02252 | 2.964032 | 5.535328 | 3.057585 | 4.098071 |
| 17.02252 | 2.964032 | 3.962545 | 2.333958 | 3.207972 |
| 17.02252 | 2.964032 | 6.236442 | 3.259643 | 3.993737 |
| 17.02252 | 2.964032 | #VALUE! | #VALUE! | #VALUE! |
| 17.02252 | 2.964032 | 4.378646 | 2.793736 | #VALUE! |
| 17.02252 | 2.964032 | #VALUE! | 2.276252 | #VALUE! |
| 17.02252 | 2.964032 | #VALUE! | 2.276252 | #VALUE! |
| 17.02252 | 2.964032 | 4.733855 | 2.682069 | 3.498447 |
| 17.02252 | 2.964032 | 5.191679 | 3.568942 | 3.497855 |
| 17.02252 | 2.964032 | 4.943879 | 2.870167 | 3.649909 |
| 17.02252 | 2.964032 | 4.934857 | 3.171807 | 3.21805 |
| 0.59824 | 1.648223 | 1.828636 | 0.854705 | 2.083848 |
| 0.59824 | 1.648223 | #VALUE! | 1.122896 | 2.358607 |
| 0.59824 | 1.648223 | 1.694344 | #VALUE! | #VALUE! |
| 0.59824 | 1.648223 | #VALUE! | #VALUE! | 2.065223 |
| 0.566215 | 0.159335 | 0.340329 | 0.225076 | 0.258617 |
| 0.566215 | 0.159335 | 0.297857 | 0.200712 | 0.23486 |
| 0.566215 | 0.159335 | 0.278931 | 0.198747 | 0.159273 |
| 0.566215 | 0.159335 | 0.347426 | 0.254616 | 0.260099 |
| 0.566215 | 0.159335 | 0.297568 | 0.236095 | 0.251479 |
| 0.566215 | 0.159335 | 0.232619 | #VALUE! | #VALUE! |
| 6.697152 | 5.357688 | 7.415865 | 5.331402 | 5.874169 |
| 6.697152 | 5.357688 | 6.791159 | #VALUE! | #VALUE! |
| 6.697152 | 5.357688 | 6.679354 | 4.985963 | 5.473414 |
| 6.697152 | 5.357688 | 7.681211 | 4.672469 | 6.761402 |
| 6.697152 | 5.357688 | 8.992427 | #VALUE! | #VALUE! |
| 6.697152 | 5.357688 | 6.572693 | 4.066979 | 6.069724 |
| 6.697152 | 5.357688 | 6.234918 | 4.655659 | 4.813882 |
| 6.697152 | 5.357688 | 5.888459 | 4.52473 | 4.704318 |
| 6.697152 | 5.357688 | 7.039473 | 5.947942 | 6.267423 |
| 6.697152 | 5.357688 | 5.98711 | 4.317721 | 4.395876 |

SUPPLEMENTARY TABLE 2-continued

All identification and quantification information used to quantify proteins.

| Protein Names | Gene Name | Sequence | SEQ ID NO. | Ratio H/L Mastermix (1) | CV(%) |
|---|---|---|---|---|---|
| Flap endonuclease 1 | FEN1 | AVDLIQK | 128 | 0.72265 | 19.67 |
| Flap endonuclease 2 | FEN1 | EQHQLFLEPEVLDPESVELK | 129 | 0.85331 | |
| Flap endonuclease 3 | FEN1 | HLTASEAK | 130 | 0.69703 | |
| Flap endonuclease 4 | FEN1 | LDPNKYPVPENWLHK | 131 | 0.73377 | |
| Flap endonuclease 5 | FEN1 | LPIQEFHLSR | 132 | 0.65281 | |
| Flap endonuclease 6 | FEN1 | SIEEIVR | 133 | 1.1354 | |
| Flap endonuclease 7 | FEN1 | VYAAATEDMDCLTFGSPVLMR | 134 | 0.73515 | |
| Flap endonuclease 8 | FEN1 | YPVPENWLHK | 135 | 0.72303 | |
| Cellular oncogene fos; G | FOS | ELTDTLQAETDQLEDEK | 136 | NaN | — |
| Cellular oncogene fos; G | FOS | GKVEQLSPEEEK | 137 | NaN | |
| Cellular oncogene fos; G | FOS | SALQTEIANLLK | 138 | 0.015533 | |
| Cellular oncogene fos; G | FOS | VEQLSPEEEK | 139 | NaN | |
| Heat shock 70 kDa protein 4 | HSPA4 | EDQYDHLDAADMTK | 140 | 0.2685 | 78.77 |
| Heat shock 70 kDa protein 4 | HSPA4 | LNLQNK | 141 | 0.25909 | |
| Heat shock 70 kDa protein 4 | HSPA4 | NKEDQYDHLDAADMTK | 142 | 0.21899 | |
| Heat shock 70 kDa protein 4 | HSPA4 | QIQQYMK | 143 | 0.95485 | |
| Heat shock 70 kDa protein 4 | HSPA4 | QSLTMDPVVK | 144 | 0.24663 | |
| Heat shock 70 kDa protein 4 | HSPA4 | STNEAMEWMNNK | 145 | 0.25098 | |
| Ras GTPase-activiting-li | IQGAP1 | ILAIGLINEALDEGDAQK | 146 | 0.26959 | 9.98 |
| Ras GTPase-activiting-li | IQGAP1 | LEGVLAEVAQHYQDTLIR | 147 | 0.27809 | |
| Ras GTPase-activiting-li | IQGAP1 | QLSSSVTGLTNIEEENCQR | 148 | 0.27918 | |
| Ras GTPase-activiting-li | IQGAP1 | TLQALQIPAAK | 149 | 0.218 | |
| Ras GTPase-activiting-li | IQGAP1 | YLDELMK | 150 | 0.27889 | |
| Mitogen-activated prote | MAP2K1IP1 | ELAPLFEELR | 151 | 0.32694 | — |
| Mitogen-activated prote | MAP2K1IP2 | KLPSVEGLHAIVVSDR | 152 | NaN | |
| Mitogen-activated prote | MAP2K1IP3 | VANDNAPEHALRPGFLSTFALATI | 153 | NaN | |
| Mixed lineage kinase do | MLKL | APVAIK | 154 | 0.39067 | — |
| 39S ribosomal protein MRPL50 | MRPL50 | AYTPPEDLQSR | 155 | 0.40095 | 2.84 |
| 39S ribosomal protein MRPL50 | MRPL50 | EKEPVVVETVEEK | 156 | 0.41737 | |
| 39S ribosomal protein MRPL50 | MRPL50 | LESYVK | 157 | NaN | |

| Protein Names | Gene Name | Sequence | Ratio H/L Mastermix (2) | CV(%) | Ratio H/L Mastermix (3) | CV(%) |
|---|---|---|---|---|---|---|
| Flap endonuclease 1 | FEN1 | AVDLIQK | 0.74027 | 21.43 | 1.2719 | 10.53 |
| Flap endonuclease 2 | FEN1 | EQHQLFLEPEVLDPESVELK | 0.83635 | | 1.3723 | |
| Flap endonuclease 3 | FEN1 | HLTASEAK | 0.63769 | | 1.0235 | |
| Flap endonuclease 4 | FEN1 | LDPNKYPVPENWLHK | 0.68 | | 1.2048 | |

SUPPLEMENTARY TABLE 2-continued

All identification and quantification information used to quantify proteins.

| Protein | Gene | Peptide | Value 1 | Value 2 | Value 3 | Value 4 | μl PrESTs (1 + 2) | μl PrESTs (3) | Exactive pmol/μl 1 | Exactive pmol/μl 2 | Exactive pmol/μl 3 | pmol PrEST 1 |
|---|---|---|---|---|---|---|---|---|---|---|---|---|
| Flap endonuclease 5 | FEN1 | LPIQEFHLSR | 0.4747 | | 1.0466 | | 0.035 | 0.061 | 155.06238 | 141.409 | 37.29001 | 5.427183 |
| Flap endonuclease 6 | FEN1 | SIEEIVR | NaN | | NaN | | 0.035 | 0.061 | 155.06238 | 141.409 | 37.29001 | 5.427183 |
| Flap endonuclease 7 | FEN1 | VYAAATEDMDCLTFGSPVLMR | 0.45581 | | 1.1345 | | 0.035 | 0.061 | 155.06238 | 141.409 | 37.29001 | 5.427183 |
| Flap endonuclease 8 | FEN1 | YPVPENWLHK | 0.70528 | | 1.1416 | | 0.035 | 0.061 | 155.06238 | 141.409 | 37.29001 | 5.427183 |
| Cellular oncogene fos; G | FOS | ELTDTLQAETDQLEDEK | NaN | 26.11 | NaN | 4.68 | 0.035 | 0.061 | 155.06238 | 141.409 | 37.29001 | 5.427183 |
| Cellular oncogene fos; G | FOS | GKVEQLSPEEEEK | 0.0090707 | | 0.050604 | | 0.035 | 0.061 | 155.06238 | 141.409 | 37.29001 | 5.427183 |
| Cellular oncogene fos; G | FOS | SALQTEIANLLK | 0.013178 | | 0.054066 | | 0.035 | 0.061 | 155.06238 | 141.409 | 37.29001 | 5.427183 |
| Cellular oncogene fos; G | FOS | VEQLSPEEEEK | NaN | | NaN | | 0.035 | 0.061 | 155.06238 | 141.409 | 37.29001 | 5.427183 |
| Heat shock 70 kDa protein 4 | HSPA4 | EDQYDHLDAADMTK | 0.20351 | 7.31 | 0.79843 | 13.41 | 0.007 | 0.0033 | 151.55943 | 141.201 | 52.196632 | 1.060916 |
| Heat shock 70 kDa protein 4 | HSPA4 | LNLQNK | 0.21666 | | 0.94161 | | 0.007 | 0.0033 | 151.55943 | 141.201 | 52.196632 | 1.060916 |
| Heat shock 70 kDa protein 4 | HSPA4 | NKEDQYDHLDAADMTK | 0.21981 | | 0.84382 | | 0.007 | 0.0033 | 151.55943 | 141.201 | 52.196632 | 1.060916 |
| Heat shock 70 kDa protein 4 | HSPA4 | QIQQYMK | NaN | | NaN | | 0.007 | 0.0033 | 151.55943 | 141.201 | 52.196632 | 1.060916 |
| Heat shock 70 kDa protein 4 | HSPA4 | QSLTMDPVVK | 0.22089 | | 0.89363 | | | | | | | |
| Heat shock 70 kDa protein 4 | HSPA4 | STNEAMEWMNNK | 0.24797 | | 1.1176 | | | | | | | |
| Ras GTPase-activiting-li | IQGAP1 | ILAIGLINEALDEGDAQK | 0.27248 | 5.48 | 1.4819 | 6.12 | 0.073 | 0.0447 | 190.231 | 154.209 | 68.382353 | 13.88686 |
| Ras GTPase-activiting-li | IQGAP1 | LEGVLAEVAQHYQDTLIR | 0.273 | | 1.4224 | | 0.073 | 0.0447 | 190.231 | 154.209 | 68.382353 | 13.88686 |
| Ras GTPase-activiting-li | IQGAP1 | QLSSSVTGLTNIEEENCQR | 0.23809 | | 1.4471 | | 0.073 | 0.0447 | 190.231 | 154.209 | 68.382353 | 13.88686 |
| Ras GTPase-activiting-li | IQGAP1 | TLQALQIPAAK | 0.25878 | | 1.5877 | | 0.073 | 0.0447 | 190.231 | 154.209 | 68.382353 | 13.88686 |
| Ras GTPase-activiting-li | IQGAP1 | YLDELMK | 0.26493 | | 1.3441 | | 0.073 | 0.0447 | 190.231 | 154.209 | 68.382353 | 13.88686 |
| Mitogen-activated prote | MAP2K1IP1 | ELAPLFEELR | 0.056059 | — | 1.6953 | 27.91 | | | | | | |
| Mitogen-activated prote | MAP2K1IP2 | KLPSVEGLHAIVVSDR | NaN | | 1.1365 | | | | | | | |
| Mitogen-activated prote | MAP2K1IP3 | VANDNAPEHALRPGFLSTFALATI | NaN | | NaN | | | | | | | |
| Mixed lineage kinase do | MLKL | APVAIK | NaN | — | 0.89538 | — | | | | | | |
| 39S ribosomal protein MRPL50 | MRPL50 | AYTPPEDLQSR | NaN | 5.03 | 1.0384 | 42.41 | | | | | | |
| 39S ribosomal protein MRPL50 | MRPL50 | EKEPVVVETVEEK | 0.67673 | | 2.6456 | | | | | | | |
| 39S ribosomal protein MRPL50 | MRPL50 | LESYVK | 0.63021 | | 2.3002 | | | | | | | |

SUPPLEMENTARY TABLE 2-continued

All identification and quantification information used to quantify proteins.

| | | | | | |
|---|---|---|---|---|---|
| 0.073 | 0.0447 | 190.231 | 154.209 | 68.382353 | 13.88686 |
| 0.109 | 0.054 | 98.606097 | 72.632 | 27.555556 | 10.74806 |
| 0.109 | 0.054 | 98.606097 | 72.632 | 27.555556 | 10.74806 |
| 0.109 | 0.054 | 98.606097 | 72.632 | 27.555556 | 10.74806 |
| 0.109 | 0.054 | 98.606097 | 72.632 | 27.555556 | 10.74806 |
| 0.006 | 0.0033 | 149.10541 | 128.996 | 49.884398 | 0.894632 |
| 0.006 | 0.0033 | 149.10541 | 128.996 | 49.884398 | 0.894632 |
| 0.006 | 0.0033 | 149.10541 | 128.996 | 49.884398 | 0.894632 |
| 0.005 | 0.0048 | 105.25905 | 95.876 | 38.828103 | 0.526295 |
| 0.006 | 0.0042 | 121.96997 | 107.299 | 33.817122 | 0.73182 |
| 0.006 | 0.0042 | 121.96997 | 107.299 | 33.817122 | 0.73182 |
| 0.006 | 0.0042 | 121.96997 | 107.299 | 33.817122 | 0.73182 |

| pmol PrEST 2 | pmol PrEST 3 | pmol Protein 1 | pmol Protein 2 | pmol Protein 3 |
|---|---|---|---|---|
| 4.494315 | 2.274691 | 3.921954 | 3.663829 | 2.893179 |
| 4.494315 | 2.274691 | 4.63107 | 4.13936 | 3.121558 |
| 4.494315 | 2.274691 | 3.78291 | 3.156129 | 2.328146 |
| 4.494315 | 2.274691 | 3.982304 | 3.365534 | 2.740547 |
| 4.494315 | 2.274691 | 3.54292 | 2.34944 | 2.380691 |
| 4.494315 | 2.274691 | 6.162024 | #VALUE! | #VALUE! |
| 4.494315 | 2.274691 | 3.989794 | 2.255947 | 2.580637 |
| 4.494315 | 2.274691 | 3.924016 | 3.490653 | 2.596787 |
| 0.988407 | 0.172249 | #VALUE! | #VALUE! | #VALUE! |
| 0.988407 | 0.172249 | #VALUE! | 0.008966 | 0.008716 |
| 0.988407 | 0.172249 | 0.016479 | 0.013025 | 0.009313 |
| 0.988407 | 0.172249 | #VALUE! | #VALUE! | #VALUE! |
| 11.25726 | 3.056691 | 3.728623 | 2.290964 | 2.440554 |
| 11.25726 | 3.056691 | 3.597947 | 2.438997 | 2.878211 |
| 11.25726 | 3.056691 | 3.041084 | 2.474458 | 2.579297 |
| 11.25726 | 3.056691 | 13.25987 | #VALUE! | #VALUE! |
| 11.25726 | 3.056691 | 3.424917 | 2.486615 | 2.731551 |
| 11.25726 | 3.056691 | 3.485325 | 2.791462 | 3.416158 |
| 7.916888 | 1.488 | 2.897571 | 2.157194 | 2.205067 |
| 7.916888 | 1.488 | 2.988929 | 2.16131 | 2.116531 |
| 7.916888 | 1.488 | 3.000645 | 1.884932 | 2.153285 |
| 7.916888 | 1.488 | 2.343078 | 2.048732 | 2.362498 |
| 7.916888 | 1.488 | 2.997528 | 2.097421 | 2.000021 |
| 0.773976 | 0.164619 | 0.292491 | 0.043388 | 0.279078 |
| 0.773976 | 0.164619 | #VALUE! | #VALUE! | 0.187089 |
| 0.773976 | 0.164619 | #VALUE! | #VALUE! | #VALUE! |
| 0.47938 | 0.186375 | 0.205608 | #VALUE! | 0.166876 |
| 0.643794 | 0.142032 | 0.293423 | #VALUE! | 0.147486 |
| 0.643794 | 0.142032 | 0.30544 | 0.435675 | 0.37576 |
| 0.643794 | 0.142032 | #VALUE! | 0.405725 | 0.326702 |

| Protein Names | Gene Name | Sequence | SEQ ID NO. | Ratio H/L Mastermix (1) | CV(%) |
|---|---|---|---|---|---|
| 28S ribosomal protein S23 | MRPS23 | ALLAEGVILR | 158 | 0.33211 | 7.87 |
| 28S ribosomal protien S23 | MRPS23 | LGETDEEK | 159 | 0.31151 | |
| 28S ribosomal protein S23 | MRPS23 | TQHGGSHVSR | 160 | 0.36147 | |
| 28S ribosomal protein S23 | MRPS23 | YTELQK | 161 | 0.30384 | |
| 28S ribosomal protein S28 | MRPS28 | AGGFASALER | 162 | 0.79424 | 28.44 |
| 28S ribosomal protein S28 | MRPS28 | HSELLQK | 163 | 0.48648 | |
| 28S ribosomal protein S28 | MRPS28 | NVESFASMLR | 164 | 0.87278 | |
| Purine nucleoside phosp | NP | ACVMMQGR | 165 | 0.65455 | 25.15 |
| Purine nucleoside phosp | NP | DHINLPGFSGQNPLR | 166 | 0.57033 | |
| Purine nucleoside phosp | NP | FEVGDIMLIR | 167 | 0.56081 | |
| Purine nucleoside phosp | NP | FHMYEGYPLWK | 168 | 0.58408 | |
| Purine nucleoside phosp | NP | HRPQVAIICGSGLGGLTDK | 169 | NaN | |
| Purine nucleoside phosp | NP | LTQAQIFDYGEIPNFPR | 170 | 0.26064 | |

SUPPLEMENTARY TABLE 2-continued

All identification and quantification information used to quantify proteins.

| Protein Names | Gene Name | Sequence | | | |
|---|---|---|---|---|---|
| Purine nucleoside phosp | NP | STVPGHAGR | 171 | 0.54236 | |
| Purine nucleoside phosp | NP | VFHLLGVDTLVVTNAAGGLNPK | 172 | 0.68813 | |
| Poly [ADP-ribose] polym | PARP4 | ADLCQLIR | 173 | 0.18498 | 49.36 |
| Poly [ADP-ribose] polym | PARP4 | AEGILLLVK | 174 | NaN | |
| Poly [ADP-ribose] polym | PARP4 | EVNLGLLAK | 175 | 0.089268 | |
| Prefoldin subunit 1 | PFDN1 | EAEDNIR | 176 | NaN | 2.89 |
| Prefoldin subunit 1 | PFDN1 | EAIHSQLLEK | 177 | 0.17447 | |
| Prefoldin subunit 1 | PFDN1 | IKELEQK | 178 | NaN | |
| Prefoldin subunit 1 | PFDN1 | LADIQIEQLNR | 179 | 0.18176 | |
| Prefoldin subunit 1 | PFDN1 | MFILQSK | 180 | NaN | |
| Peptidyl-prolyl cis-trans | PPIB | DKPLKDVIIADCGK | 181 | 0.47962 | 7.94 |
| Peptidyl-prolyl cis-trans | PPIB | DTNGSQFFITTVK | 182 | 0.50189 | |
| Peptidyl-prolyl cis-trans | PPIB | DVIIADCGK | 183 | 0.5755 | |
| Peptidyl-prolyl cis-trans | PPIB | IEVEKPFAIAK | 184 | 0.46154 | |
| Peptidyl-prolyl cis-trans | PPIB | TAWLDGK | 185 | 0.49743 | |
| Peptidyl-prolyl cis-trans | PPIB | VLEGMEVVR | 186 | 0.48337 | |

| Protein Names | Gene Name | Sequence | Ratio H/L Mastermix (2) | CV(%) | Ratio H/L Mastermix (3) | CV(%) |
|---|---|---|---|---|---|---|
| 28S ribosomal protein S23 | MRPS23 | ALLAEGVILR | 0.30866 | 51.08 | 2.8825 | 3.38 |
| 28S ribosomal protein S23 | MRPS23 | LGETDEEK | 0.33385 | | 2.7777 | |
| 28S ribosomal protein S23 | MRPS23 | TQHGGSHVSR | 0.061638 | | 2.6945 | |
| 28S ribosomal protein S23 | MRPS23 | YTELQK | 0.3357 | | NaN | |
| 28S ribosomal protein S23 | MRPS28 | AGGFASALER | 0.59711 | 14.13 | NaN | 11.34 |
| 28S ribosomal protein S23 | MRPS28 | HSELLQK | 0.62859 | | 1.2025 | |
| 28S ribosomal protein S23 | MRPS28 | NVESFASMLR | 0.77368 | | 1.4122 | |
| Purine nucleoside phosp | NP | ACVMMQGR | 0.63682 | 21.02 | 0.89372 | 8.08 |
| Purine nucleoside phosp | NP | DHINLPGFSGQNPLR | 0.47254 | | 0.98592 | |
| Purine nucleoside phosp | NP | FEVGDIMLIR | 0.55235 | | 0.98611 | |
| Purine nucleoside phosp | NP | FHMYEGYPLWK | 0.57218 | | 0.85084 | |
| Purine nucleoside phosp | NP | HRPQVAIICGSGLGGLTDK | 0.50154 | | 0.84573 | |
| Purine nucleoside phosp | NP | LTQAQIFDYGEIPNFPR | 0.27356 | | NaN | |
| Purine nucleoside phosp | NP | STVPGHAGR | 0.51975 | | 0.79355 | |
| Purine nucleoside phosp | NP | VFHLLGVDTLVVTNAAGGLNPK | 0.51622 | | 0.88994 | |
| Poly [ADP-ribose] polym | PARP4 | ADLCQLIR | 0.18395 | 6.50 | NaN | — |
| Poly [ADP-ribose] polym | PARP4 | AEGILLLVK | NaN | | NaN | |
| Poly [ADP-ribose] polym | PARP4 | EVNLGLLAK | 0.16778 | | NaN | |
| Prefoldin subunit 1 | PFDN1 | EAEDNIR | NaN | 12.33 | NaN | 8.38 |
| Prefoldin subunit 1 | PFDN1 | EAIHSQLLEK | 0.1967 | | 1.8144 | |

SUPPLEMENTARY TABLE 2-continued

All identification and quantification information used to quantify proteins.

| Protein | Gene | Peptide | Value 1 | Value 2 | Value 3 | Value 4 |
|---|---|---|---|---|---|---|
| Prefoldin subunit 1 | PFDN1 | IKELEQK | NaN | | NaN | |
| Prefoldin subunit 1 | PFDN1 | LADIQIEQLNR | 0.16018 | | 1.6113 | |
| Prefoldin subunit 1 | PFDN1 | MFILQSK | 0.20263 | | NaN | |
| Peptidyl-prolyl cis-trans | PPIB | DKPLKDVIIADCGK | 0.41764 | 7.16 | 1.0739 | 7.51 |
| Peptidyl-prolyl cis-trans | PPIB | DTNGSQFFITTVK | 0.47562 | | 1.2206 | |
| Peptidyl-prolyl cis-trans | PPIB | DVIIADCGK | 0.51014 | | 1.3142 | |
| Peptidyl-prolyl cis-trans | PPIB | IEVEKPFAIAK | 0.453 | | 1.1893 | |
| Peptidyl-prolyl cis-trans | PPIB | TAWLDGK | 0.49432 | | 1.2376 | |
| Peptidyl-prolyl cis-trans | PPIB | VLEGMEVVR | 0.49474 | | 1.3259 | |

| µl PrESTs (1 + 2) | µl PrESTs (3) | Exactive pmol/µl 1 | Exactive pmol/µl 2 | Exactive pmol/µl 3 | pmol PrEST 1 | pmol PrEST 2 | pmol PrEST 3 | pmol Protein 1 | pmol Protein 2 | pmol Protein 3 |
|---|---|---|---|---|---|---|---|---|---|---|
| 0.006 | 0.0024 | 198.09216 | 181.075 | 69.643134 | 1.188553 | 1.08645 | 0.167144 | 0.39473 | 0.335344 | 0.481791 |
| 0.006 | 0.0024 | 198.09216 | 181.075 | 69.643134 | 1.188553 | 1.08645 | 0.167144 | 0.370246 | 0.362711 | 0.464275 |
| 0.006 | 0.0024 | 198.09216 | 181.075 | 69.643134 | 1.188553 | 1.08645 | 0.167144 | 0.429626 | 0.066967 | 0.450368 |
| 0.006 | 0.0024 | 198.09216 | 181.075 | 69.643134 | 1.188553 | 1.08645 | 0.167144 | 0.36113 | 0.364721 | #VALUE! |
| 0.005 | 0.0081 | 191.91632 | 145.872 | 66.25803 | 0.959582 | 0.72936 | 0.53669 | 0.762138 | 0.435508 | #VALUE! |
| 0.005 | 0.0081 | 191.91632 | 145.872 | 66.25803 | 0.959582 | 0.72936 | 0.53669 | 0.466817 | 0.458468 | 0.64537 |
| 0.005 | 0.0081 | 191.91632 | 145.872 | 66.25803 | 0.959582 | 0.72936 | 0.53669 | 0.837504 | 0.564291 | 0.757914 |
| 0.055 | 0.0864 | 112.22478 | 79.837 | 33.590734 | 6.172363 | 4.391035 | 2.902239 | 4.04012 | 2.796299 | 2.593789 |
| 0.055 | 0.0864 | 112.22478 | 79.837 | 33.590734 | 6.172363 | 4.391035 | 2.902239 | 3.520284 | 2.07494 | 2.861376 |
| 0.055 | 0.0864 | 112.22478 | 79.837 | 33.590734 | 6.172363 | 4.391035 | 2.902239 | 3.461523 | 2.425388 | 2.861927 |
| 0.055 | 0.0864 | 112.22478 | 79.837 | 33.590734 | 6.172363 | 4.391035 | 2.902239 | 3.605154 | 2.512462 | 2.469341 |
| 0.055 | 0.0864 | 112.22478 | 79.837 | 33.590734 | 6.172363 | 4.391035 | 2.902239 | #VALUE! | 2.20228 | 2.454511 |
| 0.055 | 0.0864 | 112.22478 | 79.837 | 33.590734 | 6.172363 | 4.391035 | 2.902239 | 1.608765 | 1.201212 | #VALUE! |
| 0.055 | 0.0864 | 112.22478 | 79.837 | 33.590734 | 6.172363 | 4.391035 | 2.902239 | 3.347643 | 2.28224 | 2.303072 |
| 0.055 | 0.0864 | 112.22478 | 79.837 | 33.590734 | 6.172363 | 4.391035 | 2.902239 | 4.247388 | 2.26674 | 2.582819 |
| 0.005 | 0.0037 | 144.98538 | 124.938 | 55.100415 | 0.724927 | 0.62469 | 2.203872 | 0.134097 | 0.114912 | #VALUE! |
| 0.005 | 0.0037 | 144.98538 | 124.938 | 55.100415 | 0.724927 | 0.62469 | 2.203872 | #VALUE! | #VALUE! | #VALUE! |
| 0.005 | 0.0037 | 144.98538 | 124.938 | 55.100415 | 0.724927 | 0.62469 | 2.203872 | 0.064713 | 0.10481 | #VALUE! |
| 0.023 | 0.0071 | 193.04964 | 191.964 | 33.110306 | 4.440142 | 4.415172 | 0.235083 | #VALUE! | #VALUE! | #VALUE! |
| 0.023 | 0.0071 | 193.04964 | 191.964 | 33.110306 | 4.440142 | 4.415172 | 0.235083 | 0.774672 | 0.868464 | 0.426535 |
| 0.023 | 0.0071 | 193.04964 | 191.964 | 33.110306 | 4.440142 | 4.415172 | 0.235083 | #VALUE! | #VALUE! | #VALUE! |
| 0.023 | 0.0071 | 193.04964 | 191.964 | 33.110306 | 4.440142 | 4.415172 | 0.235083 | 0.80704 | 0.707222 | 0.37879 |
| 0.023 | 0.0071 | 193.04964 | 191.964 | 33.110306 | 4.440142 | 4.415172 | 0.235083 | #VALUE! | 0.894646 | #VALUE! |
| 0.531 | 0.6195 | 99.552439 | 58.765 | 22.904459 | 52.86234 | | | | | |
| 0.531 | 0.6195 | 99.552439 | 58.765 | 22.904459 | 52.86234 | | | | | |
| 0.531 | 0.6195 | 99.552439 | 58.765 | 22.904459 | 52.86234 | | | | | |
| 0.531 | 0.6195 | 99.552439 | 58.765 | 22.904459 | 52.86234 | | | | | |
| 0.531 | 0.6195 | 99.552439 | 58.765 | 22.904459 | 52.86234 | | | | | |
| 0.531 | 0.6195 | 99.552439 | 58.765 | 22.904459 | 52.86234 | | | | | |

SUPPLEMENTARY TABLE 2-continued

All identification and quantification information used to quantify proteins.

| | | | | |
|---|---|---|---|---|
| 31.20422 | 14.18931 | 25.35384 | 13.03213 | 15.2379 |
| 31.20422 | 14.18931 | 26.53108 | 14.84135 | 17.31947 |
| 31.20422 | 14.18931 | 30.42228 | 15.91852 | 18.64759 |
| 31.20422 | 14.18931 | 24.39809 | 14.13551 | 16.87535 |
| 31.20422 | 14.18931 | 26.29532 | 15.42487 | 17.56069 |
| 31.20422 | 14.18931 | 25.55207 | 15.43797 | 18.81361 |

| Protein Names | Gene Name | Sequence | SEQ ID NO. | Ratio H/L Mastermix (1) | CV(%) |
|---|---|---|---|---|---|
| Peroxiredoxin 6 | PRDX6 | DFTPVCTTELGR | 187 | 0.70188 | 6.96 |
| Peroxiredoxin 6 | PRDX6 | DINAYNCEEPTEK | 188 | 0.75055 | |
| Peroxiredoxin 6 | PRDX6 | ELAILLGMLDPAEK | 189 | 0.77082 | |
| Peroxiredoxin 6 | PRDX6 | ELAILLGMLDPAEKDEK | 190 | 0.62879 | |
| Peroxiredoxin 6 | PRDX6 | FHDFLGDSWGILFSHPR | 191 | NaN | |
| Peroxiredoxin 6 | PRDX6 | GMPVTAR | 192 | 0.71311 | |
| Peroxiredoxin 6 | PRDX6 | LAPEFAK | 193 | 0.73135 | |
| Peroxiredoxin 6 | PRDX6 | LIALSIDSVEDHLAWSK | 194 | 0.72068 | |
| Peroxiredoxin 6 | PRDX6 | LPFPIIDDR | 195 | 0.74256 | |
| Peroxiredoxin 6 | PRDX6 | VVFVFGPDK | 196 | 0.6815 | |
| Peroxiredoxin 6 | PRDX6 | VVFVFGPDKK | 197 | 0.81434 | |
| 26S protease regulatory | PSMC3 | AVCVEAGMIALR | 198 | 0.89983 | 24.43 |
| 26S protease regulatory | PSMC3 | GATELTHEDYMEGILEVQAK | 199 | NaN | |
| 26S protease regulatory | PSMC3 | IMQIHSR | 200 | 0.58166 | |
| 26S protease regulatory | PSMC3 | MNVSPDVNYEELAR | 201 | 0.62842 | |
| 14-3-3 protein sigma | SFN | IIDSAR | 202 | NaN | 7.23 |
| 14-3-3 protein sigma | SFN | SAYQEAMDISK | 203 | 0.41269 | |
| 14-3-3 protein sigma | SFN | SNEEGSEEKGPEVR | 204 | 0.3446 | |
| 14-3-3 protein sigma | SFN | VETELQGVCDTVLGLLDSHLIK | 205 | NaN | |
| 14-3-3 protein sigma | SFN | VLSSIEQK | 206 | 0.39497 | |
| 14-3-3 protein sigma | SFN | YLAEVATGDDK | 207 | 0.41281 | |
| 14-3-3 protein sigma | SFN | YLAEVATGDDKK | 208 | 0.404 | |
| FACT complex subunit SSRP | SSRP1 | ADVIQATGDAICIFR | 209 | 0.85761 | 3.66 |
| FACT complex subunit SSRP | SSRP2 | ELQCLTPR | 210 | 0.90583 | |
| FACT complex subunit SSRP | SSRP3 | IPYTTVLR | 211 | 0.84574 | |
| FACT complex subunit SSRP | SSRP4 | LFLLPHK | 212 | NaN | |
| THO complex subunit 1 | THOC1 | AVNNSNYGWR | 213 | 0.43053 | 26.28 |
| THO complex subunit 1 | THOC1 | LWNLCPDNMEACK | 214 | 0.55515 | |
| THO complex subunit 1 | THOC1 | SLPEYLENMVIK | 215 | 0.50412 | |
| THO complex subunit 1 | THOC1 | TGEDEDEEDNDALLK | 216 | 0.28678 | |
| Nucleoprotein TPR | TPR | ILLSQTTGVAIPLHASSLDDVSLASTPK | 257 | 0.1447 | 7.15 |
| Nucleoprotein TPR | TPR | ITELQLK | 217 | 0.17454 | |

SUPPLEMENTARY TABLE 2-continued

All identification and quantification information used to quantify proteins.

| Protein Names | Gene Name | Sequence | Ratio H/L Mastermix (2) | CV(%) | Ratio H/L Mastermix (3) | CV(%) |
|---|---|---|---|---|---|---|
| Peroxiredoxin 6 | PRDX6 | DFTPVCTTELGR | 0.68855 | 7.92 | 0.98276 | 9.15 |
| Peroxiredoxin 6 | PRDX6 | DINAYNCEEPTEK | 0.74788 | | 1.1286 | |
| Peroxiredoxin 6 | PRDX6 | ELAILLGMLDPAEK | 0.61275 | | 1.2449 | |
| Peroxiredoxin 6 | PRDX6 | ELAILLGMLDPAEKDEK | 0.65579 | | 1.2636 | |
| Peroxiredoxin 6 | PRDX6 | FHDFLGDSWGILFSHPR | 0.78925 | | NaN | |
| Peroxiredoxin 6 | PRDX6 | GMPVTAR | 0.79113 | | 1.0751 | |
| Peroxiredoxin 6 | PRDX6 | LAPEFAK | 0.65758 | | 1.1849 | |
| Peroxiredoxin 6 | PRDX6 | LIALSIDSVEDHLAWSK | 0.73169 | | 1.1426 | |
| Peroxiredoxin 6 | PRDX6 | LPFPIIDDR | 0.74049 | | 1.1585 | |
| Peroxiredoxin 6 | PRDX6 | VVFVFGPDK | 0.74577 | | 1.1822 | |
| Peroxiredoxin 6 | PRDX6 | VVFVFGPDKK | 0.72122 | | 0.94586 | |
| 26S protease regulatory | PSMC3 | AVCVEAGMIALR | 0.51761 | 10.16 | NaN | — |
| 26S protease regulatory | PSMC3 | GATELTHEDYMEGILEVQAK | NaN | | NaN | |
| 26S protease regulatory | PSMC3 | IMQIHSR | 0.60039 | | NaN | |
| 26S protease regulatory | PSMC3 | MNVSPDVNYEELAR | 0.63254 | | 1.0965 | |
| 14-3-3 protein sigma | SFN | IIDSAR | NaN | 8.77 | NaN | 16.05 |
| 14-3-3 protein sigma | SFN | SAYQEAMDISK | 0.41814 | | 1.1131 | |
| 14-3-3 protein sigma | SFN | SNEEGSEEKGPEVR | 0.35575 | | 0.75982 | |
| 14-3-3 protein sigma | SFN | VETELQGVCDTVLGLLDSHLIK | 0.43773 | | NaN | |
| 14-3-3 protein sigma | SFN | VLSSIEQK | 0.35675 | | 0.87046 | |
| 14-3-3 protein sigma | SFN | YLAEVATGDDK | 0.38665 | | 0.98489 | |
| 14-3-3 protein sigma | SFN | YLAEVATGDDKK | 0.41942 | | 0.79403 | |
| FACT complex subunit SSRP | SSRP1 | ADVIQATGDAICIFR | 0.73149 | 6.06 | 1.1277 | 5.26 |
| FACT complex subunit SSRP | SSRP2 | ELQCLTPR | 0.73695 | | 1.2494 | |
| FACT complex subunit SSRP | SSRP3 | IPYTTVLR | 0.79479 | | 1.2167 | |
| FACT complex subunit SSRP | SSRP4 | LFLLPHK | 0.68587 | | NaN | |
| THO complex subunit 1 | THOC1 | AVNNSNYGWR | 0.34141 | 24.03 | NaN | 43.19 |
| THO complex subunit 1 | THOC1 | LWNLCPDNMEACK | 0.38786 | | 2.8589 | |
| THO complex subunit 1 | THOC1 | SLPEYLENMVIK | 0.38951 | | 2.9525 | |
| THO complex subunit 1 | THOC1 | TGEDEDEEDNDALLK | 0.21856 | | 1.1674 | |
| Nucleoprotein TPR | TPR | ILLSQTTGVAIPLHASSLDDVSLASTPK | 0.16851 | 10.98 | NaN | 16.59 |
| Nucleoprotein TPR | TPR | ITELQLK | 0.16679 | | 1.6804 | |

| µl PrESTs (1 + 2) | µl PrESTs (3) | Exactive pmol/µl 1 | Exactive pmol/µl 2 | Exactive pmol/µl 3 | pmol PrEST 1 |
|---|---|---|---|---|---|
| 0.202 | 0.3388 | 100.65311 | 94.21 | 37.403786 | 20.33193 |
| 0.202 | 0.3388 | 100.65311 | 94.21 | 37.403786 | 20.33193 |
| 0.202 | 0.3388 | 100.65311 | 94.21 | 37.403786 | 20.33193 |
| 0.202 | 0.3388 | 100.65311 | 94.21 | 37.403786 | 20.33193 |
| 0.202 | 0.3388 | 100.65311 | 94.21 | 37.403786 | 20.33193 |

SUPPLEMENTARY TABLE 2-continued

All identification and quantification information used to quantify proteins.

| | | | | | |
|---|---|---|---|---|---|
| 0.202 | 0.3388 | 100.65311 | 94.21 | 37.403786 | 20.33193 |
| 0.202 | 0.3388 | 100.65311 | 94.21 | 37.403786 | 20.33193 |
| 0.202 | 0.3388 | 100.65311 | 94.21 | 37.403786 | 20.33193 |
| 0.202 | 0.3388 | 100.65311 | 94.21 | 37.403786 | 20.33193 |
| 0.202 | 0.3388 | 100.65311 | 94.21 | 37.403786 | 20.33193 |
| 0.202 | 0.3388 | 100.65311 | 94.21 | 37.403786 | 20.33193 |
| 0.017 | 0.0294 | 167.07191 | 156.456 | 61.444877 | 2.840222 |
| 0.017 | 0.0294 | 167.07191 | 156.456 | 61.444877 | 2.840222 |
| 0.017 | 0.0294 | 167.07191 | 156.456 | 61.444877 | 2.840222 |
| 0.017 | 0.0294 | 167.07191 | 156.456 | 61.444877 | 2.840222 |
| 0.096 | 0.102 | 100.90731 | 80.163 | 30.014189 | 9.687101 |
| 0.096 | 0.102 | 100.90731 | 80.163 | 30.014189 | 9.687101 |
| 0.096 | 0.102 | 100.90731 | 80.163 | 30.014189 | 9.687101 |
| 0.096 | 0.102 | 100.90731 | 80.163 | 30.014189 | 9.687101 |
| 0.096 | 0.102 | 100.90731 | 80.163 | 30.014189 | 9.687101 |
| 0.096 | 0.102 | 100.90731 | 80.163 | 30.014189 | 9.687101 |
| 0.017 | 0.0343 | 128.21107 | 139.714 | 48.156415 | 2.179588 |
| 0.017 | 0.0343 | 128.21107 | 139.714 | 48.156415 | 2.179588 |
| 0.017 | 0.0343 | 128.21107 | 139.714 | 48.156415 | 2.179588 |
| 0.017 | 0.0343 | 128.21107 | 139.714 | 48.156415 | 2.179588 |
| 0.006 | 0.0036 | 133.17121 | 131.715 | 33.493744 | 0.799027 |
| 0.006 | 0.0036 | 133.17121 | 131.715 | 33.493744 | 0.799027 |
| 0.006 | 0.0036 | 133.17121 | 131.715 | 33.493744 | 0.799027 |
| 0.006 | 0.0036 | 133.17121 | 131.715 | 33.493744 | 0.799027 |
| 0.021 | 0.0086 | 186.99624 | 129.566 | 51.550628 | 3.926921 |
| 0.021 | 0.0086 | 186.99624 | 129.566 | 51.550628 | 3.926921 |

| | pmol PrEST 2 | pmol PrEST 3 | pmol Protein 1 | pmol Protein 2 | pmol Protein 3 |
|---|---|---|---|---|---|
| | 19.03042 | 12.6724 | 14.27057 | 13.1034 | 12.45393 |
| | 19.03042 | 12.6724 | 15.26013 | 14.23247 | 14.30207 |
| | 19.03042 | 12.6724 | 15.67226 | 11.66089 | 15.77587 |
| | 19.03042 | 12.6724 | 12.78451 | 12.47996 | 16.01285 |
| | 19.03042 | 12.6724 | #VALUE! | 15.01976 | #VALUE! |
| | 19.03042 | 12.6724 | 14.4989 | 15.05554 | 13.6241 |
| | 19.03042 | 12.6724 | 14.86976 | 12.51402 | 15.01553 |
| | 19.03042 | 12.6724 | 14.65281 | 13.92437 | 14.47949 |
| | 19.03042 | 12.6724 | 15.09768 | 14.09184 | 14.68098 |
| | 19.03042 | 12.6724 | 13.85621 | 14.19232 | 14.98131 |
| | 19.03042 | 12.6724 | 16.5571 | 13.72512 | 11.98632 |
| | 2.659752 | 1.806479 | 2.555717 | 1.376714 | #VALUE! |
| | 2.659752 | 1.806479 | #VALUE! | #VALUE! | #VALUE! |
| | 2.659752 | 1.806479 | 1.652044 | 1.596889 | #VALUE! |
| | 2.659752 | 1.806479 | 1.784853 | 1.6824 | 1.980805 |
| | 7.695648 | 3.061447 | #VALUE! | #VALUE! | #VALUE! |
| | 7.695648 | 3.061447 | 3.99777 | 3.217858 | 3.407697 |
| | 7.695648 | 3.061447 | 3.338175 | 2.737727 | 2.326149 |
| | 7.695648 | 3.061447 | #VALUE! | 3.368616 | #VALUE! |
| | 7.695648 | 3.061447 | 3.826114 | 2.745422 | 2.664867 |
| | 7.695648 | 3.061447 | 3.998932 | 2.975522 | 3.015189 |
| | 7.695648 | 3.061447 | 3.913589 | 3.227709 | 2.430881 |
| | 2.375138 | 1.651765 | 1.869237 | 1.73739 | 1.862695 |
| | 2.375138 | 1.651765 | 1.974336 | 1.750358 | 2.063715 |
| | 2.375138 | 1.651765 | 1.843365 | 1.887736 | 2.009703 |
| | 2.375138 | 1.651765 | #VALUE! | 1.629036 | #VALUE! |
| | 0.79029 | 0.120577 | 0.344005 | 0.269813 | #VALUE! |
| | 0.79029 | 0.120577 | 0.44358 | 0.306522 | 0.344719 |
| | 0.79029 | 0.120577 | 0.402806 | 0.307826 | 0.356005 |
| | 0.79029 | 0.120577 | 0.229145 | 0.172726 | 0.140762 |
| | 2.720886 | 0.443335 | 0.568225 | 0.458496 | #VALUE! |
| | 2.720886 | 0.443335 | 0.685405 | 0.453817 | 0.744981 |

| Protein Names | Gene Name | Sequence | SEQ ID NO. | Ratio H/L Mastermix (1) | CV(%) |
|---|---|---|---|---|---|
| Nucleoprotein TPR | TPR | LESALTELEQLR | 218 | 0.1666 | |
| Nucleoprotein TPR | TPR | LESALTELEQLRK | 219 | 0.17493 | |
| Nucleoprotein TPR | TPR | NIEELQQQNQR | 220 | 0.17718 | |
| Nucleoprotein TPR | TPR | QHQMQLVDSIVR | 221 | 0.16848 | |
| Cytochrome b-c1 complex s | UQCRC1 | ADLTEYLSTHYK | 222 | 1.6066 | 5.68 |

SUPPLEMENTARY TABLE 2-continued

All identification and quantification information used to quantify proteins.

| Protein Names | Gene Name | Sequence | | | |
|---|---|---|---|---|---|
| Cytochrome b-c1 complex s | UQCRC1 | DVVFNYLHATAFQGTPLAQAVTC | 258 | 1.524 | |
| Cytochrome b-c1 complex s | UQCRC1 | MVLAAAGGVEHQQLLDLAQK | 223 | 1.707 | |
| Transitional endoplasmi | VCP | DHFEEAMR | 224 | 0.20879 | 29.20 |
| Transitional endoplasmi | VCP | ESIESEIR | 225 | 0.075211 | |
| Transitional endoplasmi | VCP | GFGSFR | 226 | 0.21737 | |
| Transitional endoplasmi | VCP | KYEMFAQTLQQSR | 227 | 0.12676 | |
| Transitional endoplasmi | VCP | MTNGFSGADLTEICQR | 228 | 0.23492 | |
| Transitional endoplasmi | VCP | QTNPSAMEVEEDDPVPEIR | 229 | 0.14391 | |
| Transitional endoplasmi | VCP | RDHFEEAMR | 230 | 0.20524 | |
| Transitional endoplasmi | VCP | SVSDNDIR | 231 | 0.19148 | |
| Transitional endoplasmi | VCP | YEMFAQTLQQSR | 232 | 0.20698 | |
| Vimentin | VIM | DNLAEDIMR | 233 | 0.813 | 15.32 |
| Vimentin | VIM | EEAENTLQSFR | 234 | 0.78127 | |
| Vimentin | VIM | EKLQEEMLQR | 235 | NaN | |
| Vimentin | VIM | ILLAELEQIK | 236 | 0.7214 | |
| Vimentin | VIM | ILLAELEQLKGQGK | 237 | 0.7299 | |
| Vimentin | VIM | LGDLYEEEMR | 238 | 0.52115 | |
| Vimentin | VIM | LQEEMLQR | 239 | 0.87912 | |
| Vimentin | VIM | QDVDNASIAR | 240 | 0.82023 | |
| Vimentin | VIM | QVDQLTNDK | 241 | 0.79102 | |
| Vimentin | VIM | RQVDQLTNDK | 242 | 0.84806 | |
| Vimentin | VIM | VEVERDNLAEDIMR | 243 | 0.58525 | |
| Female-lethal(2)D homo | WTAP | EGNTTEDDFPSSPGNGNK | 244 | NaN | |
| Female-lethal(2)D homo | WTAP | LTNGPSNGSSSR | 245 | NaN | |
| Female-lethal(2)D homo | WTAP | QQLAQYQQQQSQASAPSTSR | 246 | 0.05126 | |
| Female-lethal(2)D homo | WTAP | TSGSGFHR | 247 | NaN | |

| Protein Names | Gene Name | Sequence | Ratio H/L Mastermix (2) | CV(%) | Ratio H/L Mastermix (3) | CV(%) |
|---|---|---|---|---|---|---|
| Nucleoprotein TPR | TPR | LESALTELEQLR | 0.15943 | | 1.1901 | |
| Nucleoprotein TPR | TPR | LESALTELEQLRK | 0.17872 | | 1.3357 | |
| Nucleoprotein TPR | TPR | NIEELQQQNQR | 0.18774 | | 1.3128 | |
| Nucleoprotein TPR | TPR | QHQMQLVDSIVR | 0.21389 | | 1.7312 | |
| Cytochrome b-c1 complex s | UQCRC1 | ADLTEYLSTHYK | 1.5721 | 5.68 | 1.3068 | 12.57 |
| Cytochrome b-c1 complex s | UQCRC1 | DVVFNYLHATAFQGTPLAQAVTC | 1.4183 | | 1.3969 | |
| Cytochrome b-c1 complex s | UQCRC1 | MVLAAAGGVEHQQLLDLAQK | 1.5624 | | 1.6586 | |
| Transitional endoplasmi | VCP | DHFEEAMR | 0.20611 | 21.24 | 1.4096 | 26.47 |
| Transitional endoplasmi | VCP | ESIESEIR | 0.16428 | | NaN | |

SUPPLEMENTARY TABLE 2-continued

All identification and quantification information used to quantify proteins.

| Protein | Gene | Peptide | | | | |
|---|---|---|---|---|---|---|
| Transitional endoplasmi | VCP | GFGSFR | 0.22985 | | 1.287 | |
| Transitional endoplasmi | VCP | KYEMFAQTLQQSR | NaN | | 0.47634 | |
| Transitional endoplasmi | VCP | MTNGFSGADLTEICQR | 0.2695 | | 1.5438 | |
| Transitional endoplasmi | VCP | QTNPSAMEVEEDDPVPEIR | 0.15975 | | 1.292 | |
| Transitional endoplasmi | VCP | RDHFEEAMR | 0.17819 | | 1.459 | |
| Transitional endoplasmi | VCP | SVSDNDIR | 0.15796 | | 1.2779 | |
| Transitional endoplasmi | VCP | YEMFAQTLQQSR | 0.24338 | | 1.4679 | |
| Vimentin | VIM | DNLAEDIMR | 0.79552 | 16.24 | 1.6492 | 33.78 |
| Vimentin | VIM | EEAENTLQSFR | 0.81105 | | 1.4753 | |
| Vimentin | VIM | EKLQEEMLQR | 0.77968 | | NaN | |
| Vimentin | VIM | ILLAELEQIK | 0.71178 | | 1.3289 | |
| Vimentin | VIM | ILLAELEQLKGQGK | NaN | | 2.7399 | |
| Vimentin | VIM | LGDLYEEEMR | 0.45107 | | 0.90103 | |
| Vimentin | VIM | LQEEMLQR | 0.8627 | | 1.8464 | |
| Vimentin | VIM | QDVDNASIAR | 0.89058 | | 1.652 | |
| Vimentin | VIM | QVDQLTNDK | 0.72609 | | 1.3024 | |
| Vimentin | VIM | RQVDQLTNDK | 0.70013 | | 1.2391 | |
| Vimentin | VIM | VEVERDNLAEDIMR | 0.77955 | | 1.0746 | |
| Female-lethal(2)D homo | WTAP | EGNTTEDDFPSSPGNGNK | NaN | | NaN | |
| Female-lethal(2)D homo | WTAP | LTNGPSNGSSSR | NaN | | NaN | |
| Female-lethal(2)D homo | WTAP | QQLAQYQQQQSQASAPSTSR | NaN | | 0.67594 | |
| Female-lethal(2)D homo | WTAP | TSGSGFHR | NaN | | NaN | |

| µl PrESTs (1 + 2) | µl PrESTs (3) | Exactive pmol/µl 1 | Exactive pmol/µl 2 | Exactive pmol/µl 3 | pmol PrEST 1 |
|---|---|---|---|---|---|
| 0.021 | 0.0086 | 186.99624 | 129.566 | 51.550628 | 3.926921 |
| 0.021 | 0.0086 | 186.99624 | 129.566 | 51.550628 | 3.926921 |
| 0.021 | 0.0086 | 186.99624 | 129.566 | 51.550628 | 3.926921 |
| 0.021 | 0.0086 | 186.99624 | 129.566 | 51.550628 | 3.926921 |
| 0.006 | 0.0215 | 179.22945 | 128.578 | 56.812437 | 1.075377 |
| 0.006 | 0.0215 | 179.22945 | 128.578 | 56.812437 | 1.075377 |
| 0.006 | 0.0215 | 179.22945 | 128.578 | 56.812437 | 1.075377 |
| 0.099 | 0.0421 | 222.86724 | 206.449 | 84.899424 | 22.06386 |
| 0.099 | 0.0421 | 222.86724 | 206.449 | 84.899424 | 22.06386 |
| 0.099 | 0.0421 | 222.86724 | 206.449 | 84.899424 | 22.06386 |
| 0.099 | 0.0421 | 222.86724 | 206.449 | 84.899424 | 22.06386 |
| 0.099 | 0.0421 | 222.86724 | 206.449 | 84.899424 | 22.06386 |
| 0.099 | 0.0421 | 222.86724 | 206.449 | 84.899424 | 22.06386 |
| 0.099 | 0.0421 | 222.86724 | 206.449 | 84.899424 | 22.06386 |
| 0.099 | 0.0421 | 222.86724 | 206.449 | 84.899424 | 22.06386 |
| 0.297 | 0.4921 | 163.24925 | 124.502 | 55.082409 | 48.48503 |
| 0.297 | 0.4921 | 163.24925 | 124.502 | 55.082409 | 48.48503 |
| 0.297 | 0.4921 | 163.24925 | 124.502 | 55.082409 | 48.48503 |
| 0.297 | 0.4921 | 163.24925 | 124.502 | 55.082409 | 48.48503 |
| 0.297 | 0.4921 | 163.24925 | 124.502 | 55.082409 | 48.48503 |
| 0.297 | 0.4921 | 163.24925 | 124.502 | 55.082409 | 48.48503 |
| 0.297 | 0.4921 | 163.24925 | 124.502 | 55.082409 | 48.48503 |
| 0.297 | 0.4921 | 163.24925 | 124.502 | 55.082409 | 48.48503 |
| 0.297 | 0.4921 | 163.24925 | 124.502 | 55.082409 | 48.48503 |

SUPPLEMENTARY TABLE 2-continued

All identification and quantification information used to quantify proteins.

| | | | | | |
|---|---|---|---|---|---|
| 0.297 | 0.4921 | 163.24925 | 124.502 | 55.082409 | 48.48503 |
| 0.006 | 0.0028 | 178.53242 | 165.579 | 59.162252 | 1.071195 |
| 0.006 | 0.0028 | 178.53242 | 165.579 | 59.162252 | 1.071195 |
| 0.006 | 0.0028 | 178.53242 | 165.579 | 59.162252 | 1.071195 |
| 0.006 | 0.0028 | 178.53242 | 165.579 | 59.162252 | 1.071195 |

| pmol PrEST 2 | pmol PrEST 3 | pmol Protein 1 | pmol Protein 2 | pmol Protein 3 |
|---|---|---|---|---|
| 2.720886 | 0.443335 | 0.654225 | 0.433791 | 0.527613 |
| 2.720886 | 0.443335 | 0.686936 | 0.486277 | 0.592163 |
| 2.720886 | 0.443335 | 0.695772 | 0.510189 | 0.582011 |
| 2.720886 | 0.443335 | 0.661608 | 0.58197 | 0.767502 |
| 0.771468 | 1.221467 | 1.7277 | 1.212825 | 1.596214 |
| 0.771468 | 1.221467 | 1.638874 | 1.094173 | 1.706268 |
| 0.771468 | 1.221467 | 1.835668 | 1.205342 | 2.025926 |
| 20.43845 | 3.574266 | 4.606713 | 4.212569 | 5.038285 |
| 20.43845 | 3.574266 | 1.659445 | 3.357629 | #VALUE! |
| 20.43845 | 3.574266 | 4.79602 | 4.697778 | 4.60008 |
| 20.43845 | 3.574266 | 2.796814 | #VALUE! | 1.702566 |
| 20.43845 | 3.574266 | 5.183241 | 5.508163 | 5.517951 |
| 20.43845 | 3.574266 | 3.17521 | 3.265043 | 4.617951 |
| 20.43845 | 3.574266 | 4.528386 | 3.641928 | 5.214854 |
| 20.43845 | 3.574266 | 4.224787 | 3.228458 | 4.567554 |
| 20.43845 | 3.574266 | 4.566777 | 4.97431 | 5.246665 |
| 36.97709 | 27.10605 | 39.41833 | 29.41602 | 44.7033 |
| 36.97709 | 27.10605 | 37.8799 | 29.99027 | 39.98956 |
| 36.97709 | 27.10605 | #VALUE! | 28.8303 | #VALUE! |
| 36.97709 | 27.10605 | 34.9771 | 26.31956 | 36.02123 |
| 36.97709 | 27.10605 | 35.38922 | #VALUE! | 74.26788 |
| 36.97709 | 27.10605 | 25.26797 | 16.67926 | 24.42337 |
| 36.97709 | 27.10605 | 42.62416 | 31.90014 | 50.04862 |
| 36.97709 | 27.10605 | 39.76887 | 32.93106 | 44.7792 |
| 36.97709 | 27.10605 | 38.35263 | 26.8487 | 35.30292 |
| 36.97709 | 27.10605 | 41.11821 | 25.88877 | 33.58711 |
| 36.97709 | 27.10605 | 28.37586 | 28.82549 | 29.12817 |
| 0.993474 | 0.165654 | #VALUE! | #VALUE! | #VALUE! |
| 0.993474 | 0.165654 | #VALUE! | #VALUE! | #VALUE! |
| 0.993474 | 0.165654 | 0.054909 | #VALUE! | 0.111972 |
| 0.993474 | 0.165654 | #VALUE! | #VALUE! | #VALUE! |

Median CVs 12.33
Average CVs 18.39

To independently assess the precision of this step of absolute protein quantification, we compared the ratios determined from 'limit tryptic peptides' (those without internal arg or lys) to those determined from the longer versions of the peptide containing one or two missed tryptic cleavage sites. These peptides are very problematic for peptide standard based methods such as AQUA, but in our measurements very similar ratios were measured for such peptides. This shows that digestion proceeded identical for PrEST and endogenous protein (Table 1). Thus, far from introducing uncertainty, in the SILAC-PrEST approach these peptides can provide additional quantification information.

TABLE 1

Comparison of limit tryptic peptides and peptides with missed tryptic cleavage sites. Peptides with one or two miss cleavages as well as their ratios are depicted. The ratios of the two versions vary on average by 19%, which is in the normal range of variation of peptides derived from one protein.

| Gene Names | Sequence | SEQ ID NO. | Missed Cleavages | Ratio H/L Mastermix1 | CV (%) | Ratio H/L Mastermix2 | CV (%) | Ratio H/L Mastermix3 | CV (%) |
|---|---|---|---|---|---|---|---|---|---|
| HSPA4 | ELAILLGMLDPAEK | 189 | 0 | 0.707 | 16.2 | 0.803 | 6.7 | 1.072 | 19.7 |
| HSPA4 | ELAILLGMLDPAEKDEK | 190 | 1 | 0.562 | | 0.730 | | 1.418 | |
| HSPA4 | EDQYDHLDAADMTK | 140 | 0 | 0.220 | 9.2 | 0.132 | 25.8 | 0.558 | 35.6 |
| HSPA4 | NKEDQYDHLDAADMTK | 142 | 1 | 0.193 | | 0.191 | | 0.933 | |
| ATP53 | VLDSGAPIK | 56 | 0 | 0.738 | 11.8 | 0.452 | 46.9 | 1.009 | 6.5 |
| ATP5B | VLDSGAPIKIPVGPETLGR | 57 | 1 | 0.872 | | 0.901 | | 1.107 | |
| PPIB | DKPLKDVIIADCGK | 181 | 2 | 0.526 | 6.9 | 0.436 | 14.6 | 0.889 | 23.2 |

TABLE 1-continued

Comparison of limit tryptic peptides and peptides with missed tryptic cleavage sites. Peptides with one or two miss cleavages as well as their ratios are depicted. The ratios of the two versions vary on average by 19%, which is in the normal range of variation of peptides derived from one protein.

| Gene Names | Sequence | SEQ ID NO. | Missed Cleavages | Ratio H/L Mastermix1 | CV (%) | Ratio H/L Mastermix2 | CV (%) | Ratio H/L Mastermix3 | CV (%) |
|---|---|---|---|---|---|---|---|---|---|
| PPIB | DVIIADCGK | 183 | 0 | 0.580 | | 0.354 | | 1.237 | |
| FASN | QQEQQVPILEK | 124 | 0 | | | 0.627 | 18.6 | 1.040 | 13.9 |
| FASN | RQQEQQVPILEK | 125 | 1 | | | 0.481 | | 0.853 | |
| FEN1 | LDPNKYPVPENWLHK | 131 | 1 | 0.680 | 8.1 | 0.632 | 0.3 | 1.279 | 14.4 |
| FEN1 | YPVPENWLHK | 135 | 0 | 0.607 | | 0.629 | | 1.043 | |
| SFN | EKVETELQGVCDTVLGLLDSHLIK | 248 | 1 | 0.442 | 6.3 | 0.389 | 6.4 | 1.188 | 1.2 |
| SFN | VETELQGVCDTVLGLLDSHLIK | 205 | 0 | 0.483 | | 0.426 | | 1.168 | |
| SFN | SNEEGSEEK | 249 | 0 | 0.286 | 11.0 | | | | |
| SFN | SNEEGSEEKGPEVR | 204 | 1 | 0.334 | | | | | |
| SEN | YLAEVATGDDK | 207 | 0 | 0.371 | 1.3 | 0.395 | 19.7 | 1.012 | 8.5 |
| SFN | YLAEVATGDDKK | 208 | 1 | 0.364 | | 0.299 | | 1.142 | |
| TPR | LESALTELEQLR | 218 | 0 | 0.139 | 17.4 | 0.121 | 13.0 | 1.243 | 10.9 |
| TPR | LESALTELEQLRK | 219 | 1 | 0.177 | | 0.145 | | 1.064 | |
| VCP | DHFEEAMR | 224 | 0 | 0.187 | 11.1 | 0.134 | 35.7 | 1.712 | 59.7 |
| VCP | RDHFEEAMR | 230 | 1 | 0.218 | | 0.224 | | 0.696 | |
| VCP | YEMFAQTLQQSR | 232 | 0 | 0.169 | 4.4 | 0.146 | 6.6 | 1.584 | 37.1 |
| VCP | KYEMFAQTLQQSR | 227 | 1 | 0.159 | | 0.133 | | 0.926 | |
| VIM | QVDQLTNDK | 241 | 0 | 0.620 | 8.5 | 0.813 | 2.3 | | |
| VIM | RQVDQLTNDK | 242 | 1 | 0.699 | | 0.788 | | | |
| VIM | LQEEMLQR | 239 | 0 | 0.868 | 3.9 | 0.834 | 65.0 | | |
| VIM | EKLQEEMLQR | 235 | 1 | 0.821 | | 0.309 | | | |

Figure 4:
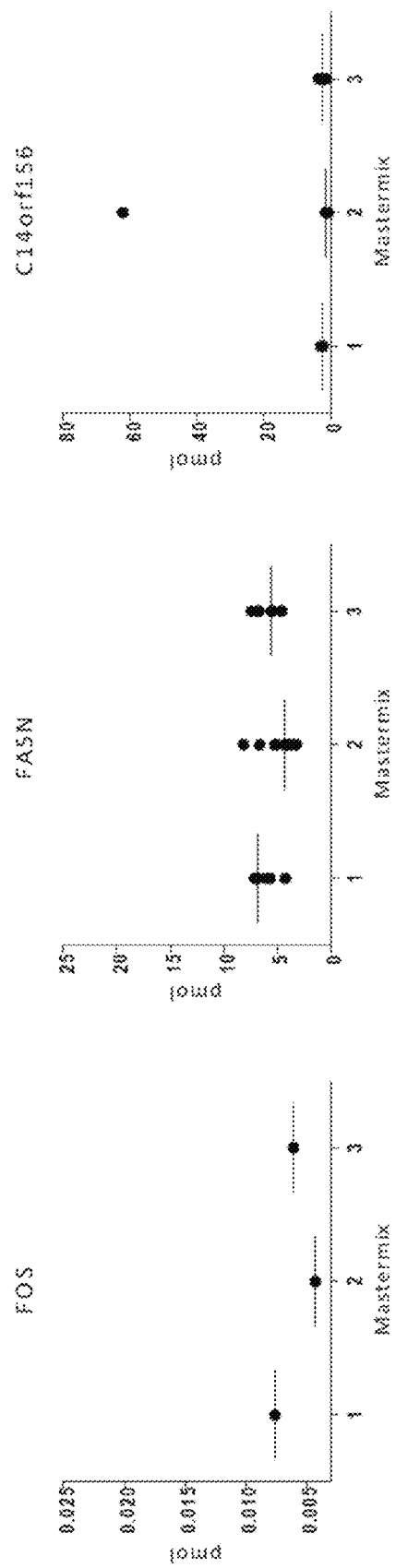
FIG. 4: Reproducibility of the absolute quantification procedure. Three independent quantification experiments for representative examples, in which the master mix preparation as well as the PrEST quantification were performed independently. The bars reflect the median of the peptide ratios for each protein.
Figure 5:
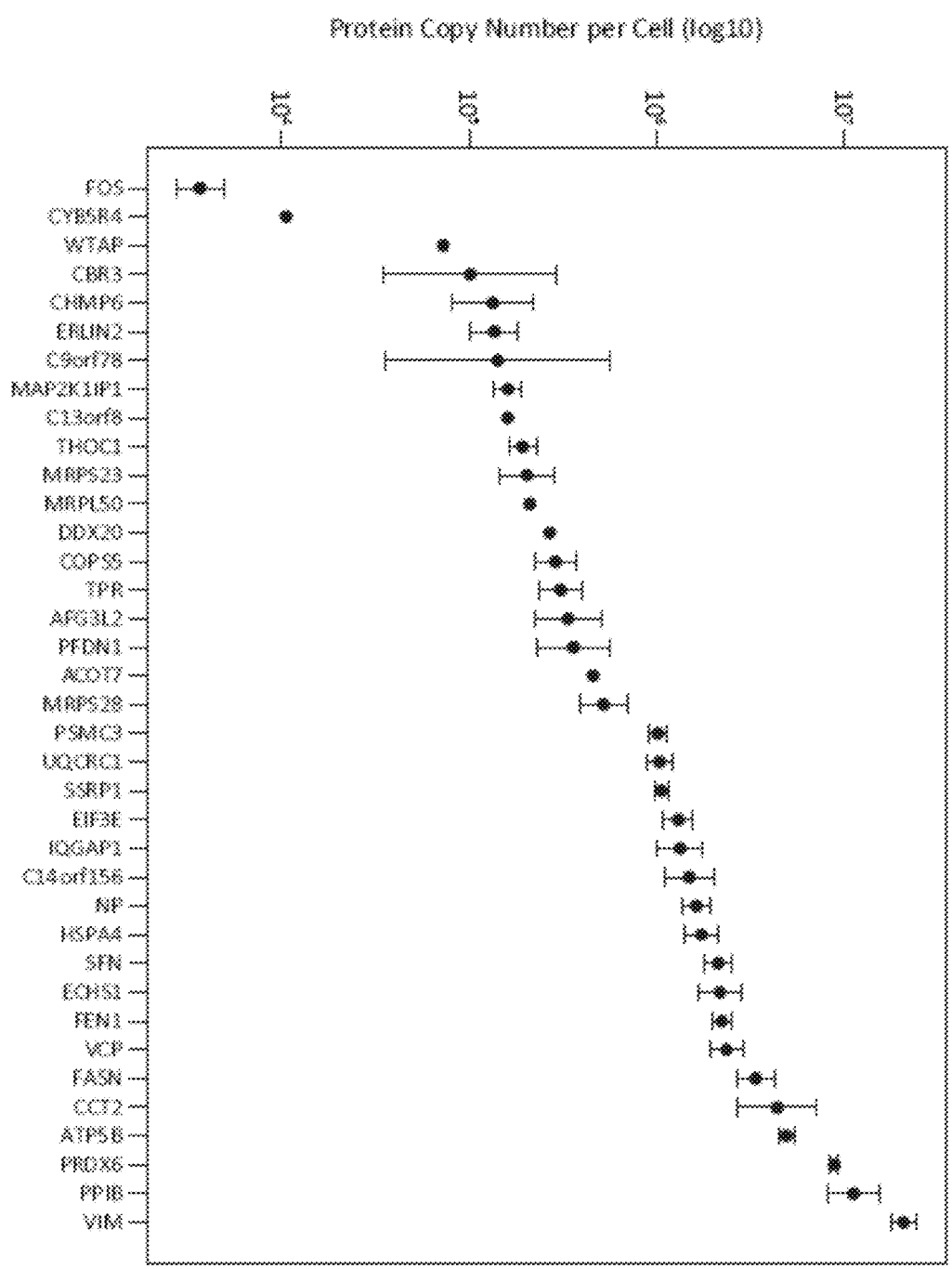
FIG. 5: Protein copy numbers determined per HeLa cell. The dot plot shows the protein copy numbers per cell measured in three independent experiments. The error bars correspond to the CVs. Proteins with copy numbers ranging from 4 000 to 20 000 000 per cell were quantified (see also Table 2).

To assess the degree of variability associated with both steps of the absolute quantification procedure, we repeated the entire workflow two more times, including PrEST quantification and master mix generation as well as measurement of cellular abundance of the target proteins. This analysis showed that the standard errors of the mean associated with all steps together are on average 24%. This value is excellent and to our knowledge the most accurate determination of cellular expression levels reported so far. Even more importantly, the errors of each of the step in the workflow for each of the proteins are immediately apparent from the individual CVs. Thus all protein expression level measurements can be classified and accepted or discarded according to the confidence of measurements. FIG. 4 displays typical examples of protein expression determination from the triplicate measurements. Comparing the peptide ratio spreads to the variability of the mean protein values revealed that the preparation of the master mix contributed the largest variability whereas errors due to SILAC ratio determination were somewhat lower. Automated preparation of the master mix could therefore lead to further improvements in the future.

Protein copy number determination in HeLa cells—Next we used the absolute values for protein amounts in our HeLa cell lysate to calculate the corresponding copy numbers in cells. HeLa cells numbers were determined automatically in a cell counter (see Experimental Procedures). Given the known amount of each PrEST and their SILAC ratios with respect to the endogenous proteins we determined the cellular copy numbers of 37 different proteins. Very high accuracy of absolute quantification to within a standard error of 25% was achieved for 30 of 37 proteins (Table 2).

TABLE 2

Protein Copy Numbers per HeLa cell

| Protein Names | Gene Names | Median | SEM (%)* | Master mix 1 | Master mix 2 | Master mix 3 |
|---|---|---|---|---|---|---|
| 14-3-3 protein sigma | SFN | 2,104,742 | 9.57 | 2,128,717 | 1,562,390 | 2,104,742 |
| 26S protease regulatory subunit 6A | PSMC3 | 1,009,040 | 6.71 | 1,009,040 | 985,010 | 1,211,206 |
| 28S ribosomal protein S23, mitochondrial | MRPS23 | 202,529 | 19.64 | 202,529 | 161,109 | 308,977 |
| 28S ribosomal protein S35, mitochondrial | MRPS28 | 516,278 | 15.46 | 586,618 | 337,285 | 516,278 |
| 39S ribosomal protein L50, mitochondrial | MRPL50 | 212,893 | 20.00 | 170,320 | 255,465 | |
| AFG3-like protein 2 | AFG3L2 | 335,545 | 20.37 | 335,545 | 363,149 | 173,343 |
| ATP synthase subunit beta, mitochondrial | ATP5B | 4,870,803 | 5.63 | 5,431,604 | 4,870,803 | 4,476,459 |
| Carbonyl reductase [NADPH] 3 | CBR3 | 101,019 | 63.47 | 101,019 | 60,715 | 498,397 |
| Charged multivesicular body protein 6 | CHMP6 | 133,137 | 24.10 | 154,916 | 61,839 | 133,137 |
| COP9 signalosome complex subunit 5 | COPS5 | 287,189 | 13.59 | 287,189 | 211,517 | 343,078 |
| Cytochrome b5 reductase 4 | CYB5R4 | 10,537 | —** | 10,537 | — | — |
| Cytochrome b-c1 complex subunit 1, mitochondrial | UQCRC1 | 1,032,315 | 8.96 | 1,032,315 | 808,601 | 1,099,145 |
| Cytosolic acyl coenzyme A thioester hydrolase | ACOT7 | 455,871 | 0.46 | 457,985 | 453,757 | |
| Endoplasmic reticulum lipid raft-associated protein 2 | ERLIN2 | 135,785 | 18.00 | 218,008 | 127,563 | 135,785 |
| Enoyl-CoA hydratase, mitochondrial | ECHS1 | 2,162,058 | 15.20 | 2,705,599 | 1,574,948 | 2,162,058 |
| Eukaryotic translation initiation factor 3 subunit 6 | EIF3E | 1,298,361 | 9.85 | 1,009,294 | 1,298,361 | 1,422,955 |
| FACT complex subunit SSRP1 | SSRP1 | 1,054,400 | 4.43 | 1,086,956 | 937,213 | 1,054,400 |
| Fatty acid synthase | FASN | 3,361,337 | 13.11 | 4,093,238 | 2,575,577 | 3,361,337 |
| Flap endonuclease 1 | FEN1 | 2,215,232 | 6.87 | 2,215,232 | 2,220,140 | 1,789,805 |
| Heat shock 70 kDa protein 4 | HSPA4 | 1,719,164 | 11.22 | 1,855,515 | 1,258,240 | 1,719,164 |
| Hepatocellular carcinoma-associated antigen 59 | C9orf78 | 140,949 | 79.08 | 1,577,757 | 140,949 | 114,844 |
| Mitogen-activated protein kinase scaffold protein 1 | MAP2K1IP1 | 160,325 | 10.12 | 160,325 | 205,536 | 148,606 |
| Nucleoprotein TPR | TPR | 306,362 | 14.08 | 343,837 | 208,601 | 306,362 |
| Peptidyl-prolyl cis-trans isomerase B | PPIB | 11,155,435 | 17.40 | 14,871,040 | 8,035,119 | 11,155,435 |
| Peroxiredoxin 6 | PRDX6 | 8,815,042 | 3.13 | 9,010,737 | 8,118,496 | 8,815,042 |
| Prefoldin subunit 1 | PFDN1 | 358,511 | 22.03 | 383,937 | 358,511 | 171,199 |
| Pre-mRNA-splicing regulator WTAP | WTAP | 72,199 | — | 72,199 | — | — |
| Probable ATP-dependent RNA helicase DDX20 | DDX20 | 268,121 | — | 268,121 | — | — |
| Proto-oncogene c-Fos | FOS | 3,651 | 15.95 | 4,559 | 2,575 | 3,651 |
| Purine nucleoside phosphorylase | NP | 1,618,680 | 10.11 | 1,832,987 | 1,284,556 | 1,618,680 |
| Ras GTPase-activating-like protein IQGAP1 | IQGAP1 | 1,322,762 | 15.42 | 1,667,348 | 963,468 | 1,322,762 |
| SRA stem-loop-interacting RNA-binding protein, mitochondrial | C14orf156 | 1,482,399 | 15.25 | 1,557,983 | 919,914 | 1,482,399 |
| T-complex protein 1 subunit beta | CCT2 | 4,352,706 | 29.38 | 8,283,044 | 3,162,779 | 4,352,706 |
| THO complex subunit 1 | THOC1 | 191,319 | 9.53 | 211,743 | 151,702 | 191,319 |
| Transitional endoplasmic reticulum ATPase | VCP | 2,343,243 | 10.89 | 2,343,243 | 1,716,701 | 2,493,783 |
| Vimentin | VIM | 20,600,599 | 8.73 | 20,600,599 | 17,557,991 | 23,805,318 |
| Zinc finger protein 828 | C13orf8 | 167,150 | 29.45 | 117,929 | 216,371 | — |

*Standard error of the mean (SEM) for the three replicates in percent.
**no valid data obtained Cellular copy numbers are only known for very few proteins and it is therefore interesting to relate these copy numbers to the known functions of the proteins (Suppl. Table 3). The cytoskeletal protein vimentin forms intermediate filaments and was the most abundant protein with 20 million copies per cell. At the other extreme, the transcription factor and oncogene FOS is present in about 4,000 copies in our HeLa cell sample. As expected, proteins involved in cell signaling are generally expressed at lower values—as an example even the scaffolding factor mitogen-activated protein kinase scaffold protein 1 (MAP2K1IP1) is present at only 160,000 copies. However, ubiquitous signaling factors with a general chaperone-like role—such as 14-3-3 isoforms—are very highly expressed (14-3-3 sigma; 2.1 million copies). Two members of the mitochondrial ribosome have about 200,000 copies in this cell line (L23 and L5), whereas a third (L35) has about 500,000 (Note that not all ribosomal protein subunits have equal stoichiometry). The mitochondrial genome only encodes 13 genes therefore it is perhaps surprising that proteins involved in their translation are needed in such high copy numbers. A member of the respiratory chain, ATP5B, has about 5 million copies per HeLa cells—about five fold higher than PSMC3, a regulatory component of the proteasome. The T-complex is a member of a chaperone system and as expected it has a very high copy number (about 4 million). Fatty acid synthase, a classical enzyme, is expressed at 3.4 million copies, whereas another enzyme acyl coenzyme A thioester hydrolase (ACOT7) is expressed about seven-fold lower (450,000 copies). Such expression numbers could be interesting for modeling metabolic pathways. These are anecdotal examples but they illustrate that knowledge of the absolute expression levels of cellular proteins can contribute to the understanding of their roles in the cell.

SUPPLEMENTARY TABLE 3 corresponding UniProt link for the 43 proteins used for protein copy number determination.

| Protein Names | Gene Names | Function |
|---|---|---|
| 14-3-3 protein sigma | SFN | http://www.uniprot.org/uniprot/P31947 |
| 26S protease regulatory subunit 6A | PSMC3 | http://www.uniprot.org/uniprot/P17980 |
| 28S ribosomal protein S23, mitochondrial | MRPS23 | http://www.uniprot.org/uniprot/Q9Y3D9 |
| 28S ribosomal protein S35, mitochondrial | MRPS28 | http://www.uniprot.org/uniprot/Q9Y2Q9 |
| 39S ribosomal protein L50, mitochondrial | MRPL50 | http://www.uniprot.org/uniprot/Q8N5N7 |
| AFG3-like protein | AFG3L2 | http://www.uniprot.org/uniprot/Q9Y4W6 |

SUPPLEMENTARY TABLE 3-continued corresponding UniProt link for the 43 proteins used for protein copy number determination.

| Protein Names | Gene Names | Function |
|---|---|---|
| ATP synthase subunit beta, mitochondrial | ATP5B | http://www.uniprot.org/uniprot/P06576 |
| Carbonyl reductase [NADPH] 3 | CBR3 | http://www.uniprot.org/uniprot/O75828 |
| Charged multivesicular body protein 6 | CHMP6 | http://www.uniprot.org/uniprot/Q96FZ7 |
| COP9 signalosome complex subunit 5 | COPS5 | http://www.uniprot.org/uniprot/Q92905 |
| Cytochrome b5 reductase 4 | CYB5R4 | http://www.uniprot.org/uniprot/Q7L1T6 |
| Cytochrome b-c1 complex subunit 1, mitochondrial | UQCRC1 | http://www.uniprot.org/uniprot/P31930 |
| Cytosolic acyl coenzyme A thioester hydrolase | ACOT7 | http://www.uniprot.org/uniprot/O00154 |
| Endoplasmic reticulum lipid raft-associated protein 2 | ERLIN2 | http://www.uniprot.org/uniprot/O94905 |
| Enoyl-CoA hydratase, mitochondrial | ECHS1 | http://www.uniprot.org/uniprot/P30084 |
| Eukaryotic translation initiation factor 3 subunit 6 | EIF3E | http://www.uniprot.org/uniprot/P60228 |
| FACT complex subunit SSRP1 | SSRP1 | http://www.uniprot.org/uniprot/Q08945 |
| Fatty acid synthase | FASN | http://www.uniprot.org/uniprot/Q6PJJ3 |
| Flap endonuclease 1 | FEN1 | http://www.uniprot.org/uniprot/P39748 |
| Heat shock 70 kDa protein 4 | HSPA4 | http://www.uniprot.org/uniprot/P34932 |
| Hepatocellular carcinoma-associated antigen 59 | C9orf78 | http://www.uniprot.org/uniprot/Q9NZ63 |
| Mitogen-activated protein kinase scaffold protein 1 | MAP2K1IP1 | http://www.uniprot.org/uniprot/Q9UHA4 |
| Nucleoprotein TPR | TPR | http://www.uniprot.org/uniprot/P12270 |
| Peptidyl-prolyl cis-trans isomerase B | PPIB | http://www.uniprot.org/uniprot/P23284 |
| Peroxiredoxin 6 | PRDX6 | http://www.uniprot.org/uniprot/P30041 |
| Prefoldin subunit 1 | PFDN1 | http://www.uniprot.org/uniprot/O60925 |
| Pre-mRNA-splicing regulator WTAP | WTAP | http://www.uniprot.org/uniprot/Q15007 |
| Probable ATP-dependent RNA helicase DDX20 | DDX20 | http://www.uniprot.org/uniprot/Q9UHI6 |
| Proto-oncogene c-Fos | FOS | http://www.uniprot.org/uniprot/P01100 |
| Purine nucleoside phosphorylase | NP | http://www.uniprot.org/uniprot/P00491 |
| Ras GTPase-activating-like protein IQGAP1 | IQGAP1 | http://www.uniprot.org/uniprot/P46940 |
| SRA stem-loop-interacting RNA-binding protein, mitochondrial | C14orf156 | http://www.uniprot.org/uniprot/Q9GZT3 |
| T-complex protein 1 subunit beta | CCT2 | http://www.uniprot.org/uniprot/P78371 |
| THO complex subunit 1 | THOC1 | http://www.uniprot.org/uniprot/Q96FV9 |
| Transitional endoplasmic reticulum ATPase | VCP | http://www.uniprot.org/uniprot/P55072 |
| Vimentin | VIM | http://www.uniprot.org/uniprot/P08670 |
| Zinc finger protein 828 | C13orf8 | http://www.uniprot.org/uniprot/Q96JM3 |

Figure 7:
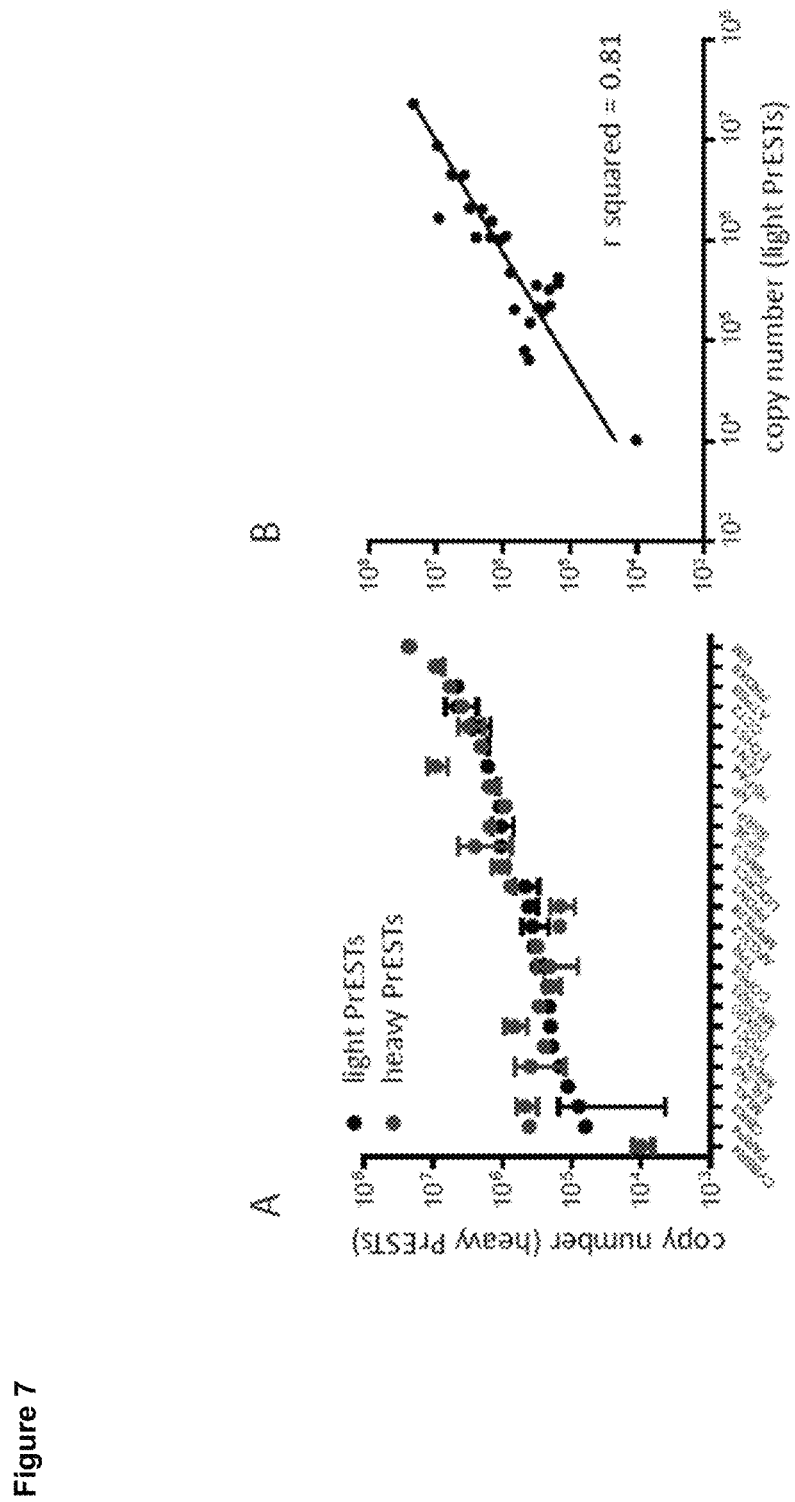
FIG. 7: Absolute Quantification using heavy PrESTs. (A) Comparison of copy numbers obtained by quantifying light PrESTs against SILAC labeled heavy cell lysate (black symbols) versus quantifying heavy PrESTs against unlabeled cell lysate (red symbols). (B) Values shown in A but plotted as a scatter graph.

Absolute Quantification using heavy PrESTs—Above we used already expressed and purified PrESTs and quantified against heavy ABP protein and heavy SILAC-labeled cell lysate. While convenient to determine copy numbers in cell lines, in other applications it would be more appropriate to express heavy labeled PrESTs, which can then be mixed into any proteome of choice—including tissue and clinical body fluid samples. To apply our absolute quantification approach to non-labeled samples we expressed 28 of the PrESTs in heavy SILAC labeled E. coli, purified them and prepared a heavy master mix. To streamline quantification of PrEST levels, we developed an automated set up employing static nanoelectrospray (Advion NanoMate; see Example 1). As expected, spiking the heavy master mix into normal, non-SILAC labeled cells allowed equally straightforward quantification of the targeted proteins, with good correlation to the previous experiment (FIG. 7). Detailed information about the identification and quantification of the proteins is provided in Supplementary Table 4.

SUPPL. TABLE 4

All identification and quantification information of the experiment in which heavy PrESTs were spiked into unlabeled HeLa lysate

| Protein Names | Gene Name | Sequence | SEQ ID NO. | Ratio H/L Mastermix1 | Ratio H/L Mastermix2 | Ratio H/L Mastermix3 | Protein Conc. µg/µl | µl PrESTs (1 + 2) |
|---|---|---|---|---|---|---|---|---|
| AFG3-like protein 2 | AFG3L2 | EQYLYTK | 47 | NaN | NaN | NaN | 0.779 | 0.01284 |
| AFG3-like protein 2 | AFG3L2 | HFEQAIER | 250 | NaN | NaN | 1.0384 | 0.779 | 0.01284 |
| AFG3-like protein 2 | AFG3L2 | HLSDSINQK | 48 | 0.98061 | 1.034 | NaN | 0.779 | 0.01284 |
| AFG3-like protein 2 | AFG3L2 | LASLTPGFSGADVANVCNEAALIAAR | 251 | 0.64771 | 0.68664 | 0.73842 | 0.779 | 0.01284 |

SUPPL. TABLE 4-continued

All identification and quantification information of the experiment in which heavy PrESTs were spiked into unlabeled HeLa lysate

| Protein | Gene | Peptide | # | Val1 | Val2 | Val3 | Val4 | Val5 |
|---|---|---|---|---|---|---|---|---|
| AFG3-like protein 2 | AFG3L2 | TVAYHEAGHAVAGWYLEHADPLLK | 252 | 0.99036 | 0.88405 | 1.0667 | 0.779 | 0.01284 |
| AFG3-like protein 2 | AFG3L2 | VSEEIFFGR | 50 | 0.88034 | 1.0026 | 0.087458 | 0.779 | 0.01284 |
| ATP synthase subunit beta, | ATP5B | IMNVIGEPIDER | 52 | 0.49547 | 0.38751 | 0.46817 | 0.359 | 0.25036 |
| ATP synthase subunit beta, | ATP5B | IPVGPELTGR | 53 | 0.67213 | 0.52947 | 0.5949 | 0.359 | 0.25036 |
| ATP synthase subunit beta, | ATP5B | LVLEVAQHLGESTVR | 54 | 0.57216 | 0.53836 | 0.64057 | 0.359 | 0.25036 |
| ATP synthase subunit beta, | ATP5B | TIAMDGTEGLVR | 55 | 0.52173 | 0.3056 | 0.41416 | 0.359 | 0.25036 |
| ATP synthase subunit beta, | ATP5B | VLDSGAPIK | 56 | 0.69347 | 0.569 | 0.60973 | 0.359 | 0.25036 |
| ATP synthase subunit beta, | ATP5B | VLDSGAPIKIPVGPETLGR | 57 | 0.71587 | 0.67498 | NaN | 0.359 | 0.25036 |
| Carbonyl reductase [NADPH | CBR3 | AFENCSEDLQER | 75 | 3.7066 | 3.6554 | 2.7849 | 0.692 | 0.01445 |
| Carbonyl reductase [NADPH | CBR3 | FHSETLTEGDLVDLMK | 76 | 0.82772 | 0.54401 | 0.65383 | 0.692 | 0.01445 |
| Carbonyl reductase [NADPH | CBR3 | VVNISSLQCLR | 78 | NaN | 0.61063 | 0.027081 | 0.692 | 0.01445 |
| T-complex protein 1 subuni | CCT2 | HGINCFINR | 80 | 0.96794 | 0.9253 | 0.80254 | 0.392 | 0.38219 |
| T-complex protein 1 subuni | CCT2 | ILIANTGMDTDK | 81 | 0.86038 | 0.52336 | 0.58541 | 0.392 | 0.38219 |
| T-complex protein 1 subuni | CCT2 | LALVTGGEIASTFDHPELVK | 83 | 1.0899 | 0.99631 | 1.1095 | 0.392 | 0.38219 |
| T-complex protein 1 subuni | CCT2 | LIEEVMIGEDK | 84 | 0.83525 | 0.94634 | 0.78472 | 0.392 | 0.38219 |
| T-complex protein 1 subuni | CCT2 | VAEIEHAEK | 85 | 1.1668 | 0.99657 | 1.1107 | 0.392 | 0.38219 |
| T-complex protein 1 subuni | CCT2 | VAEIEHAEKEK | 86 | 0.84991 | 0.99839 | NaN | 0.392 | 0.38219 |
| COP9 signalosome complex | COPS5 | DHHYFK | 89 | 0.72801 | 0.3227 | 0.37943 | 0.999 | 0.01001 |
| COP9 signalosome complex | COPS5 | ISALALLK | 90 | NaN | NaN | 0.23709 | 0.999 | 0.01001 |
| Cytochrome b5 reductase 4 | CYB5R4 | QGHISPALLSEFLK | 94 | NaN | 12.575 | 13.552 | 0.867 | 0.01153 |
| Cytochrome b5 reductase 4 | CYB5R4 | TEDDIIWR | 95 | 11.628 | 12.424 | 12.299 | 0.867 | 0.01153 |
| Probable ATP-dependent RI | DDX20 | VLISTDLTSR | 97 | 0.59562 | NaN | NaN | 0.705 | 0.01419 |
| Enoyl-CoA hydratase, mitoc | ECHS1 | EGMTAFVEK | 98 | 1.0475 | NaN | 0.02831 | 0.342 | 0.58542 |
| Enoyl-CoA hydratase, mitoc | ECHS1 | ESVNAAFEMTLTEGSK | 99 | 1.0239 | NaN | 0.98226 | 0.342 | 0.58542 |
| Enoyl-CoA hydratase, mitoc | ECHS1 | ICPVETLVEEAIQCAEK | 100 | 0.77883 | 0.73163 | 0.73992 | 0.342 | 0.58542 |

| μl PrESTs (3) | NanoMate pmol/μl | NanoMate pmol/μl | NanoMate pmol/μl | pmol PrEST 1 | pmol PrEST 2 | pmol PrEST 3 | pmol Protein 1 | pmol Protein 2 | pmol Protein 3 |
|---|---|---|---|---|---|---|---|---|---|
| 0.01284 | 18.253386 | 22.899283 | | 0.2343735 | 0.294027 | 0 | | | 0 |
| 0.01284 | 18.253386 | 22.899283 | | 0.2343735 | 0.294027 | 0 | | | |
| 0.01284 | 18.253386 | 22.899283 | | 0.2343735 | 0.294027 | 0 | 0.239008 | 0.284359 | |
| 0.01284 | 18.253386 | 22.899283 | | 0.2343735 | 0.294027 | 0 | 0.361849 | 0.428211 | 0 |
| 0.01284 | 18.253386 | 22.899283 | | 0.2343735 | 0.294027 | 0 | 0.236655 | 0.332591 | 0 |
| 0.01284 | 18.253386 | 22.899283 | | 0.2343735 | 0.294027 | 0 | 0.266231 | 0.293264 | 0 |
| 0.25036 | 23.934268 | 23.197529 | 19.970078 | 5.9921835 | 5.807733 | 4.999709 | 12.09394 | 14.98731 | 10.67926 |
| 0.25036 | 23.934268 | 23.197529 | 19.970078 | 5.9921835 | 5.807733 | 4.999709 | 8.915215 | 10.96896 | 8.404284 |
| 0.25036 | 23.934268 | 23.197529 | 19.970078 | 5.9921835 | 5.807733 | 4.999709 | 10.47292 | 10.78782 | 7.805093 |
| 0.25036 | 23.934268 | 23.197529 | 19.970078 | 5.9921835 | 5.807733 | 4.999709 | 11.48522 | 19.00436 | 12.07193 |
| 0.25036 | 23.934268 | 23.197529 | 19.970078 | 5.9921835 | 5.807733 | 4.999709 | 8.640869 | 10.20691 | 8.199873 |
| 0.25036 | 23.934268 | 23.197529 | 19.970078 | 5.9921835 | 5.807733 | 4.999709 | 8.370491 | 8.604304 | |
| 0.01445 | 71.889794 | 33.419567 | 44.296682 | 1.0388075 | 0.482913 | 0.640087 | 0.280259 | 0.132109 | 0.229842 |
| 0.01445 | 71.889794 | 33.419567 | 44.296682 | 1.0388075 | 0.482913 | 0.640087 | 1.255023 | 0.887691 | 0.978981 |
| 0.01445 | 71.889794 | 33.419567 | 44.296682 | 1.0388075 | 0.482913 | 0.640087 | | 0.790843 | 23.63602 |
| 0.38219 | | 17.42877 | 12.336037 | 0 | 6.661102 | 4.71471 | 0 | 7.198856 | 5.874735 |

SUPPL. TABLE 4-continued

All identification and quantification information of the experiment in which heavy PrESTs were spiked into unlabeled HeLa lysate

| | | | | | | | | | |
|---|---|---|---|---|---|---|---|---|---|
| 0.38219 | | 17.42877 | 12.336037 | 0 | 6.672907 | 4.71471 | 0 | 12.75013 | 8.053689 |
| 0.38219 | | 17.42877 | 12.336037 | 0 | 6.672907 | 4.71471 | 0 | 6.697622 | 4.2494 |
| 0.38219 | | 17.42877 | 12.336037 | 0 | 6.672907 | 4.71471 | 0 | 7.051279 | 6.008143 |
| 0.38219 | | 17.42877 | 12.336037 | 0 | 6.672907 | 4.71471 | 0 | 6.695874 | 4.244809 |
| 0.38219 | | 17.42877 | 12.336037 | 0 | 6.672907 | 4.71471 | 0 | 6.683668 | |
| 0.01001 | 14.240375 | 16.354906 | | 0.1425462 | 0.163713 | 0 | 0.195802 | 0.507321 | 0 |
| 0.01001 | 14.240375 | 16.354906 | | 0.1425462 | 0.163713 | 0 | | | 0 |
| 0.01153 | 21.356568 | 20.719244 | | 0.2462412 | 0.238893 | 0 | | 0.018997 | 0 |
| 0.01153 | 21.356568 | 20.719244 | | 0.2462412 | 0.238893 | 0 | 0.021177 | 0.019228 | 0 |
| 0.01419 | 20.843513 | 13.238853 | 14.941964 | 0.295695 | 0.187859 | 0.212026 | 0.496574 | | |
| 0.58542 | 7.2168512 | 13.696164 | 7.5470525 | 4.224889 | 8.018008 | 4.418195 | 4.033307 | | 156.5016 |
| 0.58542 | 7.2168512 | 13.696164 | 7.5470525 | 4.224889 | 8.018008 | 4.418195 | 4.126271 | | 4.49799 |
| 0.58542 | 7.2168512 | 13.696164 | 7.5470525 | 4.224889 | 8.018008 | 4.418195 | 5.424661 | 10.9591 | 5.97118 |

| Protein Names | Gene Name | Sequence | SEQ ID NO. | Ratio H/L Mastermix1 | Ratio H/L Mastermix2 | Ratio H/L Mastermix3 | Protein Conc. µg/µl | µl PrESTs (1 + 2) |
|---|---|---|---|---|---|---|---|---|
| Enoyl-CoA hydratase, mitoc | ECHS1 | IVVAMAK | 102 | NaN | NaN | 1.063 | 0.342 | 0.58542 |
| Enoyl-CoA hydratase, mitoc | ECHS1 | LFYSTFATDDR | 253 | 1.5764 | 1.5022 | 1.6594 | 0.342 | 0.58542 |
| Enoyl-CoA hydratase, mitoc | ECHS1 | LFYSTFATDDRK | 105 | NaN | 1.391 | NaN | 0.342 | 0.58542 |
| Enoyl-CoA hydratase, mitoc | ECHS1 | SLAMEMVLTGDR | 107 | 0.5035 | 0.63232 | 0.092059 | 0.342 | 0.58542 |
| Eukaryotic translation initia | EIF3E | LGHVVMGNNAVSPYQQVIEK | 108 | 0.11968 | 0.12455 | 0.048128 | 0.714 | 0.01401 |
| Eukaryotic translation initia | EIF3E | LNMTPEEAER | 109 | NaN | 0.088999 | NaN | 0.714 | 0.01401 |
| Eukaryotic translation initia | EIF3E | SQMLAMNIEK | 110 | 0.096546 | 0.096998 | 0.081968 | 0.714 | 0.01401 |
| Eukaryotic translation initia | EIF3E | WIVNLIR | 111 | NaN | 0.1375 | 0.082782 | 0.714 | 0.01401 |
| Endoplasmic reticulum lipid | ERLIN2 | ADAECYTAMK | 112 | 0.50502 | 2.1428 | 1.9075 | 0.186 | 0.05364 |
| Endoplasmic reticulum lipid | ERLIN2 | DIPNMFMDSAGSVSK | 113 | NaN | 0.36952 | 0.33782 | 0.186 | 0.05364 |
| Endoplasmic reticulum lipid | ERLIN2 | LSFGLEDEPLETATK | 114 | 0.46716 | 0.51738 | 4.6718 | 0.186 | 0.05364 |
| Endoplasmic reticulum lipid | ERLIN2 | LTPEYLQLMK | 115 | 0.76436 | 0.99457 | 0.95839 | 0.186 | 0.05364 |
| Endoplasmic reticulum lipid | ERLIN2 | VAQVAEITYGQK | 117 | NaN | 3.8443 | 4.775 | 0.186 | 0.05364 |
| Flap endonuclease 1 | FEN1 | EAHQLFLEPEVLDPESVELK | 129 | 0.55946 | 0.53151 | 0.62173 | 0.883 | 0.07927 |
| Flap endonuclease 1 | FEN1 | HLTASEAK | 130 | 0.57294 | NaN | NaN | 0.883 | 0.07927 |
| Flap endonuclease 1 | FEN1 | KLPIQEFHLSR | 254 | NaN | 0.50335 | 0.51855 | 0.883 | 0.07927 |
| Flap endonuclease 1 | FEN1 | LDPNKYPVPENWLHK | 131 | 0.45538 | 0.53912 | 0.63616 | 0.883 | 0.07927 |
| Flap endonuclease 1 | FEN1 | LPIQEFHLSR | 132 | NaN | 0.56689 | 0.65691 | 0.883 | 0.07927 |
| Flap endonuclease 1 | FEN1 | SIEEIVR | 133 | 0.46634 | 0.2953 | NaN | 0.883 | 0.07927 |
| Flap endonuclease 1 | FEN1 | VYAAATEDMDCLTFGSPVLMR | 134 | 0.25573 | 0.23882 | 0.2507 | 0.883 | 0.07927 |
| Flap endonuclease 1 | FEN1 | YPVPENWLHK | 135 | 0.48958 | 0.15763 | 0.65879 | 0.883 | 0.07927 |
| Heat shock 70 kDa protein 4 | HSPA4 | EDQYDHLDAADMTK | 140 | NaN | NaN | 0.64887 | 0.769 | 0.26011 |
| Heat shock 70 kDa protein 4 | HSPA4 | LNLQNK | 141 | 2.3137 | NaN | 2.1319 | 0.769 | 0.26011 |
| Heat shock 70 kDa protein 4 | HSPA4 | NKEDQYDHLDAADMTK | 142 | 0.76949 | 0.53896 | 0.54666 | 0.769 | 0.26011 |
| Heat shock 70 kDa protein 4 | HSPA4 | QSLTMDPVVK | 144 | 0.50413 | 0.4421 | 0.54603 | 0.769 | 0.26011 |
| Heat shock 70 kDa protein 4 | HSPA4 | STNEAMEWMNNK | 145 | 0.056431 | 0.045314 | 0.041474 | 0.769 | 0.26011 |

SUPPL. TABLE 4-continued

All identification and quantification information of the experiment in which heavy PrESTs were spiked into unlabeled HeLa lysate

| Protein Names | Gene Name | Sequence | SEQ ID NO. | Ratio H/L Mastermix1 | Ratio H/L Mastermix2 | Ratio H/L Mastermix3 | Protein Conc. μg/μl | μl PrESTs (1 + 2) |
|---|---|---|---|---|---|---|---|---|
| 39S ribosomal protein L50, | MRPL50 | AYTPPEDLQSR | 155 | 0.65073 | NaN | NaN | 0.684 | 0.01462 |
| 39S ribosomal protein L50, | MRPL50 | LESYVK | 157 | 1.131 | NaN | NaN | 0.684 | 0.01462 |
| 28S ribosomal protein S23, | MRPS23 | ALLAEGVILR | 158 | NaN | 0.91056 | 0.4868 | 0.407 | 0.02459 |
| 28S ribosomal protein S23, | MRPS23 | LFVETGK | 255 | NaN | 1.0838 | NaN | 0.407 | 0.02459 |
| 28S ribosomal protein S23, | MRPS23 | LGETDEEK | 159 | 0.93474 | 1.0182 | 1.0733 | 0.407 | 0.02459 |

| μl PrESTs (3) | NanoMate pmol/μl | NanoMate pmol/μl | NanoMate pmol/μl | pmol PrEST 1 | pmol PrEST 2 | pmol PrEST 3 | pmol Protein 1 | pmol Protein 2 | pmol Protein 3 |
|---|---|---|---|---|---|---|---|---|---|
| 0.58542 | 7.2168512 | 13.696164 | 7.5470525 | 4.224889 | 8.018008 | 4.418195 | | | 4.56346 |
| 0.58542 | 7.2168512 | 13.696164 | 7.5470525 | 4.224889 | 8.018008 | 4.418195 | 2.680087 | 5.337511 | 2.66526 |
| 0.58542 | 7.2168512 | 13.696164 | 7.5470525 | 4.224889 | 8.018008 | 4.418195 | | 5.764204 | |
| 0.58542 | 7.2168512 | 13.696164 | 7.5470525 | 4.224889 | 8.018008 | 4.418195 | 8.391041 | 12.6803 | 47.99309 |
| 0.01401 | 19.370034 | 20.330459 | 17.530494 | 0.2713742 | 0.28483 | 0.245602 | 2.267498 | 2.286871 | 5.103105 |
| 0.01401 | 19.370034 | 20.330459 | 17.530494 | 0.2713742 | 0.28483 | 0.245602 | | 3.20037 | |
| 0.01401 | 19.370034 | 20.330459 | 17.530494 | 0.2713742 | 0.28483 | 0.245602 | 2.810828 | 2.936449 | 2.996318 |
| 0.01401 | 19.370034 | 20.330459 | 17.530494 | 0.2713742 | 0.28483 | 0.245602 | | 2.071489 | 2.966855 |
| 0.05364 | 24.33193 | 24.52011 | 22.095083 | 1.3051647 | 1.315259 | 1.18518 | 2.584382 | 0.613804 | 0.621326 |
| 0.05364 | 24.33193 | 24.52011 | 22.095083 | 1.3051647 | 1.315259 | 1.18518 | | 3.559371 | 3.508319 |
| 0.05364 | 24.33193 | 24.52011 | 22.095083 | 1.3051647 | 1.315259 | 1.18518 | 0.279383 | 2.254215 | 0.253688 |
| 0.05364 | 24.33193 | 24.52011 | 22.095083 | 1.3051647 | 1.315259 | 1.18518 | 1.707526 | 1.32244 | 1.236637 |
| 0.05364 | 24.33193 | 24.52011 | 22.095083 | 1.3051647 | 1.315259 | 1.18518 | | 0.342132 | 0.248205 |
| 0.07927 | 20.539053 | 20.564795 | 16.396092 | 1.6281308 | 1.630171 | 1.299718 | 2.910183 | 3.067057 | 2.090487 |
| 0.07927 | 20.539053 | 20.564795 | 16.396092 | 1.6281308 | 1.630171 | 1.299718 | 2.841713 | | |
| 0.07927 | 20.539053 | 20.564795 | 16.396092 | 1.6281308 | 1.630171 | 1.299718 | | 3.238644 | 2.506447 |
| 0.07927 | 20.539053 | 20.564795 | 16.396092 | 1.6281308 | 1.630171 | 1.299718 | 3.575323 | 3.023763 | 2.043068 |
| 0.07927 | 20.539053 | 20.564795 | 16.396092 | 1.6281308 | 1.630171 | 1.299718 | | 2.87564 | 1.978533 |
| 0.07927 | 20.539053 | 20.564795 | 16.396092 | 1.6281308 | 1.630171 | 1.299718 | 3.491296 | 5.52039 | |
| 0.07927 | 20.539053 | 20.564795 | 16.396092 | 1.6281308 | 1.630171 | 1.299718 | 6.366601 | 6.825941 | 5.184357 |
| 0.07927 | 20.539053 | 20.564795 | 16.396092 | 1.6281308 | 1.630171 | 1.299718 | 3.325566 | 10.34176 | 1.972887 |
| 0.26011 | | 32.693479 | 24.878715 | 0 | 8.503901 | 6.471203 | | | 9.973034 |
| 0.26011 | | 32.693479 | 24.878715 | 0 | 8.503901 | 6.471203 | 0 | | 3.035416 |
| 0.26011 | | 32.693479 | 24.878715 | 0 | 8.503901 | 6.471203 | 0 | 15.77835 | 11.83771 |
| 0.26011 | | 32.693479 | 24.878715 | 0 | 8.503901 | 6.471203 | 0 | 19.23524 | 11.85137 |
| 0.26011 | | 32.693479 | 24.878715 | 0 | 8.503901 | 6.471203 | 0 | 187.6661 | 156.0303 |
| 0.01402 | 23.657325 | 15.986181 | 18.15397 | 0.3458701 | 0.233718 | 0.254519 | 0.531511 | | |
| 0.01402 | 23.657325 | 15.986181 | 18.15397 | 0.3458701 | 0.233718 | 0.254519 | 0.305809 | | |
| 0.02459 | 14.832962 | 15.409572 | 12.873057 | 0.3647425 | 0.378921 | 0.316548 | | 0.416141 | 0.650264 |
| 0.02459 | 14.832962 | 15.409572 | 12.873057 | 0.3647425 | 0.378921 | 0.316548 | | 0.349623 | |
| 0.02459 | 14.832962 | 15.409572 | 12.873057 | 0.3647425 | 0.378921 | 0.316548 | 0.390207 | 0.372148 | 0.29493 |

| Protein Names | Gene Name | Sequence | SEQ ID NO. | Ratio H/L Mastermix1 | Ratio H/L Mastermix2 | Ratio H/L Mastermix3 | Protein Conc. μg/μl | μl PrESTs (1 + 2) |
|---|---|---|---|---|---|---|---|---|
| 28S ribosomal protein S23, | MRPS23 | TQHGGSHVSR | 160 | NaN | 1.0302 | NaN | 0.407 | 0.02459 |
| 28S ribosomal protein S23, | MRPS23 | YTELQK | 161 | NaN | NaN | 1.1676 | 0.407 | 0.02459 |
| 28S ribosomal protein S28, | MRPS28 | AGGFASALER | 162 | NaN | 0.51434 | NaN | 0.449 | 0.02229 |
| 28S ribosomal protein S28, | MRPS28 | HSELLQK | 163 | 0.58177 | NaN | NaN | 0.449 | 0.02229 |
| Purine nucleoside phosphor | NP | ACVMMAQGR | 165 | 0.50497 | 0.63931 | 0.56821 | 1.085 | 0.09389 |
| Purine nucleoside phosphor | NP | DHINLPGFSGQNPLR | 166 | 0.95404 | 0.985 | 0.93693 | 1.065 | 0.09389 |
| Purine nucleoside phosphor | NP | FEVGDIMLIR | 167 | 0.68963 | 0.70356 | 0.71547 | 1.065 | 0.09389 |
| Purine nucleoside phosphor | NP | FHMYEGYPLWK | 168 | 0.72381 | 0.90091 | 0.76466 | 1.065 | 0.09389 |
| Purine nucleoside phosphor | NP | HRPQVAILCGSGLGGLTDK | 169 | NaN | 0.85363 | 0.81538 | 1.065 | 0.09389 |
| Purine nucleoside phosphor | NP | LTQAQIFDYGEIPNFPR | 170 | 1.118 | 1.8464 | 1.8793 | 1.065 | 0.09389 |
| Purine nucleoside phosphor | NP | LVFGFLNGR | 256 | 1.1247 | 0.30888 | 1.2496 | 1.065 | 0.09389 |

SUPPL. TABLE 4-continued

All identification and quantification information of the experiment in which heavy PrESTs were spiked into unlabeled HeLa lysate

| Protein | Gene | Peptide | # | Val1 | Val2 | Val3 | Val4 | Val5 | μl PrESTs | NanoMate pmol/μl | NanoMate pmol/μl | NanoMate pmol/μl | pmol PrEST 1 | pmol PrEST 2 | pmol PrEST 3 | pmol Protein 1 | pmol Protein 2 | pmol Protein 3 |
|---|---|---|---|---|---|---|---|---|---|---|---|---|---|---|---|---|---|---|
| Purine nucleoside phosphor | NP | STVPGHAGR | 171 | 1.0994 | NaN | 0.49901 | 1.065 | 0.09389 | 0.02459 | 14.832962 | 15.409572 | 12.873057 | 0.3647425 | 0.378921 | 0.316548 | | 0.367813 | |
| Purine nucleoside phosphor | NP | VFHLLGVDTLVVTNAAGGLNPK | 172 | NaN | 1.0676 | 1.0636 | 1.065 | 0.09389 | 0.02459 | 14.832962 | 15.409572 | 12.873057 | 0.3647425 | 0.378921 | 0.316548 | | | 0.27111 |
| Poly[ADP-ribose]polymera | PARP4 | AEGILLLVK | 174 | NaN | 0.58019 | 0.44594 | 0.579 | 0.01727 | 0.02229 | 11.385909 | 11.881033 | 10.583484 | 0.2537919 | 0.264828 | 0.235906 | | 0.514889 | |
| Prefoldin subunit 1 | PFDN1 | EAIHSQLLEK | 177 | 0.76453 | NaN | NaN | 0.441 | 0.09078 | 0.02229 | 11.385909 | 11.881033 | 10.583484 | 0.2537919 | 0.264828 | 0.235906 | 0.436241 | | |
| Prefoldin subunit 1 | PFDN1 | LADIQIEQLNR | 179 | 1.6259 | 1.8677 | 1.9142 | 0.441 | 0.09078 | 0.09389 | 18.081184 | 27.459079 | 20.854165 | 1.6976424 | 2.578133 | 1.957998 | 3.361868 | 4.03268 | 3.445905 |
| Prefoldin subunit 1 | PFDN1 | MFILQSK | 180 | 1.1344 | NaN | NaN | 0.441 | 0.09078 | 0.09389 | 18.081184 | 27.459079 | 20.854165 | 1.6976424 | 2.578133 | 1.957998 | 1.779425 | 2.617394 | 2.089801 |
| Peroxiredoxin 6 | PRDX6 | DFTPVCTTELGR | 187 | 0.56628 | NaN | 0.33394 | 0.714 | 0.56054 | 0.09389 | 18.081184 | 27.459079 | 20.854165 | 1.6976424 | 2.578133 | 1.957998 | 2.461671 | 3.664411 | 2.736659 |
| Peroxiredoxin 6 | PRDX6 | DINAYNCEEPTEK | 188 | 0.61696 | 0.60109 | 0.5663 | 0.714 | 0.56054 | 0.09389 | 18.081184 | 27.459079 | 20.854165 | 1.6976424 | 2.578133 | 1.957998 | 2.345425 | 2.861699 | 2.560612 |
| Peroxiredoxin 6 | PRDX6 | ELAILLGMLDPAEK | 189 | 0.57928 | 0.38932 | 0.38813 | 0.714 | 0.56054 | 0.09389 | 18.081184 | 27.459079 | 20.854165 | 1.6976424 | 2.578133 | 1.957998 | | 3.020199 | 2.401331 |
| Peroxiredoxin 6 | PRDX6 | FLAILLGMLDPAFKDEK | 190 | 0.56863 | 0.74994 | 0.21052 | 0.714 | 0.56054 | 0.09389 | 18.081184 | 27.459079 | 20.854165 | 1.6976424 | 2.578133 | 1.957998 | 1.518464 | 1.396302 | 1.041876 |
| Peroxiredoxin 6 | PRDX6 | FHDFLGDSWGILFSHPR | 191 | NaN | 0.57213 | 0.59897 | 0.714 | 0.56054 | 0.09389 | 18.081184 | 27.459079 | 20.854165 | 1.6976424 | 2.578133 | 1.957998 | 1.509418 | 8.346714 | 1.566899 |
| Peroxiredoxin 6 | PRDX6 | GMPVTAR | 192 | NaN | 0.59916 | 0.51841 | 0.714 | 0.56054 | 0.09389 | 18.081184 | 27.459079 | 20.854165 | 1.6976424 | 2.578133 | 1.957998 | 1.544154 | | 3.923764 |
| Peroxiredoxin 6 | PRDX6 | LAPEFAK | 193 | 0.80521 | 0.6713 | 0.74114 | 0.714 | 0.56054 | 0.09389 | 18.081184 | 27.459079 | 20.854165 | 1.6976424 | 2.578133 | 1.957998 | | 2.414887 | 1.840915 |
| Peroxiredoxin 6 | PRDX6 | LIALSIDSVEDHLAWSK | 194 | 0.74873 | 0.66939 | 0.62365 | 0.714 | 0.56054 | 0.01727 | 19.772134 | 22.931238 | | 0.3414648 | 0.396022 | 0 | | 0.682574 | 0 |
| Peroxiredoxin 6 | PRDX6 | LPFPIIDDR | 195 | 0.66166 | 0.68947 | 0.66519 | 0.714 | 0.56054 | 0.09078 | 16.010502 | 16.223891 | | 1.4534334 | 1.472805 | 0 | 1.901081 | | |
| Peroxiredoxin 6 | PRDX6 | VVGVFGPDK | 196 | 0.52861 | 0.25261 | 0.63133 | 0.714 | 0.56054 | 0.09078 | 16.010502 | 16.223891 | | 1.4534334 | 1.472805 | 0 | 0.893925 | 0.788566 | 0 |
| Peroxiredoxin 6 | PRDX6 | VVFVFGPDKK | 197 | 0.84361 | 0.36625 | 0.63578 | 0.714 | 0.56054 | 0.09078 | 16.010502 | 16.223891 | | 1.4534334 | 1.472805 | 0 | 1.281235 | | |
| 26S protease regulatory sub | PSMC3 | AVCVEAGMIALR | 198 | NaN | 0.27688 | 0.067813 | 0.672 | 0.04466 | 0.56054 | 19.343405 | 19.903505 | 12.598777 | 10.842752 | 11.15671 | 7.062119 | 19.14733 | | 21.14787 |
| 26S protease regulatory sub | PSMC3 | GATELTHEDYMEGILEVQAK | 199 | NaN | NaN | NaN | 0.672 | 0.04466 | 0.56054 | 19.343405 | 19.903505 | 12.598777 | 10.842752 | 11.15671 | 7.062119 | 17.57448 | 18.5608 | 12.47063 |
| 26S protease regulatory sub | PSMC3 | MNVSPDVNYEELAR | 201 | 0.67529 | 0.53568 | 0.63201 | 0.672 | 0.04466 | 0.56054 | 19.343405 | 19.903505 | 12.598777 | 10.842752 | 11.15671 | 7.062119 | 18.71764 | 28.65692 | 18.19524 |
| FACT complex subunit SSRP | SSRP1 | ADVIQATGDAICIFR | 209 | 0.51416 | 0.56819 | 0.54776 | 0.587 | 0.05111 | 0.56054 | 19.343405 | 19.903505 | 12.598777 | 10.842752 | 11.15671 | 7.062119 | 19.0682 | 14.8768 | 33.54607 |
| | | | | | | | | | 0.56054 | 19.343405 | 19.903505 | 12.598777 | 10.842752 | 11.15671 | 7.062119 | | 19.50031 | 11.79044 |
| | | | | | | | | | 0.56054 | 19.343405 | 19.903505 | 12.598777 | 10.842752 | 11.15671 | 7.062119 | | 18.62059 | 13.62265 |
| | | | | | | | | | 0.56054 | 19.343405 | 19.903505 | 12.598777 | 10.842752 | 11.15671 | 7.062119 | 13.46574 | 16.61956 | 9.528724 |
| | | | | | | | | | 0.56054 | 19.343405 | 19.903505 | 12.598777 | 10.842752 | 11.15671 | 7.062119 | 14.48153 | 16.66698 | 11.32385 |

SUPPL. TABLE 4-continued

All identification and quantification information of the
experiment in which heavy PrESTs were spiked into unlabeled HeLa lysate

| | | | | | | | | | |
|---|---|---|---|---|---|---|---|---|---|
| 0.56054 | 19.343405 | 19.903505 | 12.598777 | 10.842752 | 11.15671 | 7.062119 | 16.3872 | 16.18158 | 10.61669 |
| 0.56054 | 19.343405 | 19.903505 | 12.598777 | 10.842752 | 11.15671 | 7.062119 | 20.51182 | 44.16575 | 11.1861 |
| 0.56054 | 19.343405 | 19.903505 | 12.598777 | 10.842752 | 11.15671 | 7.062119 | 12.8528 | 30.46201 | 11.1078 |
| 0.04466 | 34.506036 | 32.565659 | 25.92524 | 1.5410396 | 1.454382 | 1.157821 | | 5.252753 | 17.07374 |
| 0.04466 | 34.506036 | 32.565659 | 25.92524 | 1.5410396 | 1.454382 | 1.157821 | | | |
| 0.04466 | 34.506036 | 32.565659 | 25.92524 | 1.5410396 | 1.454382 | 1.157821 | 2.282041 | 2.715021 | 1.831967 |
| 0.05111 | 18.671463 | 16.96063 | 13.294863 | 0.9542985 | 0.866858 | 0.6795 | 1.856034 | 1.525648 | 1.240508 |

| Protein Names | Gene Name | Sequence | SEQ ID NO. | Ratio H/L Mastermix1 | Ratio H/L Mastermix2 | Ratio H/L Mastermix3 | Protein Conc. µg/µl | µl PrESTs (1 + 2) |
|---|---|---|---|---|---|---|---|---|
| FACT complex subunit SSRP | SSRP1 | ELQCLTPR | 210 | NaN | 0.48128 | NaN | 0.587 | 0.05111 |
| FACT complex subunit SSRP | SSRP1 | IPYTTVLR | 211 | 0.61437 | 0.57615 | NaN | 0.587 | 0.05111 |
| THO complex subunit 1 | THOC1 | AVNNSNYGWR | 213 | NaN | NaN | 0.96021 | 0.953 | 0.0105 |
| THO complex subunit 1 | THOC1 | LWNLCPDNMEACK | 214 | 0.17972 | 0.064595 | 0.05542 | 0.953 | 0.0105 |
| THO complex subunit 1 | THOC1 | SLPEYLENMVIK | 215 | NaN | 0.063485 | 0.08477 | 0.953 | 0.0105 |
| THO complex subunit 1 | THOC1 | TGEDEDEEDNDALLK | 216 | 1.9103 | 2.2196 | 1.3318 | 0.953 | 0.0105 |
| Nucleoprotein TPR | TPR | ILLSQTTGVAIPLHASSLDDVSLASTPK | 257 | 2.5182 | 2.6647 | 2.8484 | 0.388 | 0.07732 |
| Nucleoprotein TPR | TPR | ITELQLK | 217 | NaN | NaN | 2.4635 | 0.388 | 0.07732 |
| Nucleoprotein TPR | TPR | LESALTELEQLR | 218 | 2.3557 | 2.4601 | 2.3322 | 0.388 | 0.07732 |
| Nucleoprotein TPR | TPR | LESALTELEQLRK | 219 | NaN | NaN | 2.7043 | 0.388 | 0.07732 |
| Nucleoprotein TPR | TPR | NIEELQQQNQR | 220 | NaN | 2.2529 | 2.0753 | 0.388 | 0.07732 |
| Nucleoprotein TPR | TPR | QHQMQLVDSIVR | 221 | 1.8112 | NaN | 1.9585 | 0.388 | 0.07732 |
| Cytochrome b-c1 complex s | UQCRC1 | ADLTEYLSTHYK | 222 | 0.21817 | 0.21768 | 0.25733 | 0.43 | 0.02326 |
| Cytochrome b-c1 complex s | UQCRC1 | DVVFNYLHATAFQGTPLAQAVEGPSENVR | 258 | 0.20672 | 0.22361 | 0.25427 | 0.43 | 0.02326 |
| Cytochrome b-c1 complex s | UQCRC1 | MVLAAAGGVEHQQLLDLAQK | 223 | 0.036719 | 0.16497 | 0.15532 | 0.43 | 0.02326 |
| Vimentin | VIM | DNLAEDIMR | 233 | 0.38208 | 0.423 | 0.40237 | 0.427 | 1.17023 |
| Vimentin | VIM | EEAENTLQSFR | 234 | 0.53572 | 0.51411 | 0.5603 | 0.427 | 1.17023 |
| Vimentin | VIM | EKLQEEMLQR | 235 | 0.35844 | 0.35626 | 0.35986 | 0.427 | 1.17023 |
| Vimentin | VIM | ILLAELEQLK | 236 | 0.60792 | 0.60021 | 0.62632 | 0.427 | 1.17023 |
| Vimentin | VIM | ILLAELEQLKGQGK | 237 | 0.45207 | NaN | NaN | 0.427 | 1.17023 |
| Vimentin | VIM | LGDLYEEEMR | 238 | 0.41358 | 0.39183 | 0.30821 | 0.427 | 1.17023 |
| Vimentin | VIM | LQEEMLQR | 239 | 0.43217 | 0.27333 | 0.38427 | 0.427 | 1.17023 |
| Vimentin | VIM | QDVDNASLAR | 240 | 0.50789 | 0.50041 | 0.51027 | 0.427 | 1.17023 |
| Vimentin | VIM | QVDQLTNDK | 241 | 0.57376 | 0.52999 | 0.5087 | 0.427 | 1.17023 |
| Vimentin | VIM | RQVDQLTNDK | 242 | 0.5666 | 0.51939 | 0.6736 | 0.427 | 1.17023 |

| µl PrESTs (3) | NanoMate pmol/µl | NanoMate pmol/µl | NanoMate pmol/µl | pmol PrEST 1 | pmol PrEST 2 | pmol PrEST 3 | pmol Protein 1 | pmol Protein 2 | pmol Protein 3 |
|---|---|---|---|---|---|---|---|---|---|
| 0.05111 | 18.671463 | 16.96063 | 13.294863 | 0.9542985 | 0.866858 | 0.6795 | | 1.801151 | |
| 0.05111 | 18.671463 | 16.96063 | 13.294863 | 0.9542985 | 0.866858 | 0.6795 | 1.553296 | 1.50457 | |
| 0.0105 | 26.314913 | 19.802314 | 20.98021 | 0.2763066 | 0.207924 | 0.220292 | | | 0.229421 |
| 0.0105 | 26.314913 | 19.802314 | 20.98021 | 0.2763066 | 0.207924 | 0.220292 | 1.537428 | 3.218892 | 3.974959 |
| 0.0105 | 26.314913 | 19.802314 | 20.98021 | 0.2763066 | 0.207924 | 0.220292 | | 3.275172 | 2.598705 |
| 0.0105 | 26.314913 | 19.802314 | 20.98021 | 0.2763066 | 0.207924 | 0.220292 | 0.14464 | 0.093676 | 0.165409 |

SUPPL. TABLE 4-continued

All identification and quantification information of the
experiment in which heavy PrESTs were spiked into unlabeled HeLa lysate

| | | | | | | | | | |
|---|---|---|---|---|---|---|---|---|---|
| 0.07732 | 16.099976 | 16.486454 | 15.642843 | 1.2448502 | 1.274733 | 1.209505 | 0.494341 | 0.478378 | 0.424626 |
| 0.07732 | 16.099976 | 16.486454 | 15.642843 | 1.2448502 | 1.274733 | 1.209505 | | | 0.49097 |
| 0.07732 | 16.099976 | 16.486454 | 15.642843 | 1.2448502 | 1.274733 | 1.209505 | 0.528442 | 0.518163 | 0.518611 |
| 0.07732 | 16.099976 | 16.486454 | 15.642843 | 1.2448502 | 1.274733 | 1.209505 | | | 0.447252 |
| 0.07732 | 16.099976 | 16.486454 | 15.642843 | 1.2448502 | 1.274733 | 1.209505 | | 0.565819 | 0.58281 |
| 0.07732 | 16.099976 | 16.486454 | 15.642843 | 1.2448502 | 1.274733 | 1.209505 | 0.687307 | | 0.617567 |
| 0.02326 | | 20.444076 | 15.780782 | 0 | 0.475529 | 0.667061 | 0 | 2.184533 | 1.426421 |
| 0.02326 | | 20.444076 | 15.780782 | 0 | 0.475529 | 0.667061 | 0 | 2.126601 | 1.443587 |
| 0.02326 | | 20.444076 | 15.780782 | 0 | 0.475529 | 0.667061 | 0 | 2.882519 | 2.363256 |
| 1.17023 | 14.055391 | 18.074527 | 15.696811 | 16.44804 | 21.15135 | 18.36888 | 43.04868 | 50.0032 | 45.65171 |
| 1.17023 | 14.055391 | 18.074527 | 15.696811 | 16.44804 | 21.15135 | 18.36888 | 30.70268 | 41.14169 | 32.78401 |
| 1.17023 | 14.055391 | 18.074527 | 15.696811 | 16.44804 | 21.15135 | 18.36888 | 45.88785 | 59.37055 | 51.04452 |
| 1.17023 | 14.055391 | 18.074527 | 15.696811 | 16.44804 | 21.15135 | 18.36888 | 27.05626 | 35.23992 | 29.32827 |
| 1.17023 | 14.055391 | 18.074527 | 15.696811 | 16.44804 | 21.15135 | 18.36888 | 36.38384 | | |
| 1.17023 | 14.055391 | 18.074527 | 15.696811 | 16.44804 | 21.15135 | 18.36888 | 39.76991 | 53.98094 | 59.59858 |
| 1.17023 | 14.055391 | 18.074527 | 15.696811 | 16.44804 | 21.15135 | 18.36888 | 38.05919 | 77.38394 | 47.80201 |
| 1.17023 | 14.055391 | 18.074527 | 15.696811 | 16.44804 | 21.15135 | 18.36888 | 32.38504 | 42.26805 | 35.99835 |
| 1.17023 | 14.055391 | 18.074527 | 15.696811 | 16.44804 | 21.15135 | 18.36888 | 28.66711 | 39.90897 | 36.10945 |
| 1.17023 | 14.055391 | 18.074527 | 15.696811 | 16.44804 | 21.15135 | 18.36888 | 29.02937 | 40.72345 | 27.26971 |

SUPPLEMENTARY TABLE 4b

| Gene Name | Protein Name | Mastermix 1 (pmol) | Mastermix 2 (pmol) | Mastermix 3 (pmol) | Copy Number 1 | Copy Number 2 | Copy Number 3 | Median | RSD (%) |
|---|---|---|---|---|---|---|---|---|---|
| AFG3L2 | AFG3-like protein 2 | 0.252619235 | 0.312927491 | 0 | 152,131 | | | 152,131 | |
| ATP5B | ATP synthase subunit beta, mitocl | 9.694065359 | 10.87839063 | 8.404284127 | 5,837,904 | 6,551,121 | 5,061,179 | 5,837,904 | 12.81 |
| AYTL2 | Lysophosphatidylcholine acyltrans | — | — | — | | | | | |
| C1orf65 | Uncharacterized protein C1orf65 | — | — | — | | | | | |
| CBR3 | Carbonyl reductase [NADPH]3 | 0.482912745 | 0.790843465 | 0.97898086 | 290,817 | 476,817 | 589,556 | 476,257 | 33.35 |
| CCT2 | T-complex protein 1 subunit beta | 0 | 6.874450414 | 5.87473498 | | 4,139,892 | 3,537,849 | 3,838,879 | 11.09 |
| COPSS | COP9 signalosome complex subun | 0.195802466 | 0.507321377 | 0 | 117,915 | 305,516 | | 211,716 | 62.66 |
| CYB5R4 | Cytochrome b5 reductase 4 | 0.021176576 | 0.019112892 | 0 | 12,753 | 11,510 | | 12,131 | 7.24 |
| DDX20 | Probable ATP-dependent RNA hel | 0.49657408 | — | — | 299,044 | | | 299,044 | |
| ECHS1 | Enoyl-CoA hydratase, mitochondri | 4.126271164 | 8.361653639 | 5.234584905 | 2,484,899 | 5,035,506 | 3,152,341 | 3,152,341 | 37.18 |
| EIF3E | Eukaryotic translation initiation fa | 2.539162992 | 2.611659997 | 2.996318259 | 1,529,120 | 1,572,779 | 1,804,425 | 1,572,779 | 9.05 |
| ERLIN2 | Endoplasmic reticulum lipid raft-a | 1.707526217 | 0.613803749 | 0.621326468 | 1,028,296 | 369,641 | 374,172 | 374,172 | 64.16 |
| FEN1 | Flap endonuclease 1 | 3.408430951 | 3.238643686 | 2.066777383 | 2,052,605 | | | 2,052,605 | |
| HSPA4 | Heat shock 70 kDa protein 4 | 0 | 19.23524295 | 11.83771012 | | 11,583,736 | 7,128,837 | 9,356,286 | 33.67 |
| MLKL | Mixed lineage kinase domain-like | — | — | — | | | | | |
| MRPL50 | 39S ribosomal protein L50, mitocl | 0.418660011 | — | — | 252,123 | | | 252,123 | |
| MRPS23 | 28S ribosomal protein S23, mitocl | 0.390207475 | 0.369980833 | 0.294930107 | 234,988 | | 177,611 | 206,300 | 19.67 |
| MRPS28 | 28S ribosomal protein S35, mitocl | 0.436240972 | 0.441351419 | 0.271110383 | 262,710 | 265,788 | 163,267 | 262,710 | 25.29 |
| NP | Purine nucleoside phosphorylase | 1.779424739 | 2.940949047 | 2.401331339 | 1,071,595 | 1,771,081 | 1,446,116 | 1,446,116 | 24.48 |
| PARP4 | Poly [ADP-ribose] polymerase 4 | — | 0.682573768 | 0 | | 411,056 | | 411,056 | |
| PFDN1 | Prefoldin subunit 1 | 1.281235376 | 0.788566037 | 0 | 771,578 | | | 771,578 | |
| PRDX6 | Peroxiredoxin 6 | 17.57448193 | 18.59069261 | 11.79043804 | 10,583,602 | 11,195579 | 7,100,369 | 10,583,602 | 22.95 |
| PSMC3 | 26S protease regulatory subunit 6 | 2.282041145 | 3.983887093 | 9.452851115 | 1,374,278 | 2,399,153 | 5,692,641 | 2,399,153 | 71.51 |
| SSRP1 | FACT complex subunit SSRP1 | 1.704665071 | 1.52567761 | 1.240507611 | 1,026,573 | 918,767 | 747,051 | 918,767 | 15.71 |
| THOC1 | THO complex subunit 1 | 0.841034292 | 3.218891514 | 1.414062794 | 506,483 | | 851,569 | 679,026 | 35.94 |
| TPR | Nucleoprotein TPR | 0.528441724 | 0.518162926 | 0.504790509 | 318,235 | 312,045 | 303,992 | 312,045 | 2.29 |
| UQCRC1 | Cytochrome b-c1 complex subunit | 0 | 2.184533321 | 1.443587459 | | 1,315,557 | 869,349 | 1,092453 | 28.88 |
| VIM | Vimentin | 34.38444006 | 42.26804731 | 36.10945422 | 20,706,797 | 25,454,417 | 21,745,625 | 21,745,625 | 11.03 |

SUPPLEMENTARY TABLE 4c

| Gene Name | Protein Name | forward experiment (light PrESTs) | | | | |
|---|---|---|---|---|---|---|
| | | Copy Number 1 | Copy Number 2 | Copy Number 3 | Median | RSD (%) |
| AFG3L2 | AFG3-like protein 2 | 369,737 | 412,509 | 165,983 | 369,737 | 41.68 |
| ATP5B | ATP synthase subunit beta, mitocl | 5,672,473 | 4,376,424 | 4,511,967 | 4,511,967 | 14.68 |
| AYTL2 | Lysophosphatidylcholine acyltransferase 1 | | | | | |
| C1orf65 | Uncharacterized protein C1orf65 | | | | | |
| CBR3 | Carbonyl reductase [NADPH]3 | 79,823 | 61,399 | 322,454 | 79,823 | 94.26 |
| CCT2 | T-complex protein 1 subunit beta | 7,447,762 | 2,757,533 | 4,479,130 | 4,479,130 | 48.47 |
| COPSS | COP9 signalosome complex subun | 323,791 | 284,218 | 435,937 | 323,791 | 22.62 |
| CYB5R4 | Cytochrome b5 reductase 4 | 16,205 | 10,180 | 9,515 | 10,180 | 30.8 |
| DDX20 | Probable ATP-dependent RNA heli | 242,403 | 184,529 | | 213,466 | 19.17 |
| ECHS1 | Enoyl-CoA hydratase, mitochondri | 2,965,394 | 1,723,133 | 2,105,336 | 2,105,336 | 28.1 |
| EIF3E | Eukaryotic translation initiation fa | 1,067,627 | 599,306 | 1,253,469 | 1,067,627 | 34.63 |
| ERLIN2 | Endoplasmic reticulum lipid raft-a | 206,262 | 148,785 | 149,867 | 149,867 | 19.53 |
| FEN1 | Flap endonuclease 1 | 2,373,346 | 2,019,699 | 1,563,785 | 2,019,699 | 20.42 |
| HSPA4 | Heat shock 70 kDa protein 4 | 2,146,713 | 1,499,858 | 1,646,549 | 1,646,549 | 19.22 |
| MLKL | Mixed lineage kinase domain-like | 128,711 | | 100,891 | 114,801 | 17.14 |
| MRPL50 | 39S ribosomal protein L50, mitoch | 177,937 | 250,001 | 194,935 | 194,935 | 18.14 |
| MRPS23 | 28S ribosomal protein S23, mitoch | 223,198 | 203,672 | 282,020 | 223,198 | 17.26 |
| MRPS28 | 28S ribosomal protein S35, mitoch | 473,409 | 284,783 | 422,825 | 422,825 | 24.8 |
| NP | Purine nucleoside phosphorylase | 2,101,680 | 1,357,920 | 1,555,814 | 1,555,814 | 23.04 |
| PARP4 | Poly [ADP-ribose] polymerase 4 | 60,775 | 67,168 | | 63,971 | 7.07 |
| PFDN1 | Prefoldin subunit 1 | 476,849 | 523,643 | 243,332 | 476,849 | 36.22 |
| PRDX6 | Peroxiredoxin 6 | 8,881,373 | 8,377,838 | 8,781,079 | 8,781,079 | 3.07 |
| PSMC3 | 26S protease regulatory subunit 6 | 1,062,048 | 950,200 | 1,192,875 | 1,062,048 | 11.37 |
| SSRP1 | FACT complex subunit SSRP1 | 1,095,695 | 1,022,209 | 1,209,724 | 1,095,695 | 8.52 |
| THOC1 | THO complex subunit 1 | 239,173 | 184,576 | 204,962 | 204,962 | 13.16 |
| TPR | Nucleoprotein TPR | 397,408 | 278,736 | 357,637 | 357,637 | 17.53 |
| UQCRC1 | Cytochrome b-c1 complex subunit | 1,022,450 | 713,318 | 1,025,854 | 1,022,450 | 19.5 |
| VIM | Vimentin | 22,974,646 | 17,376,010 | 22,886,339 | 22,886,339 | 15.22 |

| | Gene Name | reverse experiment (heavy PrESTs) | | | | | |
|---|---|---|---|---|---|---|---|
| | | Copy Number 1 | Copy Number 2 | Copy Number 3 | Median | RSD (%) | RSD (%) |
| | AFG3L2 | 152,131 | | | 152,131 | | 58.96924 |
| | ATP5B | 5,837,904 | 6,745,143 | 5,350,929 | 5,837,904 | 11.84 | 18.11769 |
| | AYTL2 | | | | | | |
| | C1orf65 | | | | | | |
| | CBR3 | 290,925 | 476,434 | 589,556 | 476,434 | 33.33 | 100.8334 |
| | CCT2 | | 4,139,892 | 3,537,849 | 3,838,870 | 11.09 | 10.8856 |
| | COPSS | 117,915 | 292,058 | | 205,487 | 60.27 | 31.61052 |
| | CYB5R4 | 12,753 | 7,618 | | 10,185 | 35.65 | 0.037884 |
| | DDX20 | 299,044 | | | 299,044 | | 23.61427 |
| | ECHS1 | 2,484,899 | 5,276,677 | 3,157,087 | 3,157,087 | 40.03 | 28.26456 |
| | EIF3E | 1,529,120 | 1,531,715 | 1,870,428 | 1,531,751 | 11.94 | 25.24945 |
| | ERLIN2 | 1,028,296 | 395,520 | 308,967 | 395,520 | 67.99 | 63.69902 |
| | FEN1 | 2,052,605 | | | 2,052,605 | | 1.142762 |
| | HSPA4 | | 11,287,790 | 7,120,698 | 9,204,244 | 32.01 | 98.50151 |
| | MLKL | | | | | | |
| | MRPL50 | 252,123 | | | 252,123 | | 18.09073 |
| | MRPS23 | 234,988 | | 162,252 | 198,620 | 25.89 | 8.240033 |
| | MRPS28 | 262,710 | 128,718 | 149,148 | 149,148 | 40.06 | 67.66706 |
| | NP | 1,071,595 | 1,785,222 | 1,476,153 | 1,476,153 | 24.78 | 3.715642 |
| | PARP4 | | 413,808 | | 413,808 | | 103.5509 |
| | PFDN1 | 771,578 | | | 771,578 | | 33.3868 |
| | PRDX6 | 10,583,602 | 9,447,065 | 6,349,191 | 9,447,065 | 24.92 | 5.166992 |
| | PSMC3 | 1,374,278 | 2,514,900 | 5,692,641 | 2,514,900 | 70.06 | 57.44122 |
| | SSRP1 | 1,026,573 | 911,155 | 747,051 | 911,155 | 15.70 | 13.00441 |

SUPPLEMENTARY TABLE 4c-continued

| THOC1 | 506,483 |  | 851,569 | 679,026 | 35.94 | 75.84125 |
|---|---|---|---|---|---|---|
| TPR | 318,235 | 315,936 | 303,992 | 315,936 | 2.45 | 8.755396 |
| UQCRC1 |  | 1,312,073 | 888,889 | 1,100,481 | 27.19 | 5.198108 |
| VIM | 20,706,797 | 25,128,776 | 21,745,625 | 21,745,625 | 10.26 | 3.614478 |

Figure 6A:
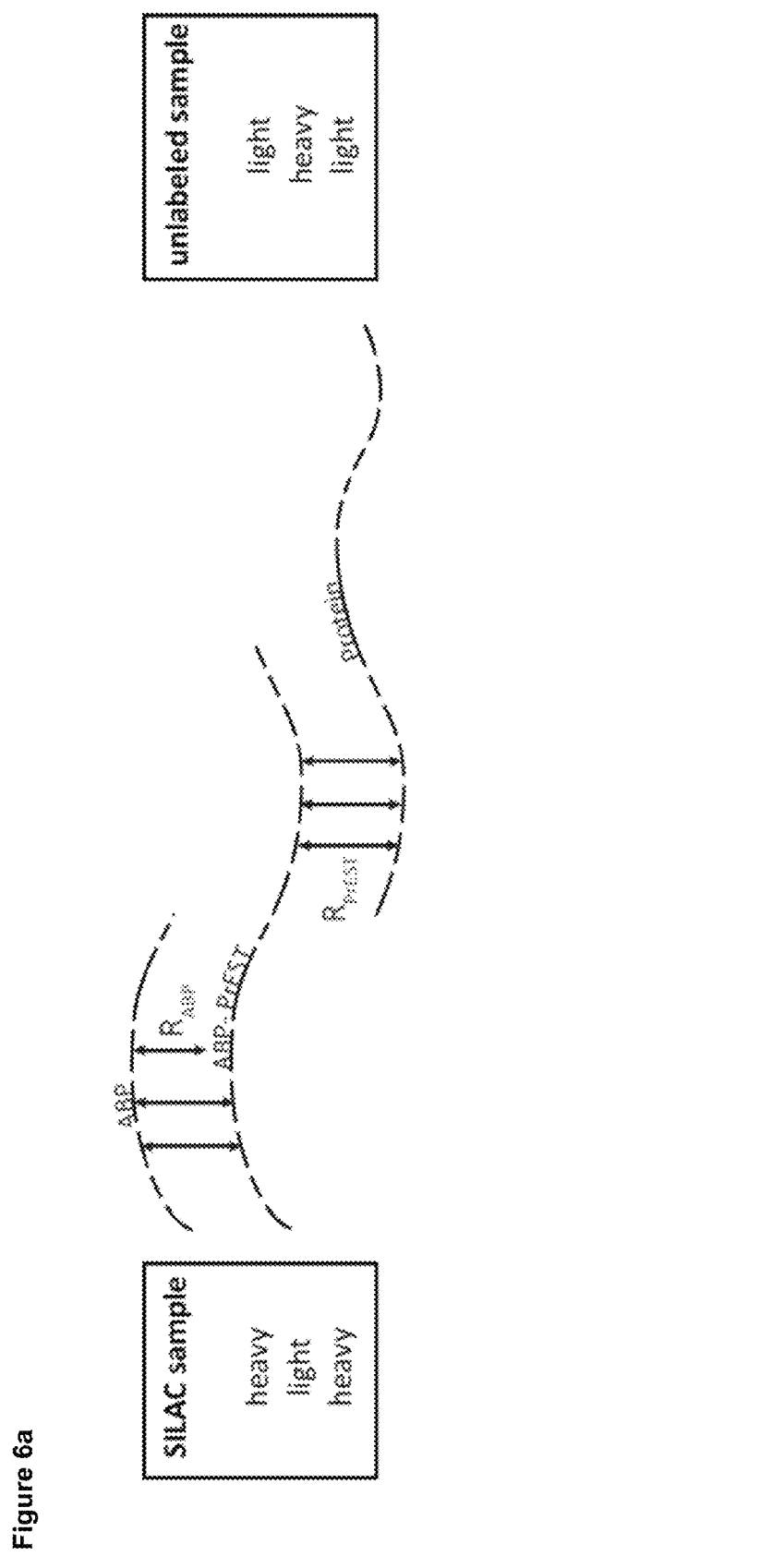
FIG. 6: Direct quantification of a single protein in HeLa cell lysate. (A) Principle of the 'single-plex' strategy for the direct quantification of a single protein. In the same experiment, SILAC peptide ratios mapping to the ABP quantification tag determine the amount of PrEST whereas SILAC ratios mapping to the protein specific region of the PrEST construct determine the level of the endogenous proteins. The experiment can be performed with SILAC heavy labeled cells, unlabeled PrEST construct and heavy labeled ABP tag (left side) or vice versa (right side). (B) Single-plex determination of absolute protein amount. In the workflow depicted here, an unlabeled PrEST construct as well as a heavy labeled ABP tag are both spiked into HeLa cell lysate before digestion. (C) Comparison of copy numbers obtained from the 'master mix' experiment with those from the single-plex experiments for three different proteins. Error bars are standard deviations of the mean from triplicate measurements.
Figure 6B:
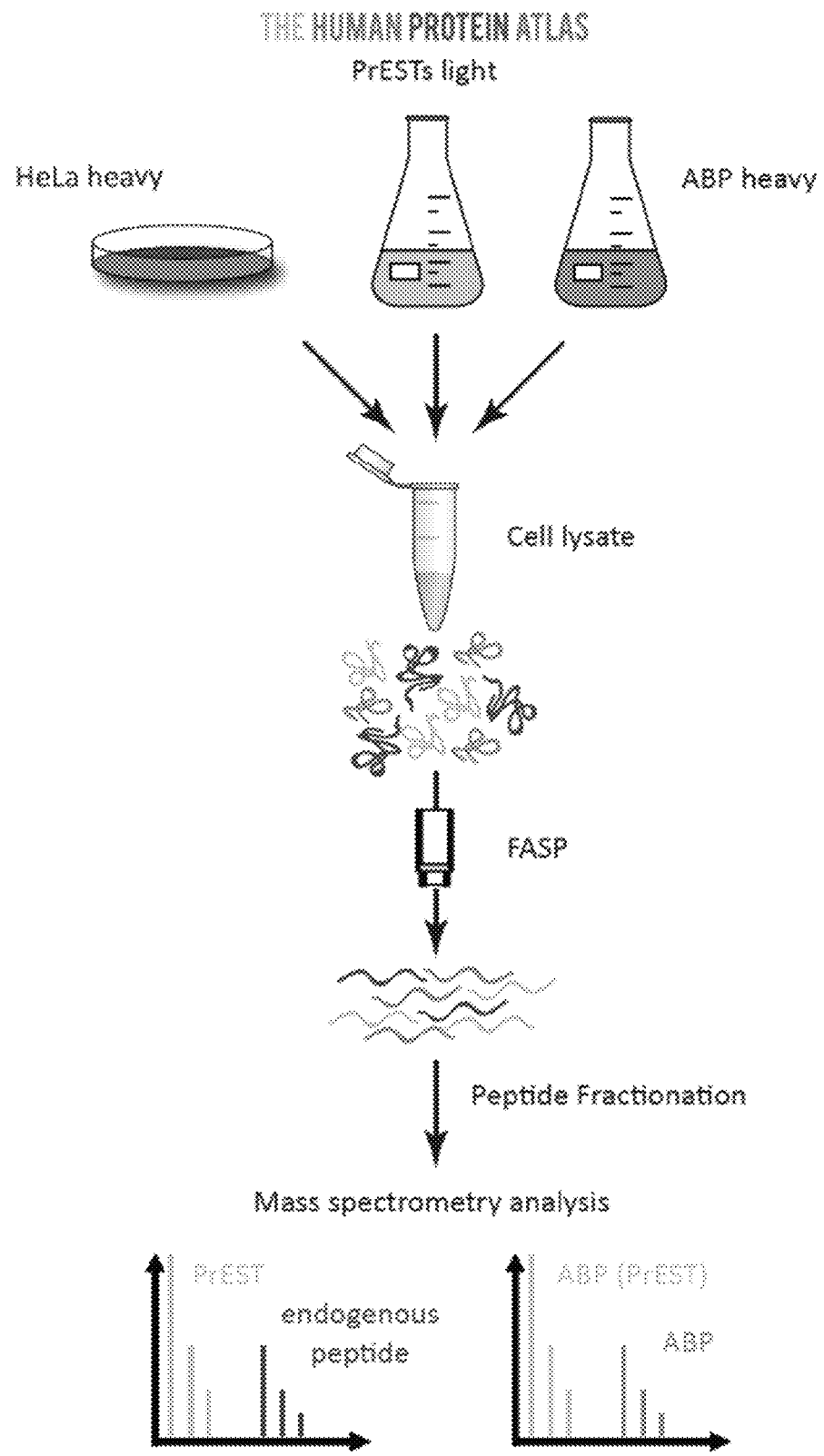

Absolute quantification in single experiments—We also wished to develop a variation on the SILAC-PrEST strategy to quantify single protein target. In this case, the two experimental steps involved in absolute protein quantification can be collapsed into one as outlined schematically in FIG. 6A. A precisely known amount of the ABP solubility tag is mixed into cell lysate together with the labeled PrEST. LC-MS/MS analysis of the sample then provides SILAC ratios of light ABP solubility tag to labeled PrEST ABP peptides. These ratios accurately quantify the amount of PrEST that was used. The same LC MS data also contain the ratios of labeled PrEST peptides to the unlabeled endogenous protein counterpart. Together, these ratios quantify the absolute amount of endogenous protein in a single experiment. Note that triple-SILAC labeling is not required in this approach because the ratios are determined against different regions of the PrEST construct, namely the common ABP solubility tag region (for quantifying the PrEST) and the protein specific PrEST region (for quantifying the endogenous protein).

Figure 6C:
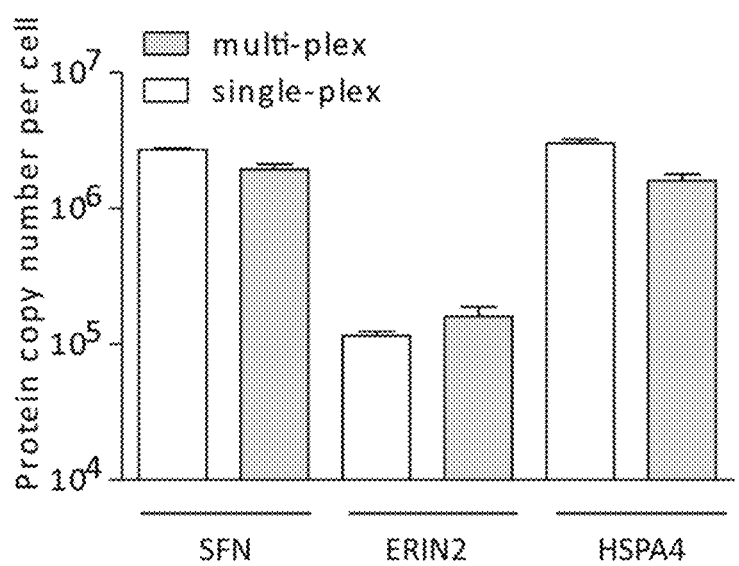

This single-plex method for quantification was performed for three different HeLa proteins in which the SILAC-labeled cell lysate and SILAC-labeled ABP was quantified against unlabeled PrESTs. As shown in FIG. 6C, consistent values were obtained in these measurements based on triplicate experiments. The absolute levels generally agreed well with the copy numbers determined independently in the multiplexed PrEST-SILAC experiment described above (maximum difference between the means of 40%), validating both approaches.

Figure 8:
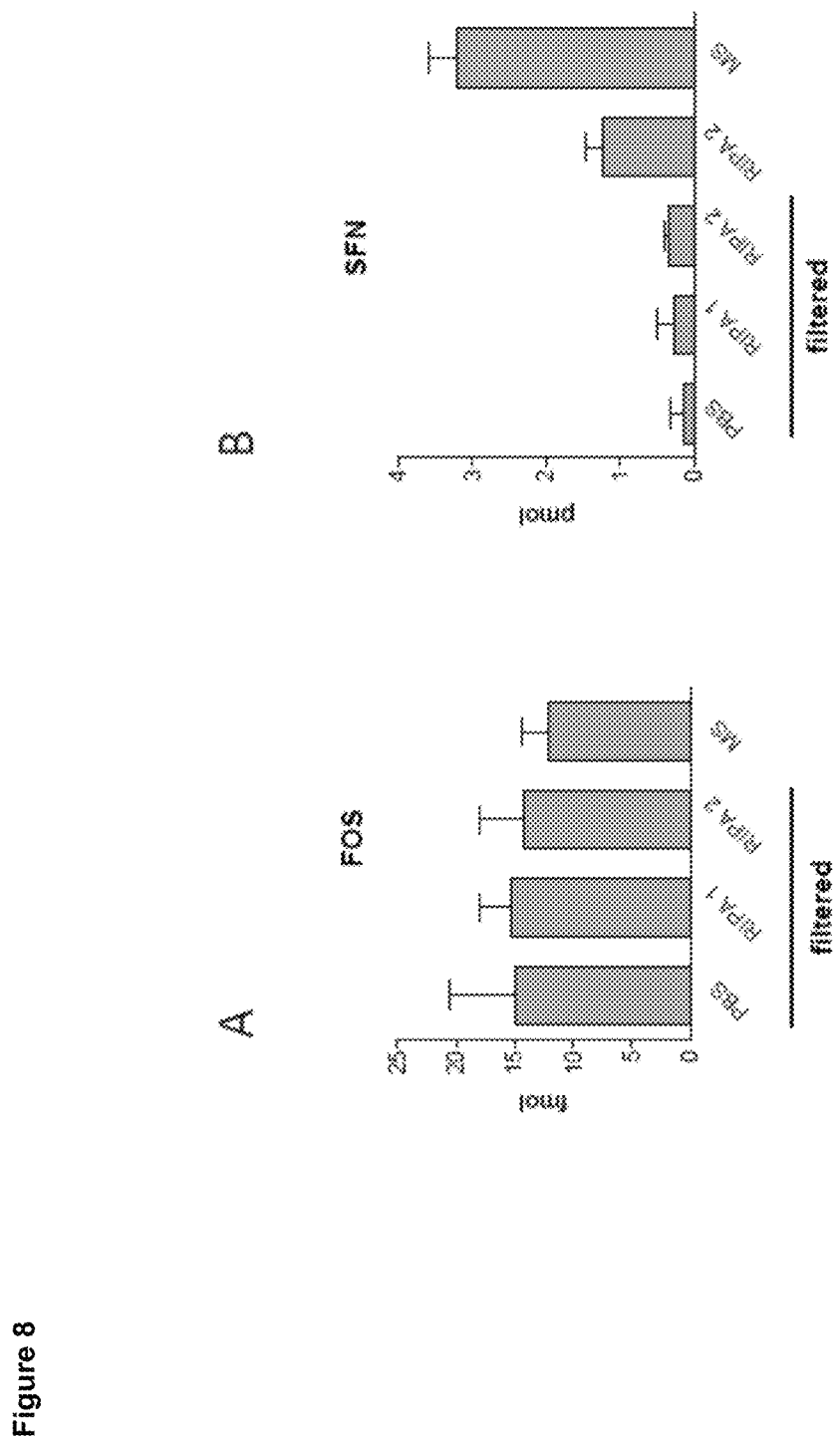
FIG. 8: Comparison of SILAC-PrEST based quantification and ELISA. Proto-oncogene c-Fos (A) and Stratifin (B) were quantified by ELISA to evaluate the SILAC-PrEST absolute quantification. Different ELISA compatible buffers and filtered vs. unfiltered cell lysates were compared.

Enzyme-linked immunosorbent assay—ELISA is a standard method in biochemical research to determine absolute amounts, or at least to reproducibly determine protein levels. We therefore compared the SILAC-PrEST method to this established technology. When performing the ELISA assay for Stratifin (14-3-3 σ) under typical conditions—filtered cell lysate and phosphate buffered saline (PBS) as recommended by the manufacturer—the ELISA recorded less than 20% of the amount quantified by MS. (Note that there is no interference by 14-3-3 isoforms because these peptides are different.) The recommendation of the manufacturer was PBS could not solubilize the pellet. The solubility was increased by adding the nonionic detergent NP-40, which was able to dissolve most of the sample pellet. Adding a low concentration of sodium dodecyl sulfate (SDS), an anionic detergent further improvement significantly increased measured protein amount (FIG. 8B). Still the absolute amounts were underestimated two-fold compared to mass spectrometry analysis, presumably because the FASP protocol enables complete solubilization by the use of 4% sodium dodecyl sulfate.

We also investigated the levels of the transcription factor and proto-oncogene FOS by ELISA, the lowest abundance protein quantified in our mix. Here solubilization did not appear to be an issue and we received excellent agreement between quantitative values determined by MS and by ELISA using different buffer conditions (FIG. 8A).

Example 3

Absolute Quantification Using Mouse PrESTs

Experimental procedure—The mouse PrESTs fused with a N-terminal His-tag were expressed in an auxotrophic E. coli strain using minimal media, supplemented with isotope labeled $^{13}C_6$ $^{15}N_2$-Lysine (Lys8) and $^{13}C_6$$^{15}N_4$-Arginine (Arg10) (Cambridge Isotopes Laboratories) to obtain 'heavy' labeled proteins. The bacteria were harvested by centrifugation, lysed in 7M guanidinium chloride, 47 mM $Na_2HPO_4$, 2.65 mM $NaH_2PO_4$, 10 mM Tris HCL, 300 mM NaCl, 10 mM beta-mercaptoethanol, pH 8.0 and the His-fusion PrESTs were enriched on a Cobalt Talon column (Clontech) and eluted in 6 M Urea, 50 mM $NaH_2PO_4$, 100 mM NaCl, 30 mM Acetic acid, 70 mM Na-acetate pH 5 (29).

Blood samples were drawn from mice into tubes containing heparin. The blood was centrifuged twice at 70 g and each time the supernatant, the platelet rich plasma (PRP), was retained. Apyrase and prostacyclin ($PGI_2$) were added to the PRP to inhibit platelet aggregation. The sample was centrifuged and the pellet was washed twice with 1 ml of Tyrode's buffer (without $Ca^{2+}$, containing BSA, apyrase and $PGI_2$). Eventually the pellet was resuspended in 300-400 µl Tyrode's buffer and incubated for 30 min at 37° C. A standard hematologic analysis was performed using the Hemavet 950 (Drew Scientific Inc.) to count platelets.

The isolated platelets were lysed in 4% SDS, 100 mM Tris pH 8.5, 100 mM DTT, boiled for 5 min at 95° C. and the purified PrESTs were added to the lysate in the appropriate amount. The samples were prepared in accordance with the previously described FASP method (30). Peptides were collected by centrifugation and eluted with water. Peptides were desalted on C18 empore stages tips and eluted in buffer B (80% acetonitrile, 0.5% acetic acid), organic solvent was removed by speed-vacing and the sample was resolved in A* (2% acetonitrile, 0.5% acetic acid). The peptides were loaded without prefractionation on an in-house packed 20 cm column (75 µm inner diameter) packed with 1.8 µm C18 resin (Dr. Maisch GmbH) and separated using an EASY-nLC 1000 (Thermo Fisher Scientific) on a 200 min 2-25% buffer B gradient. The separated peptides were sprayed via a nanoelectrospray ion source (Proxeon Biosystems) to a Q Exactive mass spectrometer (Thermo Fisher Scientific). The mass spectrometer acquired survey scans and the top 10 most abundant ions were sequentially fragmented with higher-energy collisional dissociation and MS/MS scans acquired. Raw data was analyzed using the Max Quant software as described in Example 1 except that the data was searched against the mouse IPI database version 3.68 containing 56,743 entries.

Results—To further broaden the approach to other species we designed PrESTs targeting mouse proteins. PrESTs were designed to span over a 125-200 amino acids region, yielding many tryptic peptides and including numerous peptides that were observed in the mass spectrometer in previous measurements. For each target protein we designed two PrESTs to cover different regions of the proteins and to ensure quantification precision. We designed PrESTs to measure the expression levels of Integrin beta 3 and its co-activators Talin 1 and Kindlin 3 in mouse platelets. The activation of the heterodimer Integrin αIIbβ3 (shifting from a low-affinity state to an high affinity state) plays an essential role in platelet adhesion and aggregation (31). Mice deficient of Kindlin 3 suffer from severe bleeding and die within several days. We determined expression levels of Integrin beta 3, Talin 1 and Kindlin 3 in wild-type mice (Kind3$^{+/+}$), Kind3$^{+/n}$, Kind3$^{n/n}$ and Kind3$^{n/-}$. 'n' indicates an insertion of a neomycin cassette into an intron of the gene, affecting splicing of Kindlin 3. To further elucidate functionality of Integrin activation we wished to measure the stoichiometry of Integrin beta 3, Talin 1 and Kindlin 3 in the wildtype mice.

Figure 9:
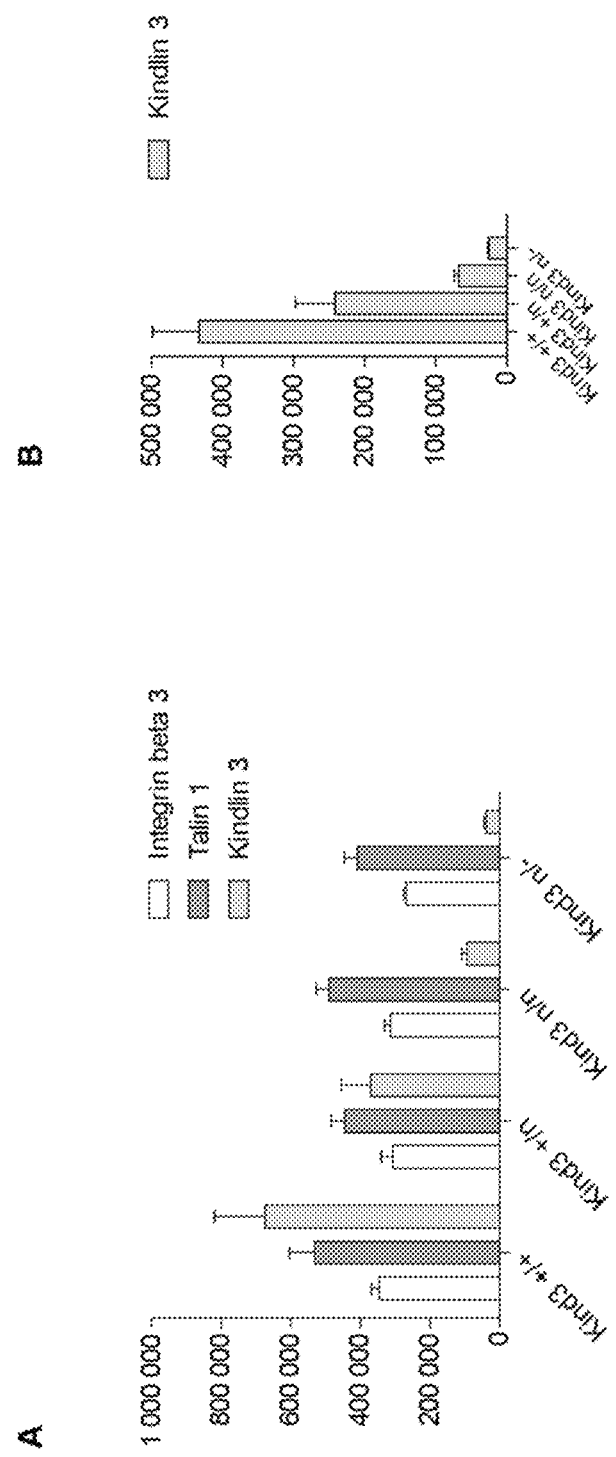
FIG. 9: Absolute quantification of the Integrin beta 3, Talin 1 and Kindlin 3 in different mice. (a) the integrin and its co-activators grouped together. (b) the decreasing expression levels of Kindlin 3 in comparison to the wild-type mice.

Integrin beta 3 and its co-activators are highly abundant proteins in platelets and Itgb3 has on average 300,000 copies per cell, while its co-activators Talin 1 has 470,000 copies and Kindlin 3 has on average 430,000 copies per platelet (Table 3, FIG. 9a). We measured copy numbers of the target proteins in the different mice in duplicates and using two different PrESTs. The difference between platelets samples was on average 20%, whereas the difference between PrESTs is 22%. For the Kindlin 3 calculation we only considered one PrESTs since this targets the region of biological interest—the C-terminus of Kindlin 3 interacts to the cytoplasmic tail of Integrin beta 3.

Besides the copies per cell we also observed the decrease of the expression level of Kindlin 3 in the different knock-outs (FIG. 9b). In comparison to the wild-type mice Kindlin 3 diminished as expected to 50% in the Kind3$^{+/n}$ mice, to 15% in Kind3$^{n/n}$ mice and to 6% Kind3$^{n/-}$ mice and the trend is in agreement with observations of Moser et al. (32).

TABLE 3

Copy numbers per platelet. The absolute amounts of the proteins of interest were measured each using two PrESTs in two mice samples.

| | Integrin beta 3 | Talin 1 | Kindlin 3 | % |
|---|---|---|---|---|
| Kind3 +/+ | 345,000 | 531,000 | 433,000 | 100 |
| Kind3 +/n | 306,000 | 445,000 | 242,000 | 55 |
| Kind3 n/n | 313,000 | 490,000 | 68,000 | 15 |
| Kind3 n/− | 268,000 | 409,000 | 26,000 | 6 |

Using the absolute amount the stoichiometry of the three proteins (Table 2) in the wild-type mice was determined to be 1:1.5:1.3 and this stoichiometry information helps to further understand the binding of co-activators and the activation of integrins.

TABLE 4

Stoichiometry of the protein calculated in wild-type mice using the absolute expression levels.

| | Integrin beta 3 | Talin 1 | Kindlin 3 |
|---|---|---|---|
| Copy number | 345,000 | 531,000 | 433,000 |
| Stoichiometry | 1 | 1.5 | 1.3 |

FURTHER REFERENCES

1. Aebersold, R., and Mann, M. (2003) Mass spectrometry-based proteomics. *Nature* 422, 198-207.
2. Cravatt, B. F., Simon, G. M., and Yates, J. R., 3rd (2007) The biological impact of massspectrometry-based proteomics. *Nature* 450, 991-1000.
3. Gstaiger, M., and Aebersold, R. (2009) Applying mass spectrometry-based proteomics to genetics, genomics and network biology. *Nat Rev Genet.* 10, 617-627.
4. Ong, S. E., and Mann, M. (2005) Mass spectrometry-based proteomics turns quantitative. *Nature chemical biology* 1, 252-262.
5. Bachi, A., and Bonaldi, T. (2008) Quantitative proteomics as a new piece of the systems biology puzzle. *J Proteomics* 71, 357-367.
6. Bantscheff, M., Schirle, M., Sweetman, G., Rick, J., and Kuster, B. (2007) Quantitative mass spectrometry in proteomics: a critical review. *Anal Bioanal Chem* 389, 1017-1031.
7. Ong, S. E., Blagoev, B., Kratchmarova, I., Kristensen, D. B., Steen, H., Pandey, A., and Mann, M. (2002) Stable isotope labeling by amino acids in cell culture, SILAC, as a simple and accurate approach to expression proteomics. *Mol Cell Proteomics* 1, 376-386.
8. Mann, M. (2006) Functional and quantitative proteomics using SILAC. *Nat Rev Mol Cell Biol* 7, 952-958.
9. Geiger, T., Wisniewski, J. R., Cox, J., Zanivan, S., Kruger, M., Ishihama, Y., and Mann, M. (2011) Use of stable isotope labeling by amino acids in cell culture as a spike-in standard in quantitative proteomics. *Nature protocols* 6, 147-157.
10. Brun, V., Masselon, C., Garin, J., and Dupuis, A. (2009) Isotope dilution strategies for absolute quantitative proteomics. *J Proteomics* 72, 740-749.
11. Gerber, S. A., Rush, J., Stemman, O., Kirschner, M. W., and Gygi, S. P. (2003) Absolute quantification of proteins and phosphoproteins from cell lysates by tandem MS. *Proceedings of the National Academy of Sciences of the United States of America* 100, 6940-6945.
12. Beynon, R. J., Doherty, M. K., Pratt, J. M., and Gaskell, S. J. (2005) Multiplexed absolute quantification in proteomics using artificial QCAT proteins of concatenated signature peptides. *Nature methods* 2, 587-589.
13. Pratt, J. M., Simpson, D. M., Doherty, M. K., Rivers, J., Gaskell, S. J., and Beynon, R. J. (2006) Multiplexed absolute quantification for proteomics using concatenated signature peptides encoded by QconCAT genes. *Nature protocols* 1, 1029-1043.
14. Brun, V., Dupuis, A., Adrait, A., Marcellin, M., Thomas, D., Court, M., Vandenesch, F., and Garin, J. (2007) Isotope-labeled protein standards: toward absolute quantitative proteomics. *Mol Cell Proteomics* 6, 2139-2149.
15. Hanke, S., Besir, H., Oesterhelt, D., and Mann, M. (2008) Absolute SILAC for accurate quantitation of proteins in complex mixtures down to the attomole level. *Journal of proteome research* 7, 1118-1130.
16. Singh, S., Springer, M., Steen, J., Kirschner, M. W., and Steen, H. (2009) FLEXIQuant: a novel tool for the absolute quantification of proteins, and the simultaneous identification and quantification of potentially modified peptides. *Journal of proteome research* 8, 2201-2210.
17. Kuster, B., Schirle, M., Mallick, P., and Aebersold, R. (2005) Scoring proteomes with proteotypic peptide probes. *Nat Rev Mol Cell Biol* 6, 577-583.
18. Berglund, L., Bjorling, E., Jonasson, K., Rockberg, J., Fagerberg, L., Al-Khalili Szigyarto, C., Sivertsson, A., and Uhlen, M. (2008) A whole-genome bioinformatics approach to selection of antigens for systematic antibody generation. *Proteomics* 8, 2832-2839.
19. Larsson, M., Graslund, S., Yuan, L., Brundell, E., Uhlen, M., Hoog, C., and Stahl, S. (2000) Highthroughput protein expression of cDNA products as a tool in functional genomics. *Journal of biotechnology* 80, 143-157.
20. Agaton, C., Galli, J., Hoiden Guthenberg, I., Janzon, L., Hansson, M., Asplund, A., Brundell, E., Lindberg, S., Ruthberg, I., Wester, K., Wurtz, D., Hoog, C., Lundeberg, J., Stahl, S., Ponten, F., and Uhlen, M. (2003) Affinity proteomics for systematic protein profiling of chromosome 21 gene products in human tissues. *Mol Cell Proteomics* 2, 405-414.
21. Li, M. Z., and Elledge, S. J. (2007) Harnessing homologous recombination in vitro to generate recombinant DNA via SLIC. *Nature methods* 4, 251-256.
22. Studier, F. W. (2005) Protein production by auto-induction in high density shaking cultures. *Protein expression and purification* 41, 207-234.
23. Wisniewski, J. R., Zougman, A., Nagaraj, N., and Mann, M. (2009) Universal sample preparation method for proteome analysis. *Nature methods* 6, 359-362.
24. Wisniewski, J. R., Zougman, A., and Mann, M. (2009) Combination of FASP and StageTip-based fractionation allows in-depth analysis of the hippocampal membrane proteome. *Journal of proteome research* 8, 5674-5678.
25. Rappsilber, J., Ishihama, Y., and Mann, M. (2003) Stop and go extraction tips for matrix-assisted laser desorption/ionization, nanoelectrospray, and LC/MS sample pretreatment in proteomics. *Analytical chemistry* 75, 663-670.
26. Geiger, T., Cox, J., and Mann, M. (2010) Proteomics on an Orbitrap benchtop mass spectrometer using all-ion fragmentation. *Mol Cell Proteomics* 9, 2252-2261.
27. Cox, J., and Mann, M. (2008) MaxQuant enables high peptide identification rates, individualized p.p.b.-range mass accuracies and proteome-wide protein quantification. *Nature biotechnology* 26, 1367-1372.
28. Cox, J., Neuhauser, N., Michalski, A., Scheltema, R. A., Olsen, J. V., and Mann, M. (2011) Andromeda—a peptide search engine integrated into the MaxQuant environment. *Journal of proteome research*.
29. Tegel, H., Steen, J., Konrad, A., Nikdin, H., Pettersson, K., Stenvall, M., Tourle, S., Wrethagen, U., Xu, L., Yderland, L., Uhlen, M., Hober, S., and Ottosson, J. (2009) High-throughput protein production—lessons from scaling up from 10 to 288 recombinant proteins per week. Biotechnol J 4, 51-57.
30. Wisniewski, J. R., Zougman, A., Nagaraj, N., and Mann, M. (2009) Universal sample preparation method for proteome analysis. Nat Methods 6, 359-362.
31. Moser, M., Legate, K. R., Zent, R., and Fassler, R. (2009) The tail of integrins, talin, and kindlins. Science 324, 895-899.
32. Moser, M., Nieswandt, B., Ussar, S., Pozgajova, M., and Fassler, R. (2008) Kindlin-3 is essential for integrin activation and platelet aggregation. Nat Med 14, 325-330.
33. Matic, I., Jaffray, E. G., Oxenham, S. K., Groves, M. J., Barratt, C. L., Tauro, S., Stanley-Wall, N. R., and Hay, R. T. (2011) Absolute SILAC-compatible expression strain allows Sumo-2 copy number determination in clinical samples. J Proteome Res 10, 4869-4875.
34. Olsen, J. V., Schwartz, J. C., Griep-Raming, J., Nielsen, M. L., Damoc, E., Denisov, E., Lange, O., Remes, P., Taylor, D., Splendore, M., Wouters, E. R., Senko, M., Makarov, A., Mann, M., and Horning, S. (2009) A dual pressure linear ion trap Orbitrap instrument with very high sequencing speed. Mol Cell Proteomics 8, 2759-2769.

The invention claimed is:

1. A method of determining the absolute amount of a target polypeptide in a sample, said method comprising the following steps:
   (a) adding
      (aa) a fusion polypeptide to said sample, said fusion polypeptide comprising (i) at least one tag sequence and (ii) a subsequence of the target polypeptide; and
      (ab) a known absolute amount of a tag polypeptide comprising or consisting of said tag sequence according to (aa)
   to said sample, wherein said fusion polypeptide is mass-altered as compared to said target polypeptide and said tag polypeptide, said mass-alteration resulting from isotope labeling or isobaric tagging;
   (b) performing proteolytic digestion of the mixture obtained in step (a);
   (c) subjecting the result of proteolytic digestion of step (b), optionally after chromatography, to mass spectrometric analysis; and
   (d) determining the absolute amount of said target polypeptide from (i) the peak intensities in the mass spectrum acquired in step (c) of said fusion polypeptide, said tag polypeptide and said target polypeptide and (ii) said known absolute amount of said tag polypeptide.

2. A method of creating a quantitative standard, said method comprising the following steps:
   (a) providing one or a plurality of fusion polypeptides, the one fusion polypeptide or each of said fusion polypeptides, respectively, comprising (i) at least one tag sequence and (ii) a subsequence of a target polypeptide to be quantitatively determined, wherein, to the extent said plurality of fusion polypeptides is provided, all fusion polypeptides share at least one tag sequence, thereby obtaining the standard;
   (b) determining the absolute amounts of said fusion polypeptide(s) by
      (ba) adding to the one fusion polypeptide or to one of said fusion polypeptides at a time, respectively, a known amount of a tag polypeptide comprising or consisting of the tag sequence comprised in the one fusion polypeptide or shared among the fusion polypeptides, respectively, according to (a), wherein said fusion polypeptide is mass-altered as compared to said tag polypeptide, said mass-alteration resulting from isotope labeling or isobaric tagging;
      (bb) performing proteolytic digestion of the mixture of one fusion polypeptide and said tag polypeptide obtained in step (ba);
      (bc) subjecting of the result of proteolytic digestion of step (bb), optionally after chromatography, to mass spectrometric analysis; and
      (bd) determining the absolute amount of said one fusion polypeptide from (i) the peak intensities in the mass spectrum of fusion polypeptide and tag polypeptide and (ii) said known amount of said tag polypeptide,
   thereby obtaining the absolute amount of the one fusion polypeptide or of one of said plurality of fusion polypeptides at a time, respectively.

3. A method of determining the absolute amount of one or more target polypeptides in a sample, said method comprising the following steps:
   (a) adding the quantitative standard as defined in claim 2 (a) to said sample;
   (b) performing proteolytic digestion of the mixture obtained in step (b);
   (c) subjecting the result of proteolytic digestion of step (c), optionally after chromatography, to mass spectrometric analysis; and
   (d) determining the absolute amounts of the target polypeptide(s) from (i) the peak intensities in the mass spectrum acquired in step (d) of fusion polypeptide(s) and target polypeptide(s) and (ii) the known absolute amount(s) of said fusion polypeptide(s),
   wherein said fusion polypeptide(s) is/are mass-altered as compared to said target polypeptide(s), said mass-alteration resulting from isotope labeling or isobaric tagging.

4. The method of claim 1, wherein one or two tags are present in said fusion polypeptide(s), said tag(s) being selected from a purification tag and a solubility tag.

5. The method of claim 1, wherein said adding is effected prior to said proteolytic digestion.

6. The method of claim 2, wherein between two and 500 fusion polypeptides are used.

7. The method of claim 1, wherein a solubility tag is present in each of said fusion polypeptides.

8. The method of claim 1, wherein said subsequence of a polypeptide
   (a) consists of 15 to 205 amino acids;
   (b) comprises a proteotypic peptide; and/or
   (c) is selected to have minimal sequence identity to other proteins, excludes signal peptides and/or excludes sequences from transmembrane spanning regions.

9. A fusion polypeptide for the quantification of a target polypeptide by mass spectroscopy, wherein:
   said fusion polypeptide consists of 35-455 amino acid residues and comprises (i) a target region, which is a fragment of the target polypeptide, and (ii) a tag region, which is not a fragment of the target polypeptide,
   said target region consists of 15-205 amino acid residues and comprises at least two signature regions;
   said tag region consists of 20-250 amino acid residues and comprises at least two signature regions;
   each signature region has the structure $Y\text{-}Z\text{-}X_{4\text{-}28}\text{-}Y\text{-}Z$, wherein
   Y is selected from one of (i)-(iv), wherein (i) is R or K, (ii) is Y, F, W or L, (iii) is E and (iv) is D, and each X and each Z is independently any amino acid residue, provided that Z is not P if Y is selected from (i)-(iii); each signature region comprises at least one amino acid residue comprising a heavy isotope; and said tag region corresponds to Albumin Binding Protein (ABP) or a fragment thereof.

10. The fusion polypeptide of claim 9, wherein said tag region comprises the sequence set forth in SEQ ID NO: 1.

11. The fusion polypeptide of claim 9, wherein Y is selected from R and K.

12. The method according to claim 1 wherein said fusion polypeptide(s) consist(s) of 35-455 amino acid residues and comprise(s) (i) a target region, which is a fragment of the target polypeptide, and (ii) a tag region, which is not a fragment of the target polypeptide,
said target region consists of 15-205 amino acid residues and comprises at least two signature regions;
said tag region consists of 20-250 amino acid residues and comprises at least two signature regions;
each signature region has the structure $Y-Z-X_{4-28}-Y-Z$, wherein
Y is selected from one of (i)-(iv), wherein (i) is R or K, (ii) is Y, F, W or L, (iii) is E and (iv) is D and each X and each Z is independently any amino acid residue, provided that Z is not P if Y is selected from (i)-(iii); and each signature region comprises at least one amino acid residue comprising a heavy isotope.

13. A kit comprising:
(a) at least one fusion polypeptide according to claim 9; and
(b) (i) a second polypeptide comprising or consisting of the amino acid sequence of the tag region as defined in claim 9, said second polypeptide being differently isotope labeled compared to said tag region as defined in claim 9 or
(ii) a proteolytic enzyme, such as trypsin, chymotrypsin, Lys-C, Glu-C or Asp-N.

14. The method of claim 1, comprising the use of a quantitative standard produced by the method of claim 2.

15. The method of claim 3, further comprising performing the method of claim 2 before adding.

16. The method of claim 2, wherein one or two tags are present in said fusion polypeptide(s), said tag(s) being selected from a purification tag and a solubility tag.

17. The method of claim 3, wherein one or two tags are present in said fusion polypeptide(s), said tag(s) being selected from a purification tag and a solubility tag.

18. The method of claim 3, wherein between two and 500 fusion polypeptides are used.

19. The method of claim 2, wherein a solubility tag is present in each of said fusion polypeptides.

20. The method of claim 3, wherein a solubility tag is present in each of said fusion polypeptides.

21. The method of claim 2, wherein said subsequence of a polypeptide
(a) consists of 15 to 205 amino acids;
(b) comprises a proteotypic peptide; and/or
(c) is selected to have minimal sequence identity to other proteins, excludes signal peptides and/or excludes sequences from transmembrane spanning regions.

22. The method according to claim 2, wherein said fusion polypeptide(s) consist(s) of 35-455 amino acid residues and comprise(s) (i) a target region, which is a fragment of the target polypeptide, and (ii) a tag region, which is not a fragment of the target polypeptide,
said target region consists of 15-205 amino acid residues and comprises at least two signature regions;
said tag region consists of 20-250 amino acid residues and comprises at least two signature regions;
each signature region has the structure $Y-Z-X_{4-28}-Y-Z$, wherein
Y is selected from one of (i)-(iv), wherein (i) is R or K, (ii) is Y, F, W or L, (iii) is E and (iv) is D and each X and each Z is independently any amino acid residue, provided that Z is not P if Y is selected from (i)-(iii); and each signature region comprises at least one amino acid residue comprising a heavy isotope.

23. The method of claim 1, comprising using the polypeptide of claim 9 as a reference.

24. The method of claim 1, wherein the fusion polypeptide is mass-altered by having different isotope labeling from the target polypeptide and the tag polypeptide.

25. The method of claim 24, wherein the target polypeptide and the tag polypeptide have different isotope labeling from one another.

26. The method of claim 24, wherein the fusion polypeptide is isotope labeled.

27. The method of claim 24, wherein the fusion polypeptide is not isotope labeled.

28. The method of claim 2, wherein the fusion polypeptide is mass-altered by having different isotope labeling from the tag polypeptide.

29. The method of claim 3, wherein the fusion polypeptide is mass-altered by having different isotope labeling from the one or more target polypeptides.

30. The fusion polypeptide of claim 9, wherein said target region consists of 20 to 150 amino acid residues.

31. The fusion polypeptide of claim 9, wherein said tag region consists of 40 to 150 amino acid residues.

32. The fusion polypeptide of claim 9, wherein said fusion polypeptide consists of 80 to 300 amino acid residues.

33. The fusion polypeptide of claim 9, wherein the at least one amino acid residue comprising a heavy isotope is selected from L-arginine-$^{13}C_6$, L-arginine-$^{13}C_6{}^{15}N_4$, L-arginine-$^{13}C_6{}^{15}N_4D_7$, L-arginine-$^{15}N_4D_7$, L-arginine-$^{15}N_4$, L-lysine-$^{13}C_6{}^{15}N_2$, L-lysine-$^{15}N_2$, L-lysine-$^{13}C_6$, L-lysine-$^{13}C_6{}^{15}N_2D_9$, L-lysine-$^{15}N_2D_9$, L-lysine-$D_4$, L-methionine-$^{13}CD_3$, L-tyrosine-$^{13}C_9$, L-tyrosine-$^{15}N$, L-arginine-$^{13}C_9{}^{15}N$.

34. The fusion polypeptide of claim 9, wherein all arginine and lysine residues are labelled.

35. The fusion polypeptide of claim 9 further comprising a purification tag.

36. The fusion polypeptide of claim 35, wherein said purification tag is selected from a His tag, a SBP tag, and a myc tag.

* * * * *